US008765796B2

(12) United States Patent
Herr et al.

(10) Patent No.: US 8,765,796 B2
(45) Date of Patent: *Jul. 1, 2014

(54) COMPOUNDS, METHODS AND FORMULATIONS FOR THE ORAL DELIVERY OF A GLUCAGON-LIKE PEPTIDE (GLP-1) COMPOUND OR A MELANOCORTIN-4 RECEPTOR (MC4) AGONIST PEPTIDE

(71) Applicant: Emisphere Technologies, Inc., Roseland, NJ (US)

(72) Inventors: Robert J. Herr, Voorheesville, NY (US); Louis N. Jungheim, Indianapolis, IN (US); John M. McGill, Greenwood, IN (US); Kenneth J. Thrasher, Indianapolis, IN (US); Muralikrishna Valluri, Rensselaer, NY (US)

(73) Assignee: Emisphere Technologies, Inc., Roseland, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/971,680

(22) Filed: Aug. 20, 2013

(65) Prior Publication Data

US 2014/0031287 A1    Jan. 30, 2014

Related U.S. Application Data

(60) Continuation of application No. 12/636,244, filed on Dec. 11, 2009, now Pat. No. 8,552,039, which is a division of application No. 10/566,342, filed as application No. PCT/US2004/024386 on Aug. 18, 2004, now Pat. No. 7,662,771.

(60) Provisional application No. 60/496,537, filed on Aug. 20, 2003.

(51) Int. Cl.
*A61K 31/421*     (2006.01)
*C07D 263/30*     (2006.01)

(52) U.S. Cl.
USPC .......................................... 514/374; 548/236

(58) Field of Classification Search
USPC ........................................... 514/374; 548/236
See application file for complete search history.

(56) References Cited

U.S. PATENT DOCUMENTS

| 2,423,709 A | 7/1947 | Knott |
| 3,578,671 A | 5/1971 | Brown |
| 4,239,754 A | 12/1980 | Sache et al. |
| 4,925,673 A | 5/1990 | Steiner et al. |
| 5,273,989 A | 12/1993 | Schwab et al. |
| 5,541,155 A | 7/1996 | Leone-Bay et al. |
| 5,643,957 A | 7/1997 | Leone-Bay et al. |
| 5,650,386 A | 7/1997 | Leone-Bay et al. |
| 5,693,338 A | 12/1997 | Milstein |
| 5,820,881 A | 10/1998 | Milstein |
| 5,866,536 A | 2/1999 | Leone-Bay et al. |
| 5,955,503 A | 9/1999 | Leone-Bay et al. |
| 5,965,121 A | 10/1999 | Leone-Bay et al. |
| 5,976,569 A | 11/1999 | Milstein |
| 5,989,539 A | 11/1999 | Leone-Bay et al. |
| 5,995,503 A | 11/1999 | Crawley et al. |
| 6,001,347 A | 12/1999 | Leone-Bay et al. |
| 6,071,510 A | 6/2000 | Leone-Bay et al. |
| 6,100,298 A | 8/2000 | Leone-Bay et al. |
| 6,211,215 B1 | 4/2001 | Momose et al. |
| 6,242,495 B1 | 6/2001 | Leone-Bay et al. |
| 6,294,580 B1 | 9/2001 | Willson et al. |
| 6,578,671 B2 | 6/2003 | Shen |
| 6,605,629 B1 | 8/2003 | Momose et al. |
| 6,903,085 B1 | 6/2005 | Thom et al. |
| 6,924,284 B2 | 8/2005 | Beaton et al. |
| 6,930,120 B2 | 8/2005 | Brooks et al. |
| 6,982,278 B2 | 1/2006 | Brooks et al. |
| 7,022,725 B2 | 4/2006 | Momose et al. |
| 7,351,728 B2 | 4/2008 | Brooks et al. |
| 7,662,771 B2 | 2/2010 | Herr et al. |
| 8,552,039 B2 * | 10/2013 | Herr et al. .............. 514/374 |
| 2004/0048908 A1 | 3/2004 | Momose et al. |
| 2004/0077557 A1 | 4/2004 | Ali et al. |
| 2006/0148858 A1 | 7/2006 | Maekawa et al. |

FOREIGN PATENT DOCUMENTS

| GB | 1129393 A | 10/1968 |
| GB | 2373186 A | 9/2002 |
| JP | 1160571 A | 4/1980 |
| JP | 4234857 A | 8/1992 |
| JP | 2002-212171 A | 7/2002 |
| JP | 2003507456 A | 2/2003 |
| JP | 2004277397 A | 10/2004 |
| WO | WO-0040203 A2 | 7/2000 |
| WO | WO-0047188 A1 | 8/2000 |
| WO | WO-0050386 A1 | 8/2000 |
| WO | WO-0059863 A1 | 10/2000 |
| WO | WO-0132130 A2 | 5/2001 |
| WO | WO-0144199 A1 | 6/2001 |
| WO | WO-0151454 A1 | 7/2001 |
| WO | WO-0202509 A1 | 1/2002 |
| WO | WO-0246129 | 6/2002 |
| WO | WO-0250091 A1 | 6/2002 |
| WO | WO-02064607 A1 | 8/2002 |

(Continued)

OTHER PUBLICATIONS

Acta Chemica Scandinavica, (1972), 26(2), p. 541-8.

(Continued)

*Primary Examiner* — Kristin Vajda
(74) *Attorney, Agent, or Firm* — Blank Rome LLP

(57) ABSTRACT

The present invention relates to novel compounds, methods, and formulations useful for the oral delivery of a GLP-1 compound or an MC4 agonist peptide.

12 Claims, No Drawings

(56) References Cited

FOREIGN PATENT DOCUMENTS

| WO | WO-02096359 A2 | 12/2002 |
| WO | WO-03015785 A1 | 2/2003 |
| WO | WO-03057215 A1 | 7/2003 |
| WO | WO-03072195 A2 | 9/2003 |
| WO | WO-2005000339 A2 | 1/2005 |

OTHER PUBLICATIONS

Dai, Y. et al., A Novel Series of Histone Deactylase Ihibitors Incorporatin Hetero Aromatic Ring Systems as Connection Units, Science Direct, Bioorganix and Medicinal Chemistry Letters, 13, pp. 3817-3820, 2003.

Hashimoto, A. et al., Effects of Oral Administration of Positvely Charged Insulin Liposomes on Alloxan Diabetic Rats: Preliminary Study, Endocrinology Jpaan, vol. 26, No. 3, pp. 337-344, 1979.

Janda et al., STN Accession No. 2002-29404; Document No. 136:340636; Abstract of Heterocyclic Communications (2001) 7(5), 411-436.

Moriya et al. Journal of Medicinal Chemistry, (1988), 31(6), 1197-1204.

Patel, H. et al., Oral Administration of Insulin by Encapsulation Within Liposomes, FEBS Letters, vol. 62, No. 1, pp. 60-63, 1976.

J. Med. Chem., (1970), 13(4), p. 725-9.

Yasuyoshi Iso et al., Efficient Synthesis of Resin-Bound alpha-TMSdiazoketones and Their Use in Solid-Phase Organic Synthesis, 2000, Tetrahedron, 56, 5353-5361.

Hinegardner et al., The Synthesis of Thiazole Amines Possessing Pharmacological Interest, 1930, J. Amer. Chemical Soc., 52, p. 4140.

* cited by examiner

COMPOUNDS, METHODS AND FORMULATIONS FOR THE ORAL DELIVERY OF A GLUCAGON-LIKE PEPTIDE (GLP-1) COMPOUND OR A MELANOCORTIN-4 RECEPTOR (MC4) AGONIST PEPTIDE

This application is a continuation of U.S. patent application Ser. No. 12/636,244, filed Dec. 11, 2009, which is a divisional application of U.S. patent application Ser. No. 10/566,342, filed Jan. 27, 2006 (now U.S. Pat. No. 7,662,771), which is the U.S. national phase of International Patent Application No. PCT/US2004/024386, filed Aug. 18, 2004, which claims the benefit of U.S. Provisional Patent Application No. 60/496,537, filed Aug. 20, 2003, each of which is hereby incorporated by reference.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers. In the delivery to animals of biologically active or chemically active pharmacological and therapeutic agents, physical and chemical barriers are imposed by the body. Examples of physical barriers are the skin and various organ membranes that must be traversed before reaching a target, and examples of chemical barriers include, but are not limited to, variations in pH, lipid bilayers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of excipients or enhancers (e.g., resorcinols and non-ionic surfactants such as polyoxyethylene oleyl ether and n-hexadecylpolyethylene ether) to increase artificially the permeability of the intestinal walls, as well as the co-administration of enzyme inhibitors (e.g., pancreatic trypsin inhibitors, diisopropylfluorophosphate) to inhibit enzymatic degradation.

Liposomes have also been described as drug delivery systems for insulin and heparin. See, for example, U.S. Pat. No. 4,239,754; Patel et al (1976), FEBS Letters, Vol 62, pg. 60, and Hashimoto et al. (1970), Endocrinology Japan, Vol, 26, pg. 337.

However, broad spectrum use of such drug delivery systems is precluded because: (1) the systems require toxic amounts of excipients, enhancers or inhibitors; (2) suitable low molecular weight cargos, i.e. active agents, are not available; (3) they exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

Delivery agent molecules have also been disclosed in U.S. Pat. Nos. 5,541,155; 5,693,338; 5,976,569; 5,643,957; 5,955,503; 6,100,298; 5,650,386; 5,866,536; 5,965,121; 5,989,539; 6,001,347; 6,071,510; 5,820,881; and 6,242,495; see also WO 02/02509; WO 01/51454; WO 01/44199; WO 01/32130; WO 00/59863; WO 00/50386; WO 00/47188; and WO 00/40203.

BRIEF SUMMARY OF THE INVENTION

The present invention relates to a compound of formula I:

$$\underset{R^2}{\overset{R^1}{\bigvee}}\!\!\!\diagdown\!\!\diagup\!\!\!-X-(CH_2)_n-CO_2R^3; \quad I$$

wherein
$R^1$ and $R^2$ are each independently H, OH, cyano, $C_1$-$C_6$ alkyl, $C_1$-$C_6$ alkoxy, $CF_3$, halo or $NR^4R^{4'}$;
$R^3$ is H, $C_1$-$C_6$ alkyl;
$R^4$ is H, $COR^5$, $SO_2R^6$, or $C_1$-$C_6$ alkyl;
$R^{4'}$ is H or $C_1$-$C_6$ alkyl;
$R^5$ is H or $C_1$-$C_6$ alkyl;
$R^6$ is H or $C_1$-$C_6$ alkyl;
X is a 5 membered aromatic heterocycle that is optionally substituted with C1-C4 alkyl; wherein said heterocycle contains at least two or three heteroatoms selected from N, S and O wherein at least one heteroatom must be N and wherein said heterocycle may not be 1,3,4-oxadiazole;
n is 2, 3, 4, 5, 6 or 7;
or a pharmaceutical salt thereof.

The present invention further relates to a compound of formula I wherein $R^3$ is H. This compound is hereafter referred to as a compound of formula II.

The present invention also relates to a pharmaceutical composition containing a compound of formula II, or a pharmaceutical salt thereof, and a pharmaceutical carrier.

The present invention also relates to a pharmaceutical composition containing a compound of formula II, or a pharmaceutical salt thereof, and a GLP-1 compound.

The present invention also relates to a pharmaceutical composition containing a compound of formula II, or a pharmaceutical salt thereof, and a MC4 agonist peptide.

DETAILED DESCRIPTION OF THE INVENTION

Reference hereafter to "a compound of formula I" or "compound of formula II" includes the pharmaceutical salts thereof.

For the purposes of the present invention, as disclosed and claimed herein, the following terms are defined below.

The term "halo" refers to fluoro, chloro, bromo and iodo. The term "$C_1$-$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. Moieties such as a cyclobutylmethylene are also included within the scope of a $C_1$-$C_6$ alkyl group. The term "$C_1$-$C_4$ alkyl" refers specifically to methyl, ethyl, n-propyl, isopropyl, cyclopropyl, cyclopropylmethyl, n-butyl, isobutyl, sec-butyl, t-butyl and cyclobutyl. A "$C_1$-$C_6$ alkoxy" group is a $C_1$-$C_6$ alkyl moiety connected through an oxy linkage.

The term "pharmaceutical" when used herein as an adjective means substantially non-deleterious to the recipient patient.

The term "patient" includes humans and non-human animals such as companion animals (dogs, cats, horses and the like). The preferred patient of treatment is a human.

The term "GLP-1 compound" as used herein refers to one or more naturally occurring GLP-1 polypeptides (GLP-1(7-37)OH and GLP-1(7-36)$NH_2$), GLP-1 fragments, GLP-1 analogs, GLP-1 derivatives of naturally occurring GLP-1 polypeptides, GLP-1 fragments, or GLP-1 analogs, and Exendin-3 and Exendin-4 that have the ability to bind to the GLP-1 receptor and initiate a signal transduction pathway resulting in insulinotropic activity as described in PCT Publication Number WO 03/072195 (Application Number PCT/US03/03111); herein incorporated by reference.

The term "MC4 agonist peptide" as used herein refers to the pharmaceutically useful peptides disclosed in PCT Patent Application No. PCT/US04/16625, filed Jun. 17, 2004 (peptides of formula I, II and III as disclosed therein).

The compound of formula II is useful for increasing the oral bioavailability of an active agent, i.e., a GLP-1 compound or an MC4 agonist peptide, when said compound is mixed with the active agent to form a combination composition. Said combination is one embodiment of the present invention. The compositions of the present invention comprise a compound of formula II, that is, a delivery agent (a formula II compound), and a GLP-1 compound or an MC4 agonist peptide.

The present invention is particularly advantageous for delivering a GLP-1 compound or an MC4 agonist peptide (active agent) that would otherwise be destroyed or rendered less effective by conditions encountered before the active agent reaches its target zone (i.e. the area in which the active agent of the delivery composition is to be released) and within the body of the animal to which it is administered. The compositions comprising one or more compounds of formula II (preferably and most typically one) and an active agent have utility in the delivery of said active agent to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Preferred Compounds (Embodiments) of the Invention

Certain compounds of the invention are particularly interesting and are preferred. The following listing sets out several groups of preferred compounds. It will be understood that each of the listings may be combined with other listings to create additional groups of preferred compounds.

n is 2, 3, 4 or 5;
$R^1$ and $R^2$ are each independently H, OH, $OCH_3CH_3$, $CF_3$, Cl, or Br;
$R^1$ and $R^2$ are each independently H, OH, $OCH_3CH_3$ or $CF_3$;
$R^1$ and $R^2$ are each independently H, OH, $OCH_3$ or $NH_2$;
$R^3$ is H;
$R^4$ is H;
$R^4$ is $COR^5$ and $R^5$ is $CH_3$;
$R^4$ is $SO_2R^6$ and $R^6$ is $CH_3$;
$R^{4'}$ is H;
$R^6$ is $C_1$-$C_6$ alkyl;
X is

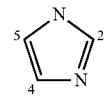

and the phenyl substituent is attached at either carbon atom number 4 or 5 and the alkanoic acid is attached at carbon atom number 2;
X is

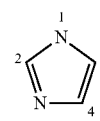

and the phenyl substituent is attached at either carbon atom number 2 or 4 and the alkanoic acid is attached at nitrogen atom number 1;
X is

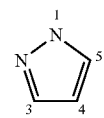

and the phenyl substituent is attached at carbon atom number 3 and the alkanoic acid is attached at nitrogen atom number 1;
X is

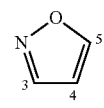

and the phenyl substituent is attached at carbon atom number 3 and the alkanoic acid is attached at carbon atom number 5;
X is

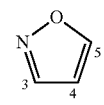

and the phenyl substituent is attached at carbon atom number 3 and the alkanoic acid is attached at carbon atom number 4;

X is

and the phenyl substituent is attached at carbon atom number 5 and the alkanoic acid is attached at carbon atom number 3;

X is

optionally substituted with methyl at carbon atom number 5 where the phenyl substituent is attached at carbon atom number 4 and the alkanoic acid chain is attached at carbon atom number 2;

X is

optionally substituted with methyl at carbon atom number 4 where the phenyl substituent is attached at carbon atom number 2 and the alkanoic acid chain is attached at carbon atom number 5;

X is

and the phenyl substituent is attached at carbon atom number 2 and the alkanoic acid chain is attached at carbon atom number 5;

X is

and the phenyl substituent is attached at carbon atom number 4 and the alkanoic acid chain is attached at carbon atom number 2;

X is

and the phenyl substituent is attached at carbon atom number 5 and the alkanoic acid is attached at carbon atom number 2;

X is

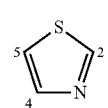

and the phenyl substituent is attached at carbon atom number 4 and the alkanoic acid is attached at carbon atom number 2;

X is

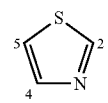

and the phenyl substituent is attached at carbon atom number 5 and the alkanoic acid is attached at carbon atom number 2;

X is

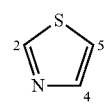

and the phenyl substituent is attached at carbon atom number 2 and the alkanoic acid is attached at carbon atom number 4;

X is

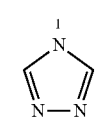

optionally substituted at nitrogen atom number 1 with methyl;

X is

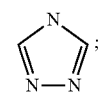

X is

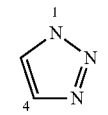

and the phenyl substituent is attached at carbon atom number 4 and the alkanoic acid is attached at nitrogen atom number 1;

X is

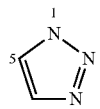

and the phenyl substituent is attached at carbon atom number 5 and the alkanoic acid is attached at nitrogen atom number 1;
X is

and the phenyl substituent is attached at carbon atom number 3 and the alkanoic acid is attached at carbon atom number 5;
X is

and the phenyl substituent is attached at carbon atom number 5 and the alkanoic acid is attached at carbon atom number 3;
X is

and the phenyl substituent is attached at carbon atom number 5 and the alkanoic acid is attached at carbon atom number 2.

PREPARATIONS AND EXAMPLES

All non-aqueous reactions are performed under a dry atmosphere of nitrogen unless otherwise specified. Commercial grade reagents and anhydrous solvents are used as received from vendors and no attempts are made to purify or dry these components further. Removal of solvents under reduced pressure is accomplished with a Buchi rotary evaporator at approximately 28 mm Hg pressure using a Teflon-lined KNF vacuum pump. Thin layer chromatography is performed using 1"×3" Analtech No. 02521, Whatman No. MK6F or EM Science (Merck) No. 5719-2 silica gel plates with fluorescent indicator. Visualization of TLC plates is made by observation with either short wave UV light, 10% phosphomolybdic acid in ethanol or in iodine vapors. Flash column chromatography is carried out using Kieselgel silica gel 60. Proton NMR spectra are obtained on a Bruker AC 300 MHz Nuclear Magnetic Resonance Spectrometer and are reported in ppm δ values, using tetramethylsilane as an internal reference. Melting points are obtained using an Electrothermal melting point apparatus and are uncorrected. CI Mass spectroscopic analyses are performed on a Shimadzu QP-5000 GC/Mass Spectrometer (methane) by direct injection. API Mass spectroscopic analyses are performed on a Finnegan LCQ Duo Ion Trap or a PESciex API 150EX mass spectrometer, using electro spray ionization (ESI) or atmospheric pressure chemical ionization (APCI). HPLC analyses are conducted using a Waters Symmetry C18, 5 um, WAT046980, 3.9×150 mm column. The elution system consisted of 90:10 (0.1% TFA in $H_2O$)/(0.1% TFA in $CH_3CN$) gradient elution to 10:90 (0.1% TFA in $H_2O$)/(0.1% TFA in $CH_3CN$) over 20 min, followed by 10:90 (0.1% TFA in $H_2O$)/(0.1% TFA in $CH_3CN$) isocratic elution for 10 min, followed by 90:10 (0.1% TFA in $H_2O$)/(0.1% TFA in $CH_3CN$) isocratic elution for 10 min. The flow rate is 1 mL/min. UV Detection is performed at both 214 and 254 nm.

Preparation 1

Octanedioic Acid Methyl Ester 2-Oxo-2-phenylethyl Ester

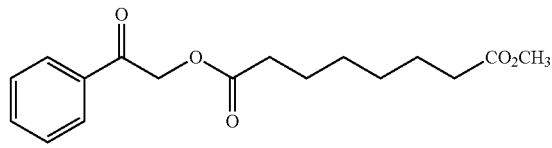 [SMILES: COC(=O)CCCCCCC(=O)OCC(=O)c1ccccc1]

Add a solution of sodium bicarbonate (2.12 g, 25.2 mmol) in water (10 mL) to a solution of suberic acid monomethyl ester (4.75 g, 25.2 mmol) in methanol (50 mL) at room temperature and stir the mixture for 30 minutes. Remove the solvent under reduced pressure and add the residue to a solution of 2-bromoacetophenone (5.0 g, 25.1 mmol) in acetone (150 mL) at room temperature under nitrogen. Heat the mixture at reflux for 10 hours and then remove the solvent under reduced pressure. Dilute the residue with diethyl ether (300 mL), stir for 20 minutes, filter through a short silica gel column, and wash with diethyl ether (2×50 mL). Remove the solvent under reduced pressure to provide octanedioic acid methyl ester 2-oxo-2-phenylethyl ester (6.9 g, 90%).

Example 1

7-(4-Phenyloxazol-2-yl)heptanoic Acid Methyl Ester

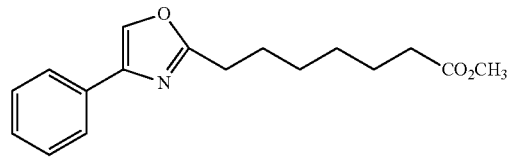 [SMILES: COC(=O)CCCCCCc1nc(-c2ccccc2)co1]

Heat a mixture of octanedioic acid methyl ester 2-oxo-2-phenylethyl ester (6.93 g, 22.6 mmol), acetamide (6.75 g, 114 mmol) and boron trifluoride diethyl etherate (3.0 mL, 23.7 mmol) at 135-140° C. under nitrogen for 4 hours. Cool the mixture, dilute with saturated $NaHCO_3$ solution (100 mL), and extract with ethyl acetate (250 mL). Wash the organic extract with 100 mL of saturated aqueous sodium chloride (brine) and dry over sodium sulfate. Remove the solvent under reduced pressure and purify the residue by flash column chromatography on silica gel, eluting with hexanes/ethyl acetate (85:15), to provide 7-(4-phenyloxazol-2-yl)heptanoic acid methyl ester (5.7 g, 88%).

Example 2

7-(4-Phenyloxazol-2-yl)heptanoic Acid

Add solution of sodium hydroxide (1.60 g, 40.0 mmol) in water (30 mL) to a solution of 7-(4-phenyloxazol-2-yl)heptanoic acid methyl ester (5.75 g, 20.0 mmol) in methanol (40 mL) at room temperature and heat the mixture at 40° C. for 2 hours. Adjust the pH of the mixture to 2 with 1 N HCl and extract with ethyl acetate (600 mL). Wash the organic extract with water (3×150 mL), dry over sodium sulfate and remove the solvent under reduced pressure. Triturate the residue with hexanes/ethyl acetate and collect the solids by filtration to provide 7-(4-phenyloxazol-2-yl)heptanoic acid (5.01 g, 91%): APCI mass spectrum m/z 272 $[C_{16}H_{19}NO_3—H]^-$.

Prepare Examples 3-30, compounds of formula II(a) listed in Table 1 below, by the same process as in the preparation of Example 2.

TABLE 1

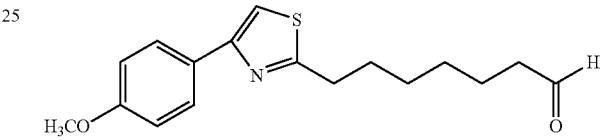

II(a)

Compounds of formula II(a)

| Example | R¹ (position on ring) | R² (position on ring) | n | mass spectrum m/z |
|---|---|---|---|---|
| 3 | OCH₃ (1) | H | 3 | 261 $[C_{14}H_{15}NO_4]^+$ |
| 4 | OCH₃ (1) | H | 4 | 276 $[C_{15}H_{17}NO_4 + H]^+$ |
| 5 | OCH₃ (1) | H | 5 | 290 $[C_{16}H_{19}NO_4 + H]^+$ |
| 6 | OH (1) | H | 4 | 260 $[C_{14}H_{15}NO_4 - H]^-$ |
| 7 | OH (1) | OCH₃ (3) | 4 | 290 $[C_{15}H_{17}NO_5 - H]^-$ |
| 8 | OCH₃ (1) | H | 6 | 302 $[C_{17}H_{21}NO_4 - H]^-$ |
| 9 | H | OCH₃ (3) | 6 | 302 $[C_{17}H_{21}NO_4 - H]^-$ |
| 10 | OH (1) | H | 6 | 288 $[C_{16}H_{19}NO_4 - H]^-$ |
| 11 | OH (1) | OCH₃ (3) | 6 | 318 $[C_{17}H_{21}NO_5 - H]^-$ |
| 12 | OH (1) | Cl (4) | 6 | 322 $[C_{16}H_{18}ClNO_4 - H]^-$ |
| 13 | OH (1) | H | 3 | 246 $[C_{13}H_{13}NO_4 - H]^-$ |
| 14 | OH (1) | F (3) | 4 | 280 $[C_{14}H_{14}FNO_4 + H]^+$ |
| 15 | OH (1) | H | 5 | 276 $[C_{15}H_{17}NO_4 + H]^+$ |
| 16 | OCH₃ (1) | H | 2 | 248 $[C_{13}H_{13}NO_4 + H]^+$ |
| 17 | OH (1) | H | 2 | 234 $[C_{12}H_{11}NO_4 + H]^+$ |
| 18 | OH (1) | OCH₃ (3) | 3 | 276 $[C_{14}H_{15}NO_5 - H]^-$ |
| 19 | H | H | 4 | 246 $[C_{14}H_{15}NO_3 + H]^+$ |
| 20 | F (1) | H | 4 | 264 $[C_{14}H_{14}FNO_3 + H]^+$ |
| 21 | OCH₃ (2) | H | 4 | 276 $[C_{15}H_{17}NO_4 + H]^+$ |
| 22 | OH (2) | H | 4 | 262 $[C_{14}H_{15}NO_4 + H]^+$ |
| 23 | OH (1) | OH (3) | 4 | 278 $[C_{14}H_{15}NO_5 + H]^+$ |
| 24 | OH (1) | OCH₃ (3) | 5 | 304 $[C_{13}H_{13}NO_4 - H]^-$ |
| 25 | OH (1) | OH (5) | 4 | 278 $[C_{14}H_{15}NO_5 + H]^+$ |
| 26 | OH (1) | F (4) | 4 | 278 $[C_{14}H_{14}FNO_4 - H]^-$ |
| 27 | OH (1) | CN (4) | 4 | 285 $[C_{15}H_{14}N_2O_4 - H]^-$ |
| 28 | OH (1) | CN (3) | 4 | 287 $[C_{15}H_{14}N_2O_4 + H]^+$ |
| 29 | OH (1) | Br (3) | 4 | 278 $[C_{14}H_{14}BrNO_4H]^+$ |
| 30 | OH (1) | OCH₃ (4) | 4 | 290 $[C_{15}H_{17}FNO_5 - H]^-$ |
| 174 | OH (1) | Cl (3) | 4 | 294 $[C_{14}H_{14}ClNO_4 - H]^-$ |
| 175 | OH (1) | Br (4) | 4 | 339 $[C_{14}H_{14}BrNO_4 - H]^-$ |
| 176 | OH (1) | CH₃ (3) | 4 | 276 $[C_{15}H_{17}N_2O_4 + H]^+$ |
| 177 | OH (1) | CH₃ (4) | 4 | 276 $[C_{15}H_{17}N_2O_4 + H]^+$ |
| 178 | OH (1) | N(CH₃)₂ (3) | 4 | 303 $[C_{16}H_{20}N_2O_4 - H]^-$ |
| 179 | OH (1) | NHSO₂CH₃ (4) | 4 | 355 $[C_{15}H_{18}N_2O_6S + H]^+$ |
| 180 | OH (1) | NHSO₂CH₃ (3) | 4 | 355 $[C_{15}H_{18}N_2O_6S + H]^+$ |

Preparation 2

(6-Bromohexyloxy)-tert-butyldimethylsilane

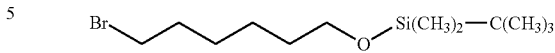

Add a solution of tert-butyldimethylsilyl chloride (5.0 g, 33.1 mmol) in dimethylformamide (DMF) (70 mL) dropwise over 15 minutes to a solution of 6-bromohexanol (5.0 g, 27.6 mmol) and imidazole (4.7 g, 69 mmol) in DMF (80 mL) at 0° C. under nitrogen protection and stir the mixture for another 3.5 hours. Dilute the mixture with water (400 mL) and extract with diethyl ether (3×150 mL). Dry the combined organic extracts over sodium sulfate and remove the solvent under reduced pressure. Purify the crude product by flash column chromatography on silica gel, eluting with ethyl acetate/hexanes (1:19), to provide (6-bromohexyloxy)-tert-butyldimethylsilane (8.05 g, 98%).

Preparation 3

7-[4-(4-Methoxyphenyl)thiazol-2-yl]heptanal

Add a solution of thioacetamide (2.65 g, 34.9 mmol) in acetone (100 mL) dropwise to a solution of 2-bromo-4'-methoxyacetonephenone (8.0 g, 34.9 mmol) in acetone (100 mL) at room temperature under nitrogen. Stir the mixture for 12 hours. Collect the solids by filtration and wash with cold acetone (30 mL) to provide thioacetimidic acid 2-(4-methoxyphenyl)-2-oxoethyl ester hydrobromide (10.25 g, 96%).

Heat a mixture of thioacetimidic acid 2-(4-methoxyphenyl)-2-oxoethyl ester hydrobromide (10.0 g, 32.9 mmol) and zinc (II) chloride (4.50 g, 33.0 mmol) in methanol (80 mL) at reflux under nitrogen protection for 6.5 hours. Cool the mixture, slowly dilute with saturated NaHCO₃ (300 mL), and extract with methylene chloride (400 mL×2). Dry the combined organic extracts over sodium sulfate and remove the solvent under reduced pressure. Purify the crude product by flash column chromatography on silica gel, eluting with hexanes/ethyl acetate (9:1), to provide 4-(4-methoxyphenyl)-2-methylthiazole (6.24 g, 92%): APCI mass spectrum m/z 206 $[C_{11}H_{11}NOS+H]^+$.

Add a solution of tert-butyllithium (26.35 mmol, 15.5 mL, 1.7 M in hexanes) dropwise to a solution of 4-(4-methoxyphenyl)-2-methylthiazole (6.15 g, 29.9 mmol) in degassed anhydrous tetrahydrofuran (THF) (100 mL) at −78° C. under nitrogen and stir the solution for 45 minutes. To this solution, add a solution of (6-bromohexyloxy)-tert-butyldimethylsilane (7.20 g, 24.4 mmol) over 5 min and stir the mixture for 2 hours. Warm the mixture to 0° C., dilute with NH₄Cl (200 mL) and brine (250 mL) and extract with methylene chloride (3×150 mL). Dry the combined organic extracts over magnesium sulfate and remove the solvent under reduced pressure. Purify the crude product by flash column chromatography on silica gel, eluting with hexanes/ethyl acetate (5:1), to provide 2-[7-(tert-butyldimethylsilanyloxy)heptyl]-4-(4-methoxyphenyl)thiazole (6.27 g, 50%).

Add a solution of 1 N tetra-n-butylammonium fluoride (25.0 mmol, 25 mL, 1 M solution in THF) dropwise over 10 minutes to a solution of 2-[7-(tert-butyldimethylsilanyloxy)heptyl]-4-(4-methoxyphenyl)thiazole (6.27 g, 14.9 mmol) in anhydrous THF (50 mL) at 0° C. under nitrogen and stir the mixture for 30 minutes at 0° C. and then stir at room temperature for 3 hours. Dilute the mixture with brine (150 mL) and extract with ethyl acetate (100 mL×3). Dry the combined organic extracts over magnesium sulfate and remove the solvent under reduced pressure. Purify the crude product by flash column chromatography on silica gel, eluting with ethyl acetate/hexanes (1:2), to give 7-[4-(4-methoxyphenyl)thiazol-2-yl]heptan-1-ol (4.07 g, 89%): APCI mass spectrum m/z 306 $[C_{17}H_{23}NO_2S+H]^+$.

Add anhydrous dimethyl sulfoxide (0.25 mL, 3.52 mmol) dropwise over 2 minutes to a solution of oxalyl chloride (393 mg, 3.10 mmol) in methylene chloride (10 mL) at −78° C. under nitrogen and stir the mixture for 20 minutes. Add a solution of 7-[4-(4-methoxyphenyl)thiazol-2-yl]heptan-1-ol (0.609 g, 1.99 mmol) in methylene chloride (10 mL) dropwise in 5 minutes and then stir the mixture for 30 minutes. To this mixture, add triethylamine (1.0 mL, 7.2 mmol), stir and warm the reaction mixture to room temperature for 40 minutes. Dilute the mixture with ethyl acetate (100 mL), wash with brine (3×30 mL), dry over sodium sulfate and remove the solvent under reduced pressure to provide 7-[4-(4-methoxyphenyl)thiazol-2-yl]heptanal (0.6 g, 99%): APCI mass spectrum m/z 304 $[C_{17}H_{21}NO_2S+H]^+$.

Example 31

7-[4-(4-Methoxyphenyl)thiazol-2-yl]heptanoic Acid

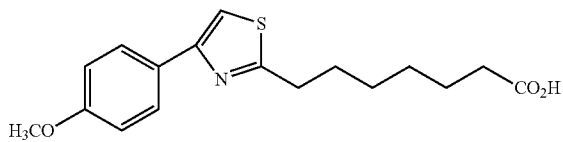 [SMILES: COc1ccc(-c2csc(CCCCCCC(=O)O)n2)cc1]

Add 2-methyl-2-butene (7.0 mL) and sodium hypochlorite (2.51 g, 27.75 mmol) to a solution of 7-[4-(4-methoxyphenyl) thiazol-2-yl]heptanal (4.02 g, 13.25 mmol) and potassium dihydrogen phosphate (3.10 g, 22.78 mmol) in tert-butanol (60 mL) and water (12 mL) at room temperature. Stir the mixture for 40 minutes, dilute with ethyl acetate (500 mL) and wash with brine (3×200 mL). Dry the combined organic extracts over sodium sulfate and remove the solvent under reduced pressure. Purify the residue by flash column chromatography on silica gel, eluting with methanol/methylene chloride (1:19), and triturate the residue with hexanes/methylene chloride to afford 7-[4-(4-methoxyphenyl)thiazol-2-yl]heptanoic acid (3.91 g, 88%): APCI MS m/z 320 $[C_{17}H_{21}NO_3S+H]^+$.

Prepare Examples 32 and 33, compounds of formula II(b) listed in Table 2 below, by the same process as in the preparation of Example 31.

TABLE 2

Compounds of formula II(b)

| Example | $R^1$ | n | mass spectrum m/z |
|---------|-------|---|-------------------|
| 32 | OCH₃ | 6 | 318 $[C_{17}H_{21}NO_3S − H]^-$ |
| 33 | OH | 6 | 304 $[C_{16}H_{19}NO_3S − H]^-$ |
| 181 | OH | 4 | 276 $[C_{14}H_{15}NO_3S − H]^-$ |

Preparation 4

7-(2-Oxo-2-phenylethylcarbamoyl)heptanoic Acid Methyl Ester

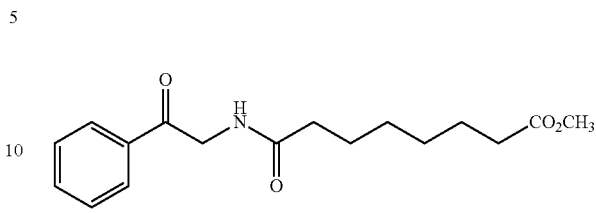

Add 1-(3-dimethylaminopropyl)-3-ethylcarbodiimide (EDC) (8.5 g, 44.3 mL) to a solution of 2-amino-1-phenylethanol (5.0 g, 36.4 mmol), suberic acid monomethyl ester (6.85 g, 36.4 mmol) and 1-hydroxybenzotriazole (HOBt, 5.0 g, 37.0 mmol) in THF (200 mL) at room temperature under nitrogen. Stir the mixture for 12 hours. Dilute the mixture with ethyl acetate (600 mL), wash with 1N HCl (2×150 mL), brine (2×150 mL), NaHCO₃ (2×150 mL) and brine (150 mL) solutions and dry over sodium sulfate. Remove the solvent under reduced pressure to provide 7-(2-hydroxy-2-phenylethylcarbamoyl)heptanoic acid methyl ester (10.3 g, 91%), which is used in the following step without purification.

Add Dess-Martin periodinane (16.5 g, 38.7 mmol) to a solution of 7-(2-hydroxy-2-phenylethylcarbamoyl)heptanoic acid methyl ester (10.2 g, 33.3 mmol) in methylene chloride (360 mL) at 0° C. under nitrogen, stir and warm the mixture to room temperature for 4 hours. Filter the mixture through Celite, wash with ethyl acetate (3×100 mL) and remove the solvent under reduced pressure. Purify the residue by flash column chromatography on silica gel, eluting with hexane/ethyl acetate (60:40), to provide 7-(2-oxo-2-phenylethylcarbamoyl)heptanoic acid methyl ester (7.33 g, 72%).

Example 34

7-(5-Phenyloxazol-2-yl)heptanoic Acid Methyl Ester

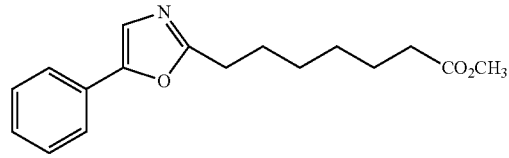 [SMILES: COC(=O)CCCCCCc1ncc(-c2ccccc2)o1]

Add a solution of 7-(2-oxo-2-phenylethylcarbamoyl)heptanoic acid methyl ester (7.05 g, 23.1 mmol) and carbon tetrabromide (11.3 g, 34.3 mmol) in methylene chloride over 40 minutes to a mixture of triphenylphosphine (9.0 g, 34.3 mmol) and DMAP (5.51 g, 45.1 mmol) in methylene chloride (500 mL) at room temperature under nitrogen. Stir the mixture for 30 minutes and add additional triphenylphosphine (2.6 g, 9.92 mmol) and carbon tetrabromide (3.35 g, 10.1 mmol). Stir the mixture for an additional 20 minutes, filter through Celite and wash with ethyl acetate (3×100 mL). Remove the solvent under reduced pressure and purify the residue by flash column chromatography on silica gel, eluting with hexanes/ethyl acetate (70:30), to provide 7-(5-phenyloxazol-2-yl)heptanoic acid methyl ester (2.75 g, 41%).

Example 35

7-(5-Phenyloxazol-2-yl)heptanoic Acid

Add a solution of sodium hydroxide (1.80 g, 45.0 mmol) in water (30 mL) to a solution of 7-(5-phenyloxazol-2-yl)heptanoic acid methyl ester (9.0 g, 31.3 mmol) in methanol (30 mL) at room temperature and stir the mixture for 4 hours. Adjust the pH of the mixture to 2 with 1 N HCl and extract with ethyl acetate (500 mL). Wash the combined organic layers with water (3×100 mL), dry over sodium sulfate and remove the solvent under reduced pressure. Crystallize the residue from ethyl acetate/hexanes to afford 7-(5-phenyloxazol-2-yl)heptanoic acid (7.3 g, 85%): APCI mass spectrum m/z 272 [$C_{16}H_{19}NO_3$—H]⁻.

Prepare Examples 36-41, compounds of formula II(c) listed in Table 3 below, by the same process as in the preparation of Example 35.

TABLE 3

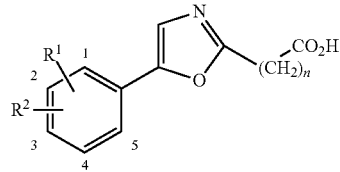

Compounds of formula II(c)

| Example | R¹ (position on ring) | R² (position on ring) | n | mass spectrum m/z |
|---|---|---|---|---|
| 36 | OCH₃ (1) | H | 6 | 302 [$C_{17}H_{21}NO_4$ – H]⁻ |
| 37 | OH (1) | Cl (4) | 6 | 321 [$C_{16}H_{18}ClNO_4$ – H]⁻ |
| 38 | OCH₃ (1) | OCH₃ (4) | 6 | 332 [$C_{18}H_{23}NO_5$ – H]⁻ |
| 39 | OH (1) | H | 4 | 260 [$C_{14}H_{15}NO_4$ – H]⁻ |
| 40 | OCH₃ (1) | H | 6 | 302 [$C_{17}H_{21}NO_4$ – H]⁻ |
| 41 | OH (1) | H | 6 | 288 [$C_{16}H_{19}NO_4$ – H]⁻ |

7-[2-(5-Chloro-2-isopropoxyphenyl)-2-oxoethylcarbamoyl]heptanoic Acid Methyl Ester

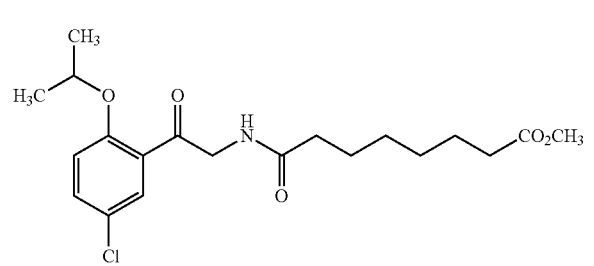 [SMILES: COC(=O)CCCCCCC(=O)NCC(=O)c1cc(Cl)ccc1OC(C)C]

Add 2-iodopropane (63.3 mL, 633 mmol) dropwise to a suspension of 1-(5-chloro-2-hydroxyphenyl)ethanone (90.0 g, 528 mmol) and potassium carbonate (109.46 g, 792 mmol) in DMF (1000 mL) at room temperature under nitrogen and heat the mixture at 80° C. for 22 hours. Cool and filter the mixture and remove the solvent reduced pressure. Dilute the residue with ethyl acetate (1 L), wash with water (300 mL) and brine (200 mL), dry over sodium sulfate, and remove the solvent under reduced pressure to afford 1-(5-chloro-2-isopropoxyphenyl)ethanone (104.78 g, 93%).

Add Copper(II) bromide (199 g, 891 mmol) portionwise to a solution of 1-(5-chloro-2-isopropoxyphenyl)ethanone (94.74 g, 446 mmol) in ethyl acetate (500 mL) and chloroform (500 mL) at room temperature under nitrogen. Heat the mixture at reflux for 4.5 hours. Cool the mixture and vacuum filter through a plug of Celite, washing with ethyl acetate (1 L). Remove the solvents under reduced pressure to provide 2-bromo-1-(5-chloro-2-isopropoxyphenyl)ethanone (128.46 g, 98%).

Add hexamethylenetetramine (36.14 g, 258 mmol) to a solution of 2-bromo-1-(5-chloro-2-isopropoxyphenyl)ethanone (75.17 g, 258 mmol) in chloroform (400 mL) at room temperature under nitrogen and stir for 2 days. Collect the solids by filtration, wash with diethyl ether, and dry overnight under reduced pressure. Suspend the solids in methanol (350 ml), cool to 0° C., and treat slowly with concentrated HCl (113 ml, 1365 mmol). Warm the mixture to room temperature and stir for 40 hours. Then heat the mixture to 55° C. for an additional 4 hours. Remove the solids by filtration, and remove the filtrate solvent under reduced pressure to provide a solid. Triturate the solid with diethyl ether. Collect the resulting material by filtration to provide 2-amino-1-(5-chloro-2-isopropoxyphenyl)ethanone hydrochloride, which is used in the next step without purification.

Add diisopropylethylamine (99 ml, 568 mmol) dropwise to a solution of EDC HCl (38.01 g, 198 mmol), HOBt (19.19 g, 142 mmol) and octanedioic acid monomethyl ester (53.44 g, 1.42 mmol) in methylene chloride (800 mL) at 0° C. under nitrogen. Warm the mixture to room temperature and stir for 1 hour. Add 2-amino-1-(5-chloro-2-isopropoxyphenyl)ethanone hydrochloride (53.44 g, 142 mmol) to the mixture and stir for 18 hours. Remove the solvent under reduced pressure, dilute the residue in ethyl acetate (300 mL), wash with water (100 mL) and brine (100 mL), and dry over magnesium sulfate. Remove the solvent under reduced pressure and purify the residue by flash column chromatography on silica gel, eluting with hexanes/ethyl acetate (4:6 to 0:10), to afford 7-[2-(5-chloro-2-isopropoxyphenyl)-2-oxoethylcarbamoyl]-heptanoic acid methyl ester (23.87 g, 23% over three steps).

Example 42

7-[5-(5-Chloro-2-isopropoxyphenyl)thiazol-2-yl]heptanoic Acid Methyl Ester

Add Lawesson's reagent (31.03 g, 77 mmol) to a solution of 7-[2-(5-chloro-2-isopropoxyphenyl)-2-oxoethylcarbamoyl]heptanoic acid methyl ester (21.80 g, 55 mmol) in THF (550 mL) at room temperature under nitrogen. Heat the mixture at reflux for 3 hours. Remove the solvent under reduced pressure and purify the residue by flash column chromatography on silica gel, eluting with ethyl acetate/hexanes (1:3), to afford 7-[5-(5-chloro-2-isopropoxyphenyl)thiazol-2-yl]heptanoic acid methyl ester (9.96 g, 46%).

Example 43

7-[5-(5-Chloro-2-hydroxyphenyl)thiazol-2-yl]heptanoic Acid Methyl Ester

Add aluminum(III) chloride (6.67 g, 50 mmol) portionwise to a solution of 7-[5-(5-chloro-2-isopropoxyphenyl)thiazol-2-yl]heptanoic acid methyl ester (9.90 g, 25 mmol) in methylene chloride (300 mL) at 0° C. under nitrogen. Slowly warm the mixture to room temperature and stir for an additional 30 minutes. Cool the mixture to 0° C., treat with saturated aqueous sodium sulfate Na$_2$SO$_4$ (150 ml), and stir for 1 hour. Remove the solvent under reduced pressure, dilute the residue with ethyl acetate (300 mL), wash with water (100 mL) and brine (100 mL), and dry over sodium sulfate. Remove the solvent under reduced pressure and purify the residue by flash column chromatography on silica gel, eluting with ethyl acetate/hexanes (1:9 to 1:1), to afford 7-[5-(5-chloro-2-hydroxyphenyl)thiazol-2-yl]heptanoic acid methyl ester (5.67 g, 64%).

Example 44

7-[5-(5-Chloro-2-hydroxy-phenyl)-thiazol-2-yl]-heptanoic acid

Add a solution of sodium hydroxide (2.60 g, 65 mmol) in water (50 mL) to a solution of 7-[5-(5-chloro-2-hydroxyphenyl)thiazol-2-yl]heptanoic acid methyl ester (5.76 g, 16 mmol) in methanol (100 mL) at 0° C. under nitrogen, warm the mixture to room temperature, and stir for a total of 1.5 hours. Remove the solvent under reduced pressure, dilute the residue with water (200 mL), cool to 0° C., and acidify to pH 1 with 1 N HCl. Collect the precipitate by filtration to afford 7-[5-(5-chloro-2-hydroxyphenyl)thiazol-2-yl]heptanoic acid (5.21 g, 95%): APCI mass spectrum m/z 338 [C$_{16}$H$_{18}$ClNO$_3$S—H]$^-$.

Prepare Examples 45-47, compounds of formula II(d) listed in Table 4 below, by the same process as in the preparation of Example 44.

TABLE 4

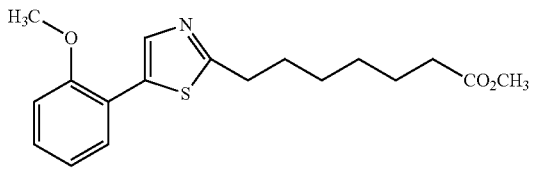

Compounds of formula II(d)

| Example | R$^1$ | n | mass spectrum m/z |
|---|---|---|---|
| 45 | OCH$_3$ | 6 | 320 [C$_{17}$H$_{21}$NO$_3$S + H]$^+$ |
| 46 | OH | 6 | 304 [C$_{16}$H$_{19}$NO$_3$S − H]$^-$ |
| 47 | OH | 4 | 276 [C$_{14}$H$_{15}$NO$_3$S − H]$^-$ |

Preparation 6

7-[2-(2-Methoxyphenyl)-2-oxoethylcarbamoyl]heptanoic Acid Methyl Ester

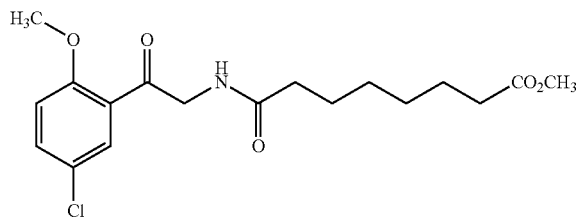 [SMILES: COC(=O)CCCCCCC(=O)NCC(=O)c1cc(Cl)ccc1OC]

Add triethylamine (8.1 g, 79.9 mmol) dropwise to a solution of 2-amino-1-(2-methoxyphenyl)ethanone hydrochloride (13.6 g, 67.4 mmol) and octanedioic acid monomethyl ester (14.0 g, 74.2 mmol) in methylene chloride (600 mL) at 0° C. under nitrogen, and then add EDC HCl (15.5 g, 81.0 mmol). Stir the mixture for 4 hours and warm to room temperature with stirring for an additional 18 hours. Dilute the mixture in ethyl acetate (1.2 L), wash sequentially with water (300 mL), 1 N HCl (300 mL), brine (300 mL), saturated sodium, bicarbonate solution (300 mL) and brine (300 mL), and dry over sodium sulfate. Remove the solvent under reduced pressure to afford 7-[2-(2-methoxyphenyl)-2-oxoethylcarbamoyl]heptanoic acid methyl ester (20.0 g, 88%), which is used in the next step without further purification.

Example 48

7-[5-(2-Methoxyphenyl)-1H-imidazol-2-yl]heptanoic Acid Methyl Ester

Heat a mixture of ammonium acetate (16.5 g, 214 mmol) and 7-[2-(2-methoxyphenyl)-2-oxoethylcarbamoyl]heptanoic acid methyl ester (14.2 g, 42.3 mmol) in acetic acid (300 mL) at reflux under nitrogen for 15 hours. Remove the solvent under reduced pressure. Dilute the residue in ethyl acetate (500 mL) and adjust to pH 8 with saturated aqueous sodium bicarbonate solution. Extract the aqueous layer with additional ethyl acetate (200 mL) and dry the combined organic extracts over sodium sulfate and remove the solvent under reduced pressure. Purify the residue by flash column chromatography on silica gel, eluting with ethyl acetate, to afford 7-[5-(2-methoxyphenyl)-1H-imidazol-2-yl]heptanoic acid methyl ester (5.86 g, 44%): APCI mass spectrum m/z 317 [C$_{18}$H$_{24}$N$_2$O$_3$+H]$^+$.

Example 49

7-[5-(2-Methoxyphenyl)-1H-imidazol-2-yl]heptanoic Acid

Add a solution of sodium hydroxide (1.85 g, 46 mmol) in water (40 mL) to a solution of 7-[5-(2-methoxyphenyl)-1H-imidazol-2-yl]heptanoic acid methyl ester (5.84 g, 18.5 mmol) in methanol (30 mL) at room temperature under nitrogen and heat the mixture at 40° C. for 4.5 hours. Cool the mixture and treat with 1 N HCl (46 mL) and heat at reflux for 30 minutes. Collect the precipitate, wash with water (3×30 mL), and dry under reduced pressure for 12 hours. Triturate the solid with methylene chloride (50 mL) at reflux for 40 min and collect by filtration to provide 7-[5-(2-methoxyphenyl)-1H-imidazol-2-yl]heptanoic acid (4.27 g, 77%). APCI mass spectrum m/z 301 [C$_{17}$H$_{22}$N$_2$O$_3$—H]$^-$.

Prepare Examples 50-55, compounds of formula II(e) listed in Table 5 below, by the same process as in the preparation of Example 49.

TABLE 5

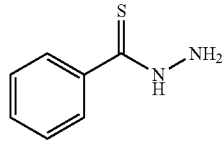

Compounds of formula II(e)

| Example | R¹ (position on ring) | n | mass spectrum m/z |
|---|---|---|---|
| 50 | H | 6 | 271 [$C_{16}H_{20}N_2O_2$ – H]⁻ |
| 51 | OCH₃ (3) | 6 | 301 [$C_{17}H_{22}N_2O_3$ – H]⁻ |
| 52 | OH (3) | 6 | 287 [$C_{16}H_{20}N_2O_3$ – H]⁻ |
| 53 | OH (1) | 6 | 287 [$C_{16}H_{20}N_2O_3$ – H]⁻ |
| 54 | OCH₃ (1) | 4 | 273 [$C_{15}H_{18}N_2O_3$ – H]⁻ |
| 55 | OH (1) | 4 | 282 [$C_{14}H_{15}N_2NaO_3$ – H]⁻ |

Preparation 7

Thiobenzoic Acid Hydrazide

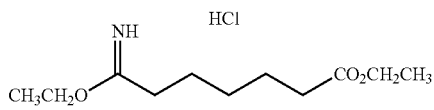

Add a solution of thiobenzoylsulfanylacetic acid (5.5 g, 26.0 mmol) in methanol (100 mL) and to a solution of thionyl chloride (52 mL) at room temperature under nitrogen and heat the mixture at reflux for 12 hours. Remove the solvent under reduced pressure, dissolve the residue in ethyl acetate (200 mL), wash with saturated NaHCO₃ (200 mL) and brine (200 mL) solutions, and dry over sodium sulfate. Remove the solvent under reduced pressure to provide thiobenzoylsulfanylacetic acid methyl ester (5.7 g, 97%).

Add a solution of thiobenzoylsulfanylacetic acid methyl ester (1.9 g, 8.4 mmol) in ethanol (30 mL) to a solution of anhydrous hydrazine (1 mL) at room temperature under nitrogen and stir for 2 hours. Then add water (20 mL) and remove the solvent under reduced pressure. Dissolve the residue in ethyl acetate (300 mL), wash with water (200 mL) and brine (200 mL), and dry over magnesium sulfate. Remove the solvent under reduced pressure to provide thiobenzoic acid hydrazide (1.2 g, 94%).

Preparation 8

7-Ethoxycarbonimidoylheptanoic Acid Ethyl Ester Hydrochloride

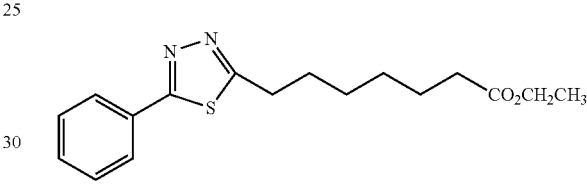

Add sodium cyanide (12.5 g, 255 mmol) and tetra-n-butylammonium iodide (10 g, 27.0 mmol) portionwise to a solution of 7-bromoheptanoic acid methyl ester (25 g, 105 mmol) in DMSO (300 mL) at room temperature under nitrogen and heat the mixture at 50° C. for 4 hours. Cool the mixture and dilute with water (200 mL) and extract with diethyl ether (2×200 mL). Dry the combined organic extracts over sodium sulfate and remove the solvent under reduced pressure to provide 7-cyanoheptanoic acid ethyl ester (18.2 g, 94%).

Bubble hydrogen chloride gas into a solution of 7-cyanoheptanoic acid ethyl ester (3.7 g, 20.0 mmol) in ethanol (24 mL, 40 mmol) and diethyl ether (100 mL) at 0° C. for 15 minutes. Remove the solvent under reduced pressure to provide 7-ethoxycarbonimidoylheptanoic acid ethyl ester (5.4 g, >99%), which is used without further purification.

Example 56

7-(5-Phenyl[1,3,4]thiadiazol)heptanoic Acid Ethyl Ester

Heat a solution of thiobenzoic hydrazide (1.2 g, 7.90 mmol) and 7-ethoxycarbonimidoylheptanoic acid ethyl ester (2.9 g, 11.0 mmol) in ethanol (35 mL) at reflux under nitrogen for 3 hours. Remove the solvent under reduced pressure. Dissolve the residue in ethyl acetate (200 mL), wash with water (200 mL) and brine (200 mL), and dry over sodium sulfate. Remove the solvent under reduced pressure and purify the residue by flash column chromatography on silica gel, eluting with hexane/ethyl acetate (4:1), to provide 7-(5-phenyl[1,3,4]thiadiazol)heptanoic acid ethyl ester (1.15 g, 45%).

Example 57

7-(5-Phenyl[1,3,4]thiadiazol-2-yl)heptanoic Acid

Add a solution of potassium hydroxide (1.2 g 23 mmol) in water (50 mL) to a solution of 7-(5-phenyl-[1,3,4]thiadiazol)heptanoic acid ethyl ester (3.4 g, 11 mmol) in THF (30 mL) and methanol (30 mL) at room temperature under nitrogen and heat the mixture at reflux for 3 hours. Remove the solvent under reduced pressure, dilute the residue with water (200 mL) and wash with ethyl acetate (200 mL). Adjust the pH of the aqueous layer to 3 with concentrated HCl and extract with ethyl acetate (3×200 mL). Wash the combined organic extracts with brine (200 mL), dry over sodium sulfate and remove the solvent under reduced pressure to afford 7-(5-phenyl[1,3,4]thiadiazol-2-yl)heptanoic acid (2.9 g, 93%). APCI mass spectrum m/z 289 [$C_{15}H_{18}N_2O_2S$—H]⁻.

Prepare Examples 58-61, compounds of formula II(f) listed in Table 6 below, by the same process as in the preparation of Example 57.

TABLE 6

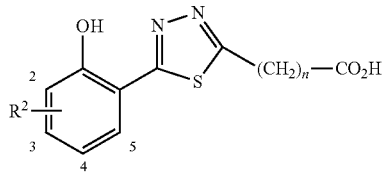

Compounds of formula II(f)

| Example | $R^2$ (position on ring) | n | mass spectrum m/z |
|---|---|---|---|
| 58 | $OCH_3$ (3) | 6 | 335 $[C_{16}H_{20}N_2O_4S - H]^-$ |
| 59 | H | 6 | 305 $[C_{15}H_{18}N_2O_3S - H]^-$ |
| 60 | Cl (4) | 6 | 341 $[C_{15}H_{17}ClN_2O_3S + H]^+$ |
| 61 | H | 4 | 277 $[C_{13}H_{14}N_2O_3S - H]^-$ |

Preparation 9

8-Amino-8-(benzoylhydrazono)octanoic Acid Ethyl Ester

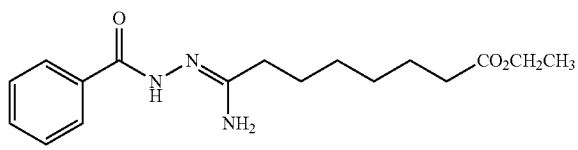

Add triethylamine (5.6 mL, 40 mmol) to a solution of 7-ethoxycarbonimidoylheptanoic acid ethyl ester (11.0 g, 41 mmol) and benzoic acid hydrazide (5.5 g, 40 mmol) in ethanol (110 mL) at room temperature under nitrogen and stir the mixture for 12 hours. Remove the solvent under reduced pressure, dissolve the residue in ethyl acetate (200 mL), wash with saturated $NaHCO_3$ (200 mL) and brine (200 mL) solutions, and dry over sodium sulfate. Remove the solvent under reduced pressure to provide 8-amino-8-(benzoylhydrazono)octanoic acid ethyl ester (8.3 g, 64%).

Example 62

7-(5-Phenyl-4H-[1,3,4]triazol-3-yl)heptanoic Acid Ethyl Ester

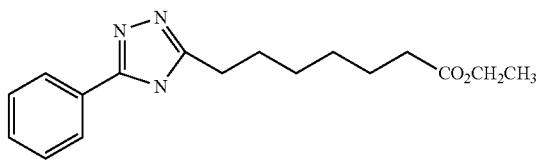

Heat a solution of 8-amino-8-(benzoylhydrazono)octanoic acid ethyl ester (4.2 g, 26 mmol) in o-xylene (400 mL) at reflux under nitrogen for 5 hours and then remove the solvent under reduced pressure. Dilute the residue with ethyl acetate (500 mL), wash with saturated $NaHCO_3$ (200 mL) and brine (200 mL) solutions and dry over sodium sulfate. Remove the solvent under reduced pressure and purify the residue by flash column chromatography on silica gel, eluting with methanol/methylene chloride (1:9), to provide 7-(5-phenyl-4H-[1,3,4]triazol-3-yl)heptanoic acid ethyl ester (2.2 g, 58%).

Example 63

7-(5-Phenyl-4H-[1,3,4]triazol-3-yl)-heptanoic acid

Add a solution of potassium hydroxide (1.8 g, 32 mmol) in water (70 mL) to a solution of 7-(5-phenyl-4H-[1,3,4]triazol-3-yl)heptanoic acid ethyl ester (4.9 g, 16 mmol) in THF (50 mL) and methanol (50 mL) at room temperature under nitrogen and heat the mixture at reflux for 3 hours. Remove the solvent under reduced pressure, dilute the residue with water (200 mL) and wash with ethyl acetate (200 mL). Adjust the pH of the aqueous layer to 3 with concentrated HCl and extract with ethyl acetate (3×200 mL). Wash the combined organic extracts with brine (200 mL), dry over sodium sulfate and remove the solvent under reduced pressure to afford 7-(5-phenyl-4H-[1,3,4]triazol-3-yl)heptanoic acid (4.4 g, 99%). APCI mass spectrum m/z 273 $[C_{15}H_{19}N_3O_2]^-$.

Prepare Examples 64-39, compounds of formula II(g) listed in Table 7 below, by the same process as in the preparation of Example 63.

TABLE 7

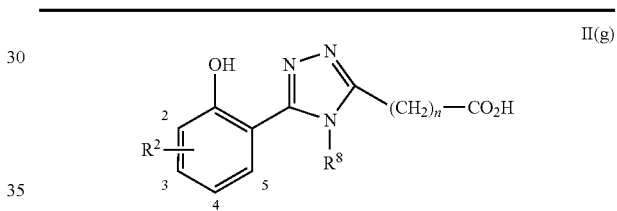

Compounds of formula II(g)

| Example | $R^2$ (position on ring) | $R^8$ | n | mass spectrum m/z |
|---|---|---|---|---|
| 64 | $OCH_3$ (3) | H | 6 | 319 $[C_{16}H_{21}N_3O_4 - H]^-$ |
| 65 | H | H | 6 | 289 $[C_{15}H_{19}N_3O_3 - H]^-$ |
| 66 | Cl (4) | H | 6 | 323 $[C_{15}H_{18}ClN_3O_3 - H]^-$ |
| 67 | H | H | 4 | 261 $[C_{13}H_{15}N_3O_3]^-$ |
| 68 | H | $CH_3$ | 4 | 277 $[C_{14}H_{17}N_3O_3]^-$ |

Preparation 10

N-Hydroxy-2-methoxybenzamidine

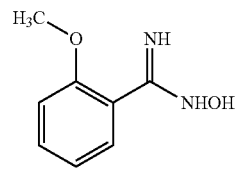

Add potassium hydroxide (30.3 g, 225 mmol) to a solution of 2-methoxybenzonitrile (25.0 g, 187 mmol) and hydroxylamine hydrochloride (15.77 g, 225 mmol) in ethanol (500 mL) at room temperature under nitrogen and heat the mixture at reflux for 12 hours. Remove the solvent under reduced pressure, triturate the residue with ethyl acetate/hexanes (1:9, 300 mL) and collect by vacuum filtration to provide N-hydroxy-2-methoxybenzamidine (24.0 g, 91%).

Example 69

5-[3-(2-Methoxyphenyl)-[1,2,4]oxadiazol-5-yl]pentanoic Acid Methyl Ester

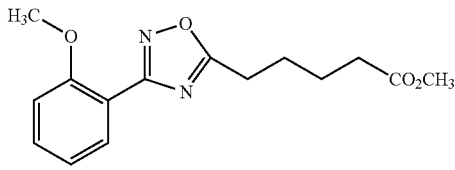 [SMILES: COC(=O)CCCCc1nc(-c2ccccc2OC)no1]

Add 5-chlorocarbonylpentanoic acid methyl ester (15.30 g, 86 mmol) to a solution of N-hydroxy-2-methoxybenzamidine (12.0 g, 71 mmol) in pyridine (40 mL) and under nitrogen at a rate to keep the mixture at a gentle reflux. Then, heat the mixture at reflux for 4 hours. Dilute the mixture with water (300 mL) and extract with methylene chloride (3×200 mL). Wash the combined organic extracts with brine (100 mL), dry over sodium sulfate and remove the solvent under reduced pressure. Purify the residue by flash column chromatography on silica gel, eluting with ethyl acetate/hexanes (1:19), to afford 5-[3-(2-methoxyphenyl)-[1,2,4]oxadiazol-5-yl]pentanoic acid methyl ester (12.8 g, 55%).

Example 70

5-[3-(2-Methoxyphenyl)-[1,2,4]oxadiazol-5-yl]pentanoic Acid

Add 2 N sodium hydroxide (20 mL) to a solution of 5-[3-(2-methoxyphenyl)-[1,2,4]oxadiazol-5-yl]pentanoic acid methyl ester (4.00 g, 13 mmol) in methanol (100 mL) at room temperature under nitrogen and stir the mixture for 3 hours. Remove the solvent under reduced pressure, dilute the residue with water (200 mL) and wash with diethyl ether (200 mL). Adjust the aqueous layer to pH 1 with 2 N HCl and collect the solids by vacuum filtration to afford 5-[3-(2-methoxyphenyl)-[1,2,4]oxadiazol-5-yl]pentanoic acid (3.65 g, 99%). APCI mass spectrum m/z 275 $[C_{14}H_{16}N_2O_4—H]^-$.

Prepare Examples 71-73, compounds of formula II(h) listed in Table 8 below, by the same process as in the preparation of Example 40.

TABLE 8

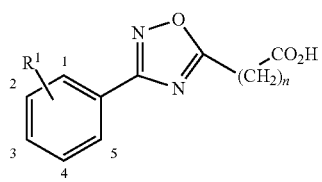

Compounds of formula II(h)

| Example | $R^1$ (position on ring) | N | mass spectrum m/z |
|---|---|---|---|
| 71 | OH (1) | 4 | 261 $[C_{13}H_{14}N_2O_4 - H]^-$ |
| 72 | $CH_3$ (2) | 7 | 301 $[C_{17}H_{22}N_2O_3 - H]^-$ |
| 73 | $CF_3$ (3) | 7 | 355 $[C_{17}H_{19}F_3N_2O_3 - H]^-$ |

Preparation 11

4-(2-Isopropoxy-phenyl)-1H-imidazole

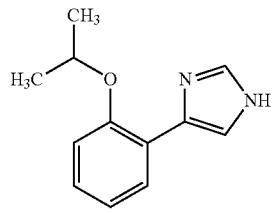

Add tetrakis(triphenylphosphine)palladium(0) (500 mg) to a degassed suspension of 4-bromo-1H-imidazole (5.0 g, 34 mmol) and 2-isopropoxyphenyl boronic acid (9.19 g, 51 mmol) in dioxane (250 mL) and 2 M sodium carbonate solution (10.81 g, 102 mmol) at room temperature under nitrogen and heat the mixture at reflux for 21 hours. Remove the solvent under reduced pressure, dilute the residue with ethyl acetate (500 mL) and filter through a plug of Celite. Dry the filtrate over sodium sulfate, treat with silica gel (20 g) and remove the solvent under reduced pressure. Purify the residue by flash column chromatography on silica gel, eluting with ethyl acetate, to afford crude 4-(2-isopropoxyphenyl)-1H-imidazole (5.01 g, 73%) which is used without further purification in the next step.

Example 74

8-[4-(2-Isopropoxyphenyl)imidazol-1-yl]octanoic Acid Methyl Ester

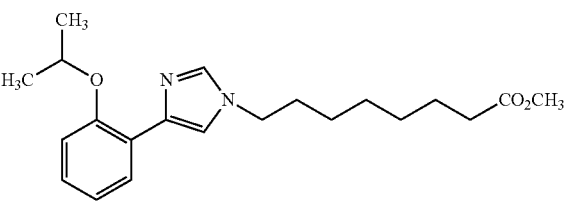 [SMILES: COC(=O)CCCCCCCn1cnc(-c2ccccc2OC(C)C)c1]

Add sodium hydride (1.82 g, 38 mmol) to a suspension of 4-(2-isopropoxyphenyl)-1H-imidazole (5.01 g, 25 mmol) in THF (125 mL) at 0° C. under nitrogen, and warm the mixture to room temperature and stir for 1 hour. Cool the mixture to 0° C. and add 8-bromooctanoic acid methyl ester (5.98 g, 25 mmol) and tetra-n-butylammonium iodide (0.55 g, 1.5 mmol) and warm the mixture to room temperature to stir for 8 hours. Dilute the mixture with water (20 mL) and remove the solvent under reduced pressure. Dilute the residue with ethyl acetate (300 mL), wash with water (100 mL) and brine (100 mL), dry over sodium sulfate, and remove the solvent under reduced pressure to provide 8-[4-(2-isopropoxyphenyl)imidazol-1-yl]octanoic acid methyl ester (5.16 g, 57%), which is used in the next step without further purification.

Example 75

8-[4-(2-Hydroxyphenyl)imidazol-1-yl]octanoic Acid Methyl Ester

Add aluminum(III) chloride (3.84 g, 29 mmol) to a suspension of 8-[4-(2-isopropoxyphenyl)imidazol-1-yl]octanoic acid methyl ester (5.16 g, 14 mmol) in methylene chloride (150 mL) at 0° C. under nitrogen. Warm the mixture to room temperature and stir for 6 hours. Dilute the mixture with saturated aqueous sodium sulfate (50 mL) and remove the solvent under reduced pressure. Dilute the residue with ethyl acetate (300 mL), wash with brine (100 mL), dry over sodium sulfate, and remove the solvent under reduced pressure. Purify the residue by flash column chromatography on silica gel, eluting with ethyl acetate/hexanes (2:8 to 3:7), to provide 8-[4-(2-hydroxyphenyl)imidazol-1-yl]octanoic acid methyl ester (2.63 g, 57%).

Example 76

8-[4-(2-Hydroxyphenyl)imidazol-1-yl]octanoic Acid

Add sodium hydroxide (1.32 g, 33 mmol) in water (20 mL) to a suspension of 8-[4-(2-hydroxyphenyl)imidazol-1-yl]octanoic acid methyl ester (2.60 g, 8 mmol) in methanol (50 mL) at 0° C. under nitrogen and warm the mixture to room temperature and stir for 8 hours. Remove the solvent under reduced pressure, dilute the residue with water (200 mL), cool to 0° C., and acidify to pH 1 with 1 N HCl. Collect the precipitate to provide 8-[4-(2-hydroxyphenyl)imidazol-1-yl] octanoic acid (1.70 g, 68%). APCI mass spectrum m/z 301 $[C_{17}H_{22}N_2O_3$—H$]^-$.

Prepare Examples 77 and 78, compounds of formula II(i) listed in Table 9 below, by the same process as in the preparation of Example 76.

TABLE 9

II(i)

Compounds of formula II(i)

| Example | R$^1$ | n | mass spectrum m/z |
|---------|-------|---|-------------------|
| 77 | H | 7 | 285 $[C_{17}H_{22}N_2O_2 - H]^-$ |
| 78 | OH | 4 | 259 $[C_{14}H_{16}N_2O_3 - H]^-$ |

Example 79

7-[3-(2-Hydroxyphenyl)pyrazol-1-yl]heptanoic Acid Ethyl Ester

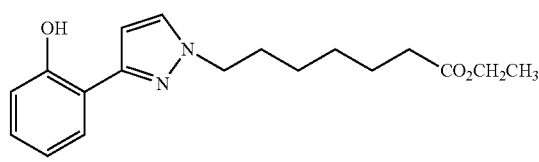

Add sodium hydride (1.50 g, 31 mmol, 60% suspension in mineral oil) to a suspension of 2-(1H-pyrazol-3-yl)phenol (5.0 g, 31 mmol) and 7-bromoheptanoic acid ethyl ester (7.4 g, 31 mmol) in DMF (75 mL) at room temperature under nitrogen and heat the mixture at 75° C. for 16 hours. Remove the solvent under reduced pressure, dilute the residue with ethyl acetate (300 mL), wash with water (100 mL), and dry over sodium sulfate. Remove the solvent under reduced pressure and purify the residue by flash column chromatography on silica gel, eluting with hexanes/ethyl acetate (9:1), to provide 7-[3-(2-hydroxyphenyl)pyrazol-1-yl]heptanoic acid ethyl ester (4.73 g, 48%).

Example 80

7-[3-(2-Methoxyphenyl)pyrazol-1-yl]heptanoic Acid Ethyl Ester

Add sodium hydride (900 mg, 18 mmol, 60% suspension in mineral oil) to a suspension of 7-[3-(2-hydroxyphenyl) pyrazol-1-yl]heptanoic acid ethyl ester (4.73 g, 15 mmol) and iodomethane (1.1 mL, 18 mmol) in THF (70 mL) at 0° C. under nitrogen and warm the mixture to room temperature to stir for 12 hours. Remove the solvent under reduced pressure, dilute the residue with ethyl acetate (150 mL), wash with water (100 mL), and dry over sodium sulfate. Remove the solvent under reduced pressure and purify the residue by flash column chromatography on silica gel, eluting with hexanes/ethyl acetate (9:1), to provide 7-[3-(2-Methoxyphenyl)pyrazol-1-yl]heptanoic acid ethyl ester (3.75 g, 76%).

Example 81

7-[3-(2-Methoxyphenyl)pyrazol-1-yl]heptanoic Acid

Add 2 N sodium hydroxide (20 mL) to a solution of 7-[3-(2-Methoxyphenyl)pyrazol-1-yl]heptanoic acid ethyl ester (3.75 g, 11.4 mmol) in methanol (40 mL) at room temperature under nitrogen and stir the mixture for 8 hours. Remove the solvent under reduced pressure, dilute the residue with water (100 mL), acidify to pH 3 with 1 N HCl, extract with ethyl acetate (200 mL), and dry over sodium sulfate. Remove the solvent under reduced pressure to provide 7-[3-(2-methoxyphenyl)pyrazol-1-yl]heptanoic acid (3.06 g, 89%). APCI mass spectrum m/z 303 $[C_{17}H_{22}N_2O_3+H]^+$.

Prepare Examples 82-87, compounds of formula II(j) listed in Table 10 below, by the same process as in the preparation of Example 81.

TABLE 10

II(j)

Compounds of formula II(j)

| Example | R$^1$ | R$^2$ (position on ring) | n | mass spectrum m/z |
|---------|-------|--------------------------|---|-------------------|
| 82 | OH | H | 6 | 289 $[C_{16}H_{20}N_2O_3 + H]^+$ |
| 83 | OH | Cl (4) | 6 | 321 $[C_{16}H_{19}ClN_2O_3 - H]^-$ |
| 84 | OH | Br (4) | 6 | 366 $[C_{16}H_{19}BrN_2O_3 - H]^-$ |
| 85 | OCH3 | H | 4 | 273 $[C_{15}H_{18}N_2O_3 - H]^-$ |
| 86 | OH | H | 4 | 259 $[C_{14}H_{16}N_2O_3 - H]^-$ |
| 87 | OH | OCH3 (3) | 4 | 291 $[C_{15}H_{18}N_2O_4 + H]^+$ |

Example 88

8-(2-Phenylimidazol-1-yl)octanoic Acid Methyl Ester

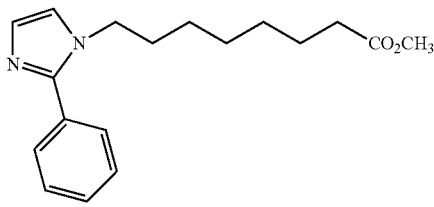 [SMILES: COC(=O)CCCCCCCn1ccnc1-c1ccccc1]

Add sodium hydride (1.3 g, 42 mmol) to a mixture of 2-phenyl-1H-imidazole (5.0 g, 35 mmol), 8-bromooctanoic acid methyl ester (8.22 g, 35 mmol), potassium carbonate (5.75 g, 42 mmol), and tetra-n-butylammonium iodide (0.77 g, 2 mmol) in DMF (250 mL) at 0° C. under nitrogen. Heat the mixture to 75° C. and stir for 21 hours. Remove the solvent under reduced pressure, dissolve the residue in chloroform (200 mL), wash with water (100 mL) and brine (100 mL), and dry over sodium sulfate. Remove the solvent under reduced pressure and purify the residue by flash column chromatography on silica gel, eluting with methanol/methylene chloride (1:9), to afford 8-(2-phenylimidazol-1-yl)octanoic acid methyl ester (4.90 g, 47%).

Example 89

8-(2-Phenylimidazol-1-yl)octanoic Acid

Add sodium hydroxide (6.0 g, 150 mmol) in water (50 mL) to a suspension of 8-(2-phenylimidazol-1-yl)octanoic acid methyl ester (7.60 g, 25 mmol) in methanol (100 mL) at 0° C. under nitrogen. Warm the mixture to room temperature and stir for a total of 8 hours. Remove the solvent under reduced pressure, dilute the residue with water (300 mL), cool to 0° C., and acidify to pH 1 with 1 N HCl. Collect the precipitate and triturate with hexanes to afford 8-(2-phenylimidazol-1-yl) octanoic acid (4.22 g, 52%). APCI mass spectrum m/z 285 $[C_{17}H_{22}N_2O_2—H]^-$.

Preparation 12

2-Methoxy-N-hydroxybenzenecarboxyimidoyl Chloride

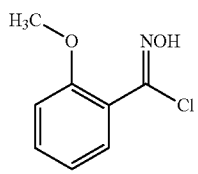

Add sodium hydroxide (8.50 g, 220 mmol) in water (150 mL) to a solution of o-anisaldehyde (25.0 g, 180 mmol) and hydroxylamine hydrochloride (15.4 g, 220 mmol) in ethanol (150 mL) and water (150 mL) at room temperature and stir the mixture for 3 hours. Acidify the mixture to pH 6 with 1 N HCl solution and collect the solids by vacuum filtration to provide 2-methoxybenzaldehyde oxime (32.0 g, 99%).

Add N-Chlorosuccinimide (8.30 g, 65 mmol) portionwise to a solution of 2-methoxybenzaldehyde oxime (10.0 g, 65 mmol) in DMF (100 mL) at room temperature under nitrogen. Heat the mixture at 50° C. for 5 hours. Pour the mixture into ice water (300 mL) collect the solids by vacuum filtration to provide 2-methoxy-N-hydroxybenzenecarboxyimidoyl chloride (9.80 g, 81%).

Example 90

7-[3-(2-Methoxyphenyl)isoxazol-5-yl]heptanoic Acid Methyl Ester

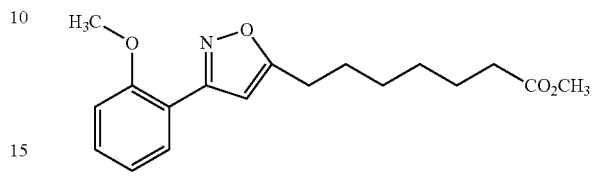

Add triethylamine (8.08 g, 80 mmol) to a solution of 2-methoxy-N-hydroxybenzenecarboxyimidoyl chloride (8.0 g, 40 mmol) and methyl 7-oxtynoate (10.50 g, 50 mmol) in THF (100 mL) at room temperature and stir the mixture for 24 hours. Dilute the mixture with water (500 mL) and extract with ethyl acetate (3×200 mL). Wash the combined organic extracts with water (100 mL) and brine (100 mL) and dry over sodium sulfate. Remove the solvent under reduced pressure and purify the residue by flash column chromatography on silica gel, eluting with ethyl acetate/hexanes (1:9), to afford 7-[3-(2-methoxyphenyl)isoxazol-5-yl]heptanoic acid methyl ester (7.80 g, 55%).

Example 91

7-[3-(2-Methoxyphenyl)isoxazol-5-yl]heptanoic Acid

Add 2 N sodium hydroxide (15 mL) to a solution of 7-[3-(2-methoxyphenyl)isoxazol-5-yl]heptanoic acid methyl ester (2.89 g, 8 mmol) in methanol (50 mL) at room temperature under nitrogen and stir for 3 hours. Remove the solvent under reduced pressure, dilute the residue with water (100 mL), and wash with methyl tert-butyl ether (100 mL). Acidify the mixture to pH 1 with 1 N HCl and extract with ethyl acetate (3×100 mL). Wash the combined organic extracts with water (100 mL) and brine (100), dry over sodium sulfate, and remove the solvent under reduced pressure to provide 7-[3-(2-methoxyphenyl)isoxazol-5-yl]heptanoic acid (2.41 g, 98%): APCI mass spectrum m/z 302 $[C_{17}H_{21}INO_4—H]^-$.

Prepare Examples 92-98, compounds of formula II(k) listed in Table 11 below, by the same process as in the preparation of Example 91.

TABLE 11

II(k)

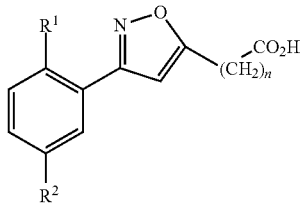

Compounds of formula II(k)

| Example | R¹ (position on ring) | R² (position on ring) | n | mass spectrum m/z |
|---|---|---|---|---|
| 92 | OH | H | 4 | 260 $[C_{14}H_{15}NO_4 - H]^-$ |
| 93 | OCH₃ | Cl | 4 | 309 $[C_{15}H_{16}ClNO_4 - H]^-$ |
| 94 | OH | Cl | 4 | 294 $[C_{14}H_{14}ClNO_4 - H]^-$ |

TABLE 11-continued

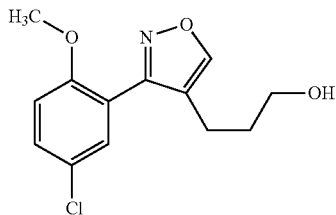 [SMILES: COc1ccc(Cl)cc1-c1nocc1CCCO]

Compounds of formula II(k)

| Example | R[1] (position on ring) | R[2] (position on ring) | n | mass spectrum m/z |
|---|---|---|---|---|
| 95 | OH | Cl | 6 | 322 [$C_{16}H_{18}ClNO_4 - H$]$^-$ |
| 96 | OCH$_3$ | Cl | 6 | 337 [$C_{17}H_{20}ClNO_4 - H$]$^-$ |
| 97 | OH | H | 6 | 288 [$C_{16}H_{19}NO_4 - H$]$^-$ |
| 98 | OH | H | 4 | 260 [$C_{14}H_{15}NO_4 - H$]$^-$ |

Preparation 13

3-[3-(5-Chloro-2-methoxyphenyl)isoxazol-4-yl]propan-1-ol

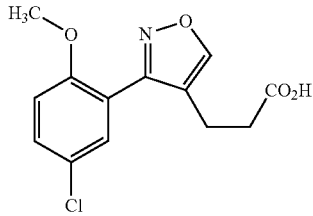 [SMILES: COc1ccc(Cl)cc1-c1nocc1CCC(=O)O]

Add N-Chlorosuccinimide (8.6 g, 65 mmol) portionwise to a solution of anisaldehyde oxime (10.0 g, 65 mmol) in DMF (250 mL) at room temperature under nitrogen and heat at 50° C. for 6 hours. Pour the mixture into ice water (800 mL) and collect the solids by vacuum filtration to provide 5-chloro-2-methoxybenzenecarboxyimidoyl chloride (13.6 g, 92%).

Add triethylamine (10.1 mL, 100 mmol) to a solution of 5-chloro-2-methoxybenzenecarboxyimidoyl chloride (10.9 g, 50 mmol) and dihydropyran (4.2 g, 50 mmol) in THF (150 mL) at room temperature and stir the mixture for 48 hours. Dilute the mixture with water (500 mL) and extract with ethyl acetate (3×200 mL). Wash the combined organic extracts with brine (100 mL), dry over sodium sulfate and remove the solvents under reduced pressure to afford 3-(5-chloro-2-methoxyphenyl)-3a,5,6,7a-tetrahydro-4H-pyrano[3,2-d]isoxazole (12.9 g, >99%) that is used in the next step without purification.

Heat a solution of 3-(5-chloro-2-methoxyphenyl)-3a,5,6,7a-tetrahydro-4H-pyrano[3,2-d]isoxazole (12.0 g, 44 mmol) in 12 N HCl (200 mL) at 50° C. for 24 hours and then dilute the mixture with water (300 mL) and extract with ethyl acetate (3×200 mL). Wash the combined organic extracts with brine (100 mL), dry over Na$_2$SO$_4$ and remove the solvents under reduced pressure. Purify the residue by flash column chromatography on silica gel, eluting with ethyl acetate/hexanes (1:1), to provide 3-[3-(5-chloro-2-methoxyphenyl)isoxazol-4-yl]propan-1-ol (8.0 g, 68%).

Example 99

3-[3-(5-Chloro-2-methoxyphenyl)isoxazol-5-yl]propionic Acid

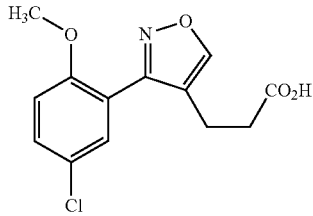 [SMILES: COc1ccc(Cl)cc1-c1nocc1CCC(=O)O]

Slowly add sodium perchlorate (2.0 g, 22 mmol) and bleach solution (1 mL) to a mixture of 3-[3-(5-chloro-2-methoxyphenyl)isoxazol-4-yl]propan-1-ol (3.0 g, 11 mmol), 2,2,6,6,-tetramethylpiperidinooxy (50 mg) in acetonitrile (30 mL), and saturated potassium phosphate solution (30 mL) at 35° C. and stir the mixture for 12 hours. Adjust the pH of the mixture to pH 8 with 2 N NaOH solution and add saturated sodium sulfite solution (40 mL). Wash the mixture with tert-butyl methyl ether (2×20 mL), acidify to pH 1 with 1 N HCl and extract with ethyl acetate (3×100 mL). Wash the combined organic extracts with brine (100 mL), dry over Na$_2$SO$_4$ and remove the solvents under reduced pressure to provide 3-[3-(5-chloro-2-methoxyphenyl)isoxazol-5-yl]propionic acid (2.65 g, 85%): APCI mass, spectrum m/z 280 [$C_{13}H_{12}ClNO_4$—H]$^-$.

Prepare Examples 100-102, compounds of formula II(l) listed in Table 12 below, by the same process as in the preparation of Example 99.

TABLE 12

II(l)

[structure: R$^1$ and R$^2$ substituted phenyl-isoxazol-(CH$_2$)$_4$—CO$_2$H]

Compounds of formula II(l)

| Example | R[1] | R[2] | mass spectrum m/z |
|---|---|---|---|
| 100 | OH | H | 260 [$C_{14}H_{15}NO_4 - H$]$^-$ |
| 101 | OCH3 | Cl | 308 [$C_{15}H_{16}ClNO_4 - H$]$^-$ |
| 102 | OH | Cl | 294 [$C_{14}H_{14}ClNO_4 - H$]$^-$ |

Preparation 14

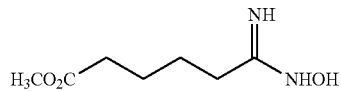

Add sodium carbonate (4.5 g, 42 mmol) to a solution of commercially available 5-cyano-pentanoic acid methyl ester (5.0 g, 35 mmol) and hydroxylamine hydrochloride (2.9 g, 42 mmol) in ethanol (100 mL) at room temperature under nitrogen and heat the mixture at reflux for 5.5 h. Filter the mixture through celite and remove the solvent under reduced pressure to provide crude methyl 5-(N-hydroxycarbamimidoyl)pentanoate (5.3 g, 87% yield), which is carried forward without further purification.

Example 103

Methyl 5-[5-(2-Methoxyphenyl)-[1,2,4]oxadiazol-3-yl]pentanoate

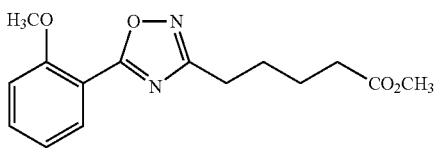 [SMILES: COC(=O)CCCCc1noc(-c2ccccc2OC)n1]

Add 2-methoxybenzoyl chloride (5.20 g, 35 mmol) to a solution of methyl 5-(N-hydroxycarbamimidoyl)pentanoate (5.3 g, 34 mmol) in pyridine (50 mL) under nitrogen at 0° C. and then heat the mixture at reflux for 6 h. Remove the solvent under reduced pressure, dilute the residue with ethyl acetate and wash with 1 N HCl. Wash the combined organic extracts with brine, dry over sodium sulfate and remove the solvent under reduced pressure. Purify the residue by flash column chromatography on silica gel, eluting with ethyl acetate/hexanes (1:4), to afford methyl 5-[5-(2-methoxyphenyl)[1,2,4]oxadiazol-3-yl]pentanoate (3.4 g, 33% over two steps): $^1$H NMR (CDCl$_3$) δ 1.7-1.85 (m, 2H), 1.85-2.00 (m, 2H), 2.35 (t, 2H), 2.95 (t, 2H), 3.65 (s, 3H), 3.95 (s, 3H), 7.00 (m, 2H), 7.45 (t, 1H), 8.00 (d, 1H).

Example 104

5-[5-(2-Methoxyphenyl)[1,2,4]oxadiazol-3-yl]pentanoic Acid

Add a solution of 2 N sodium hydroxide (20 mL) to a solution of methyl 5-[5-(2-methoxyphenyl)[1,2,4]oxadiazol-3-yl]pentanoate (3.4 g, 11 mmol) in methanol (50 mL) at room temperature under nitrogen and stir the mixture for 3.5 h. Remove the solvent under reduced pressure, dilute the residue with water (200 mL) and wash with diethyl ether (200 mL). Adjust the aqueous layer to pH 1 with 1 N HCl and collect the solids by vacuum filtration to afford 5-[5-(2-methoxyphenyl)[1,2,4]oxadiazol-3-yl]pentanoic acid (2.2 g, 72%): APCI MS m/z 275 [C$_{14}$H$_{16}$N$_2$O$_4$—H]$^-$.

Example 105

5-[5-(2-Hydroxyphenyl)[1,2,4]oxadiazol-3-yl]pentanoic Acid

Add boron tribromide (4.9 mL, 51.7 mmol) dropwise to a stirred solution of methyl 5-[5-(2-methoxyphenyl)[1,2,4]oxadiazol-3-yl]pentanoate (3.0 g, 10.3 mmol) in methylene chloride (70 mL) at 0° C. under nitrogen. Allow to warm to room temperature and stir for 5 hours. Cool the mixture to 0° C., add methanol (20 mL) dropwise and allow to warm to room temperature. Remove the solvents under reduced pressure and purify the residue by flash column chromatography on silica gel, eluting with ethyl acetate/hexanes (1:9), to provide methyl 5-[5-(2-hydroxyphenyl)[1,2,4]oxadiazol-3-yl]pentanoate, which is used without further purification. Add a solution of sodium hydroxide (800 mg, 20 mmol) in water (15 mL) to a solution of methyl 5-[5-(2-hydroxyphenyl)[1,2,4]oxadiazol-3-yl]pentanoate (2.6 g, 9.4 mmol) in methanol (30 mL) at room temperature and stir the mixture for 2 hours. Adjust the pH of the mixture to 2 with 1 N HCl and extract with ethyl acetate (2×150 mL). Wash the combined organic extracts with water (3×150 mL), dry over sodium sulfate and remove the solvent under reduced pressure. Triturate the residue with hexanes/ethyl acetate and collect the solids by vacuum filtration to afford the title compound (2.4 g, 89% over two steps). APCI MS m/z 261 [C$_{13}$H$_{14}$N$_2$O$_4$—H]$^-$.

Preparation 15

5-[2-(2-methoxyphenyl)-2-oxo-ethylcarbamoyl]-pentanoic acid methyl ester

Add sodium azide (2.14 g, 32.92 mmol) to a solution of 2-bromo-2'-methoxyacetophenone (5.01 g, 21.87 mmol) in 75 ml of DMSO. Stir the mixture at ambient temperature for 18 hours and dilute it with 250 ml of water. Extract the mixture with ether (3×). Dry the combined organic layers with MgSO$_4$. Filter off the drying agent and concentrate in vacuo to afford 3.54 g of 2-azido-1-(2-methoxyphenyl)-ethanone.

Dissolve 2-azido-1-(2-methoxy-phenyl)-ethanone (3.54 g, 18.5 mmol) in 1328 ml of MeOH and 9 ml of concentrated HCl. Add 943 mg of 10% Pd/C and expose the reaction mixture to 60 psi of H$_2$ for 5 hours at ambient temperature. Filter the catalyst off through a pad of celite and concentrate the filtrate in vacuo to afford 3.74 g of crude 2-amino-1-(2-methoxyphenyl)-ethanone as the hydrochloride salt.

Dissolve 1-[3-(dimethylamino)propyl]-3-ethylcarbodiimide hydrochloride (3.57 g, 18.62 mmol), 4-(dimethylamino)pryidine (463.8 mg, 3.79 mmol) and adipic acid monomethyl ester (2.97 g, 18.55 mmol) in 100 mL of CH$_2$Cl$_2$ and allow it to stir at room temperature for 45 minutes. Add crude 2-amino-1-(2-methoxy-phenyl)-ethanone hydrochloride (3.74 g, 18.55 mmol) and triethylamine (3.75 g, 37.1 mmol) to the reaction mixture and allow it to stir at ambient temperature for 22 hours. Dilute the reaction with 200 mL of CH$_2$Cl$_2$ and wash it with 1 N HCl (2×), saturated aqueous NaHCO$_3$ (2×) and brine (1×). Dry the organic layer with MgSO$_4$. Filter the drying agent and concentrate in vacuo to afford 4.57 g of the titled product (80%): mass spectrum: m/z=308.1 (M+H).

Example 106

5-[5-(2-methoxyphenyl)-oxazol-2-yl)-pentanoic acid methyl ester

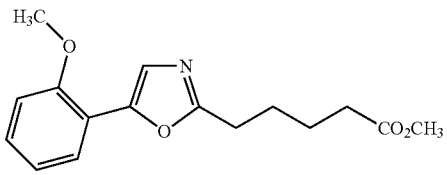 [SMILES: COC(=O)CCCCc1ncc(-c2ccccc2OC)o1]

Dissolve 5-[2-(2-methoxy-phenyl)-2-oxo-ethylcarbamoyl]-pentanoic acid methyl ester (4.57 g, 14.87 mmol) and 4-(dimethylamino)pryidine (3.56 g, 29.14 mmol) in 150 mL CH$_2$Cl$_2$ and cool the reaction mixture in an ice bath. Add triphenylphosphinedibromide (12.32 g, 1.96 mmol) to the reaction portionwise over 15 minutes. Raise the reaction to ambient temperature and allow it to stir for 12 hours. Wash the reaction with water and brine (2×). Dry the organic layers with MgSO$_4$. Filter off the drying agent and concentrate in vacuo to afford a crude residue. Purify the residue using silica gel chromatography eluting with hexanes/ethyl acetate mixtures to afford 2.47 g of the titled product (57%): mass spectrum: m/z=290.1 (M+H).

Example 107

5-[5-(2-methoxy-phenyl)-oxazol-2-yl]-pentanoic acid

Dissolve 5-[5-(2-methoxy-phenyl)-oxazol-2-yl]-pentanoic acid methyl ester (2.47 g, 8.54 mmol) in 40 mL of dioxane and add a solution of LiOH (1.0344 g, 43.19 mmol) in 20 mL of water to the solution. Allow the reaction to stir at ambient temperature for 21 hours. Acidify the reaction with 5N HCl and concentrate the reaction mixture in vacuo to remove the dioxane. Extract the aqueous residue with EtOAc (3×). Dry the combined organic layers with MgSO$_4$. Filter off the drying agent and concentrate in vacuo to afford a crude residue. Recrystallize the residue in EtOAc/hexanes to afford 1.7692 g of the titled product (75%): mass spectrum: m/z=276.1 (M+H).

Preparation 16

5-[2-(5-Chloro-2-methoxy-phenyl)-2-oxo-ethylcarbamoyl]-pentanoic acid methyl ester Dissolve 5'-chloro-2'-hydroxyacetophenone (15.3594 g, 90.03 mmol) in 100 mL of anhydrous acetonitrile in a pressure vessel. Add K$_2$CO$_3$ (13.7541 g, 99.52 mmol) and MeI (25.56 mL, 180.06 mmol) to the vessel. Seal the vessel and heat the reaction mixture to 85° C. for 18 hours. Cool the reaction and concentrate it in vacuo. Partition the residue between Et$_2$O and H$_2$O. Wash the organic layers with 2N NaOH (2×). Dry the combined organic layers with MgSO$_4$. Filter off the drying agent and concentrate in vacuo to afford 13.15 g of 1-(5-chloro-2-methoxy-phenyl)-ethanone (79%).

Suspend CuBr$_2$ (29.44 g, 131.81 mmol) in 150 mL EtOAc and heat it to reflux. Dissolve 1-(5-chloro-2-methoxy-phenyl)-ethanone (13.15 g, 71.23 mmol) in 100 mL of CHCl$_3$ and add it dropwise to the reaction. After 4 hours, filter the reaction to remove the solids. Concentrate the filtrate in vacuo and dissolve the residue in EtOAc. Wash the organic layer with saturated aqueous NaHCO$_3$ and water. Dry the organic layer with MgSO$_4$. Filter off the drying agent and concentrate in vacuo to afford 17.07 g of 2-bromo-1-(5-chloro-2-methoxy-phenyl)-ethanone.

Dissolve 2-bromo-1-(5-chloro-2-methoxy-phenyl)-ethanone (17.07 g, 64.78 mmol) in 150 mL of CHCl$_3$ and add hexamethylenetetramine (9.09 g, 64.84 mmol) to the reaction mixture. Allow the reaction to stir at ambient temperature for 23 hours. Collect the solids via filtration and wash the solids with Et$_2$O. Slurry the solid in 100 mL of MeOH and add 50 mL of concentrated HCl to it dropwise. Heat the reaction to reflux and allow it to stir for 23 hours. Cool the reaction to ambient temperature and filter off the solids. Slurry the filtrate in MeOH and again collect the solids via filtration. Concentrate the filtrate to afford 10.99 g of 2-amino-1-(5-chloro-2-methoxy-phenyl)-ethanone hydrochloride.

Dissolve 1-[3-(dimethylamino)propyl]-3-ethylcarbodiimide hydrochloride (8.0362 g, 41.92 mmol), 4-(dimethylamino)pryidine (1.0525 g, 8.62 mmol) and adipic acid monomethyl ester (6.71 g, 41.90 mmol) in 100 mL of CH$_2$Cl$_2$ and allow it to stir at room temperature for 45 minutes. Add crude 2-amino-1-(5-chloro-2-methoxy-phenyl)-ethanone hydrochloride (10.99 g, 46.55 mmol) and triethylamine (9.42 g, 93.1 mmol) to the reaction mixture and allow it to stir at ambient temperature for 21 hours. Dilute the reaction with 200 mL of CH$_2$Cl$_2$ and wash it with 1 N HCl (2×), saturated aqueous NaHCO$_3$ (2×) and brine (1×). Dry the organic layer with MgSO$_4$. Filter off the drying agent and concentrate in vacuo to afford 9.39 g of the crude titled product: mass spectrum: m/z=342.1 (M+H).

Example 108

5-[5-(5-chloro-2-methoxy-phenyl)-oxazol-2-yl]-pentanoic acid methyl ester

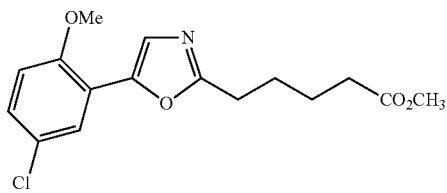 [SMILES: COC(=O)CCCCc1ncc(-c2cc(Cl)ccc2OC)o1]

Dissolve 5-[2-(5-Chloro-2-methoxy-phenyl)-2-oxo-ethylcarbamoyl]-pentanoic acid methyl ester (9.39 g, 27.47 mmol) and 4-(dimethylamino)pyridine (6.54 g, 53.53 mmol) in 250 mL of CH$_2$Cl$_2$ and cool the reaction mixture in an ice bath. Add triphenylphosphinedibromide (22.54 g, 53.40 mmol) to the reaction portionwise over 15 minutes. Raise the reaction to ambient temperature and allow it to stir for 17 hours. Wash the reaction with water (1×) and brine (2×). Dry the organic layers with MgSO$_4$. Filter off the drying agent and concentrate in vacuo to afford a crude residue. Purify the residue using silica gel chromatography eluting with hexanes/ethyl acetate mixtures to afford 4.38 g of the titled product (49%): mass spectrum: m/z=324.1 (M+H).

Example 109

5-[5-(5-Chloro-2-hydroxy-phenyl)-oxazol-2-yl]-pentanoic acid methyl ester

Dissolve 5-[5-(5-chloro-2-methoxy-phenyl)-oxazol-2-yl]-pentanoic acid methyl ester (4.174 g, 12.89 mmol) in 50 mL of CH$_2$Cl$_2$ and cool the solution to −78° C. Add boron tribromide (48.9 mL of a 1M solution in CH$_2$Cl$_2$) dropwise to the reaction and allow it to warm to ambient temperature and allow it to stir for 27 hours. Cool the reaction to −78° C. and quench it by adding 100 mL of MeOH dropwise to the reaction mixture. Allow the reaction to warm to ambient temperature and stir for 19 hours. Concentrate the reaction mixture in vacuo. Dissolve the residue in CH$_2$Cl$_2$ and wash it with saturated aqueous NaHCO$_3$ and brine. Dry the organic layer with MgSO$_4$. Filter off the drying agent and concentrate in vacuo to afford a crude residue. Purify the residue using silica gel chromatography eluting with hexanes/ethyl acetate mixtures to afford 3.26 g of the titled product (82%): mass spectrum: m/z=310.09 (M+H).

Example 110

5-[5-(5-Chloro-2-hydroxy-phenyl)-oxazol-2-yl]-pentanoic acid

Dissolve 5-[5-(5-chloro-2-hydroxy-phenyl)-oxazol-2-yl]-pentanoic acid methyl ester (3.26 g, 10.52 mmol) in 50 mL of dioxane and add a solution of LiOH (1.2671 g, 50.91 mmol) in 25 mL of water to it. Allow the reaction to stir at ambient temperature for 18 hours. Acidify the reaction with 5N HCl and concentrate the reaction mixture in vacuo to remove the dioxane. Extract the aqueous residue with EtOAc (3×). Dry the combined organic layers with MgSO₄. Filter off the drying agent and concentrate in vacuo to afford a crude residue. Triturate the residue in cold EtOAc. Collect the product via filtration to afford 1.8837 g of the titled product (60%): mass spectrum: m/z=296.1 (M+H).

Example 111

5-[4-(2-methoxy-phenyl)-thiazol-2-yl]-pentanoic acid methyl ester

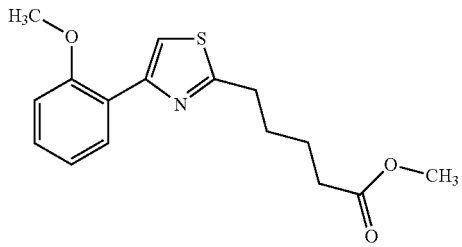 [SMILES: COC(=O)CCCCc1nc(-c2ccccc2OC)cs1]

Bubble gaseous ammonia through a gas dispersion tube through a rapidly stirred 0° C. solution of methyl adipoyl chloride (17.0 mL, 100.0 mmol) in dioxane (200 mL, anhydrous) for 30 minutes. Allow to warm to room temperature. After 1 hour, filter out solid ammonium chloride and concentrate mother liquor to get 20 grams of a white solid. Add 20% i-PrOH/CHCl₃ to material, dry over MgSO₄ and concentrate to afford 5-carbamoyl-pentanoic acid methyl ester (15.09 g, 95%).

Add THF (200 mL, anhydrous) to a sealed vessel containing 5-carbamoyl-pentanoic acid methyl ester (11.94 g, 75.0 mmol) and phosphorous pentasulfide (16.67 g, 37.5 mmol). Flush vessel with N₂, seal, and sonicate for 75 minutes. Break up solids and stir sealed under N₂ at room temperature for 50 hours. Concentrate, triturate with boiling CHCl₃ and filter hot (×3). Concentrate combined mother liquors to get 14.5 g yellow residue. Purify the residue by flash chromatography on silica gel eluting with 0-60% EtOAc/hexanes to afford 5-thiocarbamoyl-pentanoic acid methyl ester (7.72 g, 59%).

Add THF (125 mL, anhydrous) to a sealed vessel containing 5-thiocarbamoyl-pentanoic acid methyl ester (7.25 g, 41.4 mmol) and 2-bromo-2'-methoxyacetophenone (9.48 g, 41.4 mmol). Flush vessel with N₂, seal, and heat at 80° C. overnight. Cool to room temperature, add EtOAc, wash with saturated aqueous NaHCO₃ solution, brine, and backextract from each aqueous layer with EtOAc. Dry combined organic layers over MgSO₄ and concentrate to get 18 grams of purple residue. Adsorb on SiO₂ and purify the residue by flash chromatography on silica gel eluting with 0-20% EtOAc/hexanes to afford the title compound (9.7 g, 77%). TLC (30% EtOAc/hexanes) R$_f$=0.38. MS (IS) 306 (M+1)⁺.

Example 112

5-[4-(2-methoxy-phenyl)-thiazol-2-yl]-pentanoic acid

Add a solution of LiOH.H₂O (2.62 g, 62.5 mmol) in water (60 mL) to a rapidly stirred solution of 5-[4-(2-methoxy-phenyl)-thiazol-2-yl]-pentanoic acid methyl ester (3.82 g, 12.5 mmol) in dioxane (120 mL), stir at room temperature. After 1 hour, acidify to pH 1 with 5N HCl solution and concentrate to remove the majority of the dioxane. Partition residue between 20% i-PrOH/CHCl₃ and 1N HCl solution, separate layers. Backextract from aqueous layer with 20% i-PrOH/CHCl₃ and dry combined organic layers over MgSO₄, and concentrate to get 3 grams of a pink oil. Recrystallize from EtOAc to afford the title compound (2.52 g, 69%). MS (IS) 292 (M+1)⁺.

Example 113

5-[4-(2-hydroxy-phenyl)-thiazol-2-yl]-pentanoic acid

Dissolve 5-[4-(2-methoxy-phenyl)-thiazol-2-yl]-pentanoic acid methyl ester (3.20 g, 10.5 mmol) in acetic acid (50 mL, glacial), add HBr (50 mL, 48% aqueous solution) and heat to reflux under N₂ for 6 hours. Add additional HBr (20 mL, 48% aqueous solution) and heat at reflux under N₂ overnight. Adjust to pH 4 with 5N NaOH solution, extract with EtOAc (×2), dry over MgSO₄ and concentrate to get 2.64 grams of a light brown solid. Recrystallize from EtOAc/hexanes to afford the title compound (2.14 g, 74%). MS (IS) 278 (M+1)⁺.

Preparation 17

2-bromo-1-(2-hydroxy-4-methoxy-phenyl)-ethanone

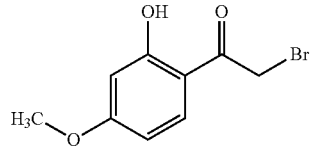

Heat a suspension of copper (II) bromide (16.79 g, 75.2 mmol) in EtOAc (40 mL) to reflux under N₂. Add a solution of 2'-hydroxy-4'-methoxyacetophenone (7.48 g, 45.0 mmol) in CHCl₃ (40 mL) to the suspension dropwise over 3 minutes. Attach a drying tube to the top of the condenser and reflux for 6 hours. Cool to room temperature and stir under N₂ overnight. Filter mixture and rinse filter cake with EtOAc and CHCl₃, concentrate mother liquor to get 12.75 grams of a green oily solid. Adsorb on SiO₂ and purify the residue by flash chromatography on silica gel eluting with 0-20% EtOAc/hexanes to afford the crude (approx. 75% pure) title compound (8.5 g, 77%).

Example 114

5-[4-(2-hydroxy-4-methoxy-phenyl)-thiazol-2-yl]-pentanoic acid methyl ester

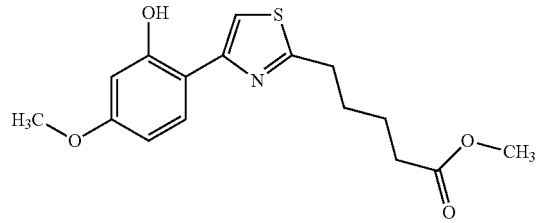

Add THF (50 mL, anhydrous) to a roundbottom flask containing 5-thiocarbamoyl-pentanoic acid methyl ester (2.63 g, 15.0 mmol) and 2-bromo-1-(2-hydroxy-4-methoxy-phenyl)-ethanone (4.90 g, 15.0 mmol, 75% pure). Heat to reflux under N₂ overnight. Cool to room temperature, add EtOAc, wash with saturated NaHCO₃ solution, brine, and backextract from each aqueous layer with EtOAc. Dry combined organic layers over MgSO₄ and concentrate to get 8 grams of a yellow solid. Adsorb on SiO₂ and purify the residue by flash chromatography on silica gel eluting with 0-20% EtOAc/hexanes followed by flash chromatography on silica gel eluting with CHCl₃ to afford the title compound (2.69 g, 56%). MS (IS) 322 (M+1)⁺.

Example 115

5-[4-(2-hydroxy-4-methoxy-phenyl)-thiazol-2-yl]-pentanoic acid

Add a solution of LiOH.H$_2$O (1.76 g, 41.9 mmol) in water (25 mL) to a rapidly stirred solution of 5-[4-(2-hydroxy-4-methoxy-phenyl)-thiazol-2-yl]-pentanoic acid methyl ester (2.69 g, 8.4 mmol) in dioxane (50 mL), stir at room temperature. After 1 hour, acidify to pH 1 with 5N HCl solution and cool under N$_2$ in a refrigerator. Filter out solids and rinse with ice cold water. Dry solids in a vacuum oven overnight to afford the title compound (2.50 g, 96%). MS (IS) 308 (M+1)$^+$.

Preparation 18

1-Ethynyl-2-methoxy-benzene

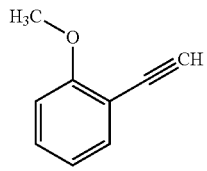

Add 2-iodo-anisole (17.55 g, 75.0 mmol), trimethylsilyl acetylene (15.9 mL, 112.5 mmol), copper (I) iodide (0.29 g, 1.5 mmol), and THF (225 mL, anhydrous) to a dry round bottom flask. Add diisopropylamine (22.1 mL, 157.5 mmol) and dichlorobis(triphenylphosphine) palladium (II) (1.58 g, 2.3 mmol) and stir the mixture at room temperature under N$_2$. After 2.5 hours, quench reaction with water and extract with EtOAc (x2). Wash combined organic layers with brine, dry over MgSO$_4$ and concentrate to get 20.8 grams of a black oil. Adsorb on SiO$_2$ and purify the residue by flash chromatography on silica gel eluting with 0-5% EtOAc/hexanes to afford 2-methoxy-phenylethynyl)-trimethylsilane (13.2 g, 86%).

Add a solution of potassium hydroxide (3.66 g, 65.2 mmol) in water (30 mL) dropwise over 30 minutes to a stirred solution of (2-methoxy-phenylethynyl)-trimethylsilane (13.2 g, 64.6 mmol) in methanol (275 mL) and stir at room temperature for 1.5 hours. Concentrate, add brine to residue, and extract with EtOAc. Dry organic layer over MgSO$_4$ and concentrate to get 10.5 grams of a black oil. Adsorb on SiO$_2$ and purify the residue by flash chromatography on silica gel eluting with 0-5% EtOAc/hexanes to afford the title compound (7.6 g, 89%).

Preparation 19

6-Nitro-hexanoic acid ethyl ester

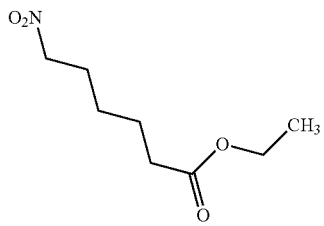

Add silver nitrite (23.1 g, 150 mmol) to a stirred solution of ethyl 6-bromo-hexanoate (17.7 mL, 100 mmol) in diethyl ether (125 mL, anhydrous) and heat to reflux under N$_2$ overnight. Filter through a pad of Celite® and rinse pad with diethyl ether, concentrate to get 21 grams of a yellow oil. Adsorb on SiO$_2$ and purify the residue by flash chromatography on silica gel eluting with 0-20% EtOAc/hexanes to afford the title compound (14.0 g, 74%).

Example 116

5-[5-(2-Methoxy-phenyl)-isoxazol-3-yl]-pentanoic acid ethyl ester

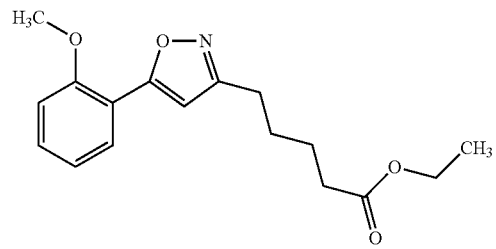 [SMILES: CCOC(=O)CCCCc1cc(-c2ccccc2OC)on1]

Add 1,4-phenylenediisocyanate (14.5 g, 90.8 mmol) to a stirred solution of 1-ethynyl-2-methoxy-benzene (4.0 g, 30.3 mmol) and 6-nitro-hexanoic acid ethyl ester (8.6 g, 45.4 mmol) in toluene (300 mL, anhydrous) and stir under N$_2$. Add triethylamine (12.7 mL, 90.8 mmol) and heat to reflux under N$_2$. After 2.5 hours, filter mixture through a pad of Celite® and rinse with toluene. Concentrate to get 9 grams of a orange oil. Adsorb on SiO$_2$ and purify the residue by flash chromatography on silica gel eluting with 0-20% EtOAc/hexanes to afford the title compound (14.0 g, 74%).

Example 117

5-[5-(2-Methoxy-phenyl)-isoxazol-3-yl]-pentanoic acid

Add a solution of LiOH.H$_2$O (1.83 g, 43.5 mmol) in water (30 mL) to a rapidly stirred solution of 5-[5-(2-methoxy-phenyl)-isoxazol-3-yl]-pentanoic acid ethyl ester (2.64 g, 8.7 mmol) in dioxane (60 mL) and stir overnight at room temperature. After 1 hour, acidify to pH 1 with 5N HCl solution and concentrate to remove the majority of the dioxane. Partition residue between 20% i-PrOH/CHCl$_3$ and 1N HCl solution and separate layers. Backextract from aqueous layer with 20% i-PrOH/CHCl$_3$ and dry combined organic layers over MgSO$_4$, and concentrate to get 2.5 grams of a yellow oil. Recrystallize from EtOAc/hexanes to afford the title compound (1.96 g, 82%). MS (IS) 276 (M+1)$^+$.

Example 118

5-[5-(2-Hydroxy-phenyl)-isoxazol-3-yl]-pentanoic acid ethyl ester

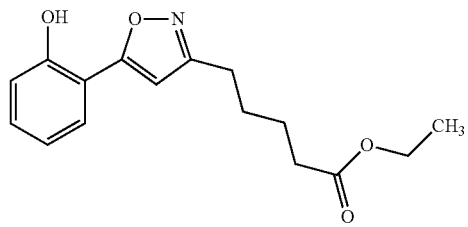 [SMILES: CCOC(=O)CCCCc1cc(-c2ccccc2O)on1]

Add boron tribromide (43 mL, 43 mmol, 1.0 M solution in CH$_2$Cl$_2$) dropwise over 30 minutes to a stirred 0° C. solution of 5-[5-(2-methoxy-phenyl)-isoxazol-3-yl]-pentanoic acid ethyl ester (5.20 g, 17.1 mmol) in CH$_2$Cl$_2$ (45 mL). Allow to warm to room temperature overnight. Add boron tribromide (17 mL, 17 mmol, 1.0 M solution in CH$_2$Cl$_2$) and stir at room temperature under N$_2$. After 4 hours, add boron tribromide (17 mL, 17 mmol, 1.0 M solution in CH$_2$Cl$_2$) and stir at room temperature under N$_2$. After 2 hours, quench via dropwise addition of ethanol (50 mL, absolute). Concentrate, dissolve residue in CHCl$_3$, wash with saturated NaHCO$_3$ solution (×2), dry over MgSO$_4$ and concentrate to get 4.7 g of a tan solid. Adsorb on SiO$_2$ and purify the residue by flash chromatography on silica gel eluting with 3-20% EtOAc/hexanes to afford the title compound (3.96 g, 80%). MS (IS) 290 (M+1)$^+$.

Example 119

5-[5-(2-Hydroxy-phenyl)-isoxazol-3-yl]-pentanoic acid

Add a solution of LiOH.H$_2$O (2.87 g, 68.4 mmol) in water (60 mL) to a rapidly stirred solution of 5-[5-(2-hydroxy-phenyl)-isoxazol-3-yl]-pentanoic acid ethyl ester (3.96 g, 13.7 mmol) in dioxane (120 mL) and stir at room temperature overnight. After 1 hour, acidify to pH 1 with 5N HCl solution and concentrate to remove the majority of the dioxane. Add water to residue and place in refrigerator overnight. Filter out solids, wash with water, dry in a 50° C. vacuum oven for 6 hours to afford the title compound (3.11 g, 87%). MS (IS) 262 (M+1)$^+$.

Preparation 20

4-Chloro-2-ethynyl-1-methoxy-benzene

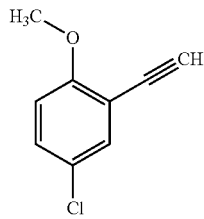

Add 4-chloro-2-iodo-anisole (10.9 mL, 75.0 mmol), trimethylsilyl acetylene (15.9 mL, 112.5 mmol), copper (I) iodide (0.29 g, 1.5 mmol), and THF (225 mL, anhydrous) to a dry round bottom flask. Add diisopropylamine (22.1 mL, 157.5 mmol) and dichlorobis(triphenylphosphine) palladium (II) (1.58 g, 2.3 mmol) and stir the mixture at room temperature under N$_2$ overnight. Quench reaction with water and extract with EtOAc (×2). Wash combined organic layers with brine, dry over MgSO$_4$ and concentrate to get 24 g of a black oil. Adsorb on SiO$_2$ and purify the residue by flash chromatography on silica gel eluting with 0-3% EtOAc/hexanes to afford (5-chloro-2-methoxy-phenylethynyl)-trimethylsilane (13.7 g, 76%).

Add a solution of potassium hydroxide (3.28 g, 58.5 mmol) in water (30 mL) dropwise over 25 minutes to a stirred solution of (5-chloro-2-methoxy-phenylethynyl)-trimethylsilane (13.7 g, 57.4 mmol) in methanol (275 mL) and stir at room temperature for 2 hours. Concentrate, add brine to residue, and extract with EtOAc (×2). Dry organic layer over MgSO$_4$ and concentrate to get 13 g of a black oil. Adsorb on SiO$_2$ and purify the residue by flash chromatography on silica gel eluting with 0-5% EtOAc/hexanes to afford the title compound (8.98 g, 94%).

Example 120

5-[5-(5-chloro-2-methoxy-phenyl)-isoxazol-3-yl]-pentanoic acid ethyl ester

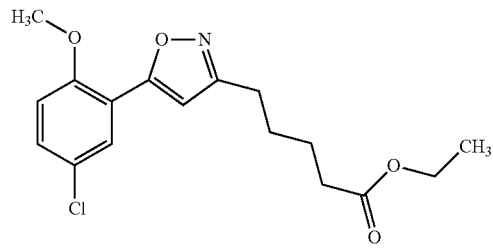 [SMILES: CCOC(=O)CCCCc1cc(-c2cc(Cl)ccc2OC)on1]

Add 1,4-phenylenediisocyanate (8.41 g, 52.5 mmol) to a stirred solution of 4-chloro-2-ethynyl-1-methoxy-benzene (4.0 g, 30.3 mmol) and 6-nitro-hexanoic acid ethyl ester (8.6 g, 45.4 mmol) in toluene (300 mL, anhydrous) and stir at room temperature under N$_2$. Add triethylamine (7.3 mL, 52.5 mmol) and heat to reflux under N$_2$ overnight. Filter mixture through a pad of Celite® and rinse with toluene. Concentrate to get 6.6 g of a orange oil. Adsorb on SiO$_2$ and purify the residue by flash chromatography on silica gel eluting with 0-40% EtOAc/hexanes to afford the title compound (4.51 g, 76%). MS (IS) 338 (M+1)$^+$.

Example 121

5-[5-(5-chloro-2-hydroxy-phenyl)-isoxazol-3-yl]-pentanoic acid ethyl ester

Add boron tribromide (39 mL, 39 mmol, 1.0 M solution in CH$_2$Cl$_2$) dropwise to a stirred −78° C. solution of 5-[5-(5-chloro-2-methoxy-phenyl)-isoxazol-3-yl]-pentanoic acid ethyl ester (4.39 g, 13 mmol) in CH$_2$Cl$_2$ (40 mL). Allow to warm to room temperature. After 2 hours, cool to −78° C. and add boron tribromide (13 mL, 13 mmol, 1.0 M solution in CH$_2$Cl$_2$) dropwise and allow to warm to room temperature overnight. Quench via dropwise addition of ethanol (60 mL, absolute). Concentrate, dissolve residue in CHCl$_3$, wash with saturated NaHCO$_3$ solution (×2), dry over MgSO$_4$ and concentrate to get 3.7 g of a tan solid. Adsorb on SiO$_2$ and purify the residue by flash chromatography on silica gel eluting with 0-60% EtOAc/hexanes to afford the title compound (3.3 g, 78%). MS (IS) 324 (M+1)$^+$.

Example 122

5-[5-(5-chloro-2-hydroxy-phenyl)-isoxazol-3-yl]-pentanoic acid

Add a solution of LiOH.H$_2$O (2.14 g, 51.0 mmol) in water (30 mL) to a rapidly stirred solution of 5-[5-(5-chloro-2-hydroxy-phenyl)-isoxazol-3-yl]-pentanoic acid ethyl ester (3.30 g, 10.2 mmol) in dioxane (60 mL), stir at room temperature overnight. After 1 hour, acidify to pH 1 with 5N HCl solution and place in refrigerator. Filter out solids and rinse with water to afford the title compound (2.73 g, 91%). MS (IS) 296 (M+1)$^+$.

Example 123

5-[4-(2-amino-phenyl)-oxazol-2-yl]-pentanoic acid methyl ester

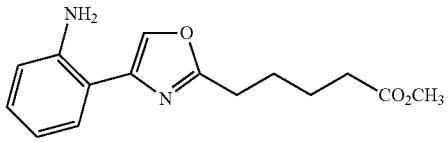 [SMILES: COC(=O)CCCCc1nc(-c2ccccc2N)co1]

Dissolve methyl adipoyl chloride (27 mL, 159 mmol) in dioxane (300 mL) and place the vessel in a room temperature water bath. Carefully bubble in ammonia gas (excess) and allow the mixture to stir for 1-2 hours. Filter the mixture to remove solids. Suspend solids in $CHCl_3$ and filter again. Concentrate the combined filtrates and dry in vacuo to give 24.87 g (98%) of 5-carbamoyl-pentanoic acid methyl ester.

Combine 2-bromo-2'-nitroacetophenone (9.6 g, 39.3 mmol) with 5-carbamoyl-pentanoic acid methyl ester (12.0 g, 75.5 mmol) and heat the neat mixture in a sealed vessel at 120-140° C. for about 6 hours. Cool the mixture and add methanol and allow the mixture to stir overnight at room temperature. Concentrate the mixture and partition the residue between aq $NaHCO_3$ and EtOAc. Dry the combined extracts over $Na_2SO_4$ and concentrate. Initial chromatography over silica gel ($CH_2Cl_2$) followed by a second chromatography over silica gel (Hex/EtOAc) allowed for recovery of 5-[4-(2-nitro-phenyl)-oxazol-2-yl]-pentanoic acid methyl ester (4.65 g, 39%). MS (ES): $(M+1)^+$ 305.1, 306.3 m/z.

Combine 5-[4-(2-nitro-phenyl)-oxazol-2-yl]-pentanoic acid methyl ester (2.5 g, 8.2 mmol) with 5% Pd/C (300 mg) and Pd/black (50 mg) in THF and react with hydrogen (init. 39 psi) in a Parr® apparatus. When reduction is complete, filter the mixture through Celite® and concentrate the filtrate. Chromatograph the residue over silica gel ($MeOH/CH_2Cl_2$) to allow for recovery of 2.05 g (91%) of 5-[4-(2-amino-phenyl)-oxazol-2-yl]-pentanoic acid methyl ester. MS (ES): $(M+1)^+$ 275.1, 276.2 m/z.

Example 124

5-[4-(2-Amino-phenyl)-oxazol-2-yl]-pentanoic acid

Combine 5-[4-(2-amino-phenyl)-oxazol-2-yl]-pentanoic acid methyl ester (2.5 g, 9.1 mmol) with THF (3 mL), EtOH (3 mL) and 1N NaOH (15 mL) and stir until hydrolysis is complete. Concentrate the mixture, dilute the residue with water and adjust the pH to 2.5-3.5 with aq HCl. Extract the mixture with EtOAc and dry the extracts over $Na_2SO_4$ before concentrating. Chromatograph the residue over silica gel (EtOAc) to allow for recovery of 5-[4-(2-amino-phenyl)-oxazol-2-yl]-pentanoic acid (2.03 g, 86%). MS (ES): $(M+1)^+$ 261.1 m/z.

Example 125

5-[4-(2-Methanesulfonylamino-phenyl)-oxazol-2-yl]-pentanoic acid methyl ester

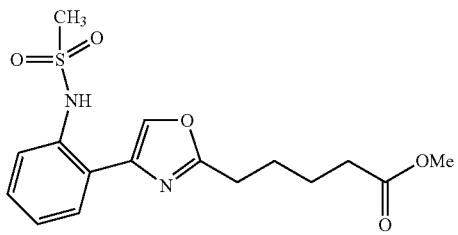 [SMILES: COC(=O)CCCCc1nc(-c2ccccc2NS(C)(=O)=O)co1]

Dissolve 5-[4-(2-amino-phenyl)-oxazol-2-yl]-pentanoic acid methyl ester (2.18 g, 7.96 mmol) in THF (50 mL) and add pyridine (1.20 mL, 14.8 mmol). Add methanesulfonyl chloride (excess) and allow the mixture to stir at room temperature until reaction is complete. Concentrate the mixture and quench the residue with ice/aq $NaHCO_3$ and extract with EtOAc. Dry the combined extracts over $Na_2SO_4$ and concentrate. Chromatograph the residue over silica gel (EtOAc/$CH_2Cl_2$) to allow for isolation of 5-[4-(2-methanesulfonylamino-phenyl)-oxazol-2-yl]-pentanoic acid methyl ester (2.8 g, 100%). MS (ES): $(M+1)^+$ 353.2, 354.3 m/z.

Example 126

5-[4-(2-Methanesulfonylamino-phenyl)-oxazol-2-yl]-pentanoic acid

Combine 5-[4-(2-methanesulfonylamino-phenyl)-oxazol-2-yl]-pentanoic acid methyl ester (2.75 g, 7.8 mmol) with THF (3 mL), EtOH (3 mL) and 1N NaOH (20 mL) and stir at room temperature until hydrolysis is complete. Concentrate the mixture and dilute the residue with water and adjust to pH 3.0-3.5 with aq HCl. Extract the mixture with EtOAc and dry the extracts over $Na_2SO_4$ before concentrating. Chromatograph the residue over silica gel (EtOAc) to allow for recovery of 5-[4-(2-methanesulfonylamino-phenyl)-oxazol-2-yl]-pentanoic acid (2.16 g, 82%). MS (ES): (M+1)+339.2, 340.3.

Example 127

5-[4-(2-Acetylamino-phenyl)-oxazol-2-yl]-pentanoic acid methyl ester

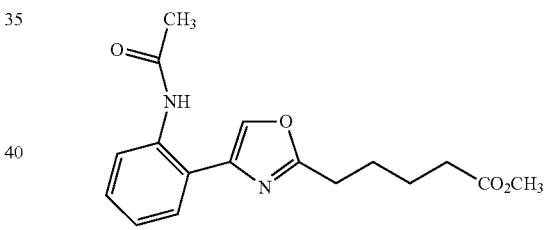

Dissolve 5-[4-(2-amino-phenyl)-oxazol-2-yl]-pentanoic acid methyl ester (4.05 g, 14.8 mmol) and triethylamine (2.26 mL, 16.2 mmol) in THF (40 mL) and stir at room temperature. Add acetyl chloride (1.16 mL, 16.2 mmol) and allow the mixture to stir overnight at room temperature. Concentrate the mixture and partition the residue between aq $NaHCO_3$ and EtOAc. Dry the combined extracts over $Na_2SO_4$ before concentrating. Chromatograph the residue over silica gel ($MeOH/CH_2Cl_2$) which allows for the isolation of 5-[4-(2-acetylamino-phenyl)-oxazol-2-yl]-pentanoic acid methyl ester (3.51 g, 75%). MS (ES): $(M+1)^+$ 317.2 m/z.

Example 128

5-[4-(2-Acetylamino-phenyl)-oxazol-2-yl]-pentanoic acid

Combine 5-[4-(2-acetylamino-phenyl)-oxazol-2-yl]-pentanoic acid methyl ester (3.26 g, 10.3 mmol) with THF (3 mL), EtOH (3 mL) and 1 N NaOH (40 mL) and stir at room temperature until hydrolysis is complete. Concentrate the mixture and dilute the residue with water before adjusting to pH 3.5-4.0 with aq HCl. Extract the mixture with 1-2% MeOH/EtOAc and concentrate the combined extracts in vacuo. Chromatograph the resulting residue over silica gel (MeOH/CH$_2$Cl$_2$) which allows for isolation of 5-[4-(2-acetylamino-phenyl)-oxazol-2-yl]-pentanoic acid (2.76 g, 89%). MS (ES): (M−1)$^−$ 301.2, 302.3.

Example 129

5-[5-(5-Chloro-2-hydroxy-phenyl)-isoxazol-3-yl]-pentanoic acid disodium salt

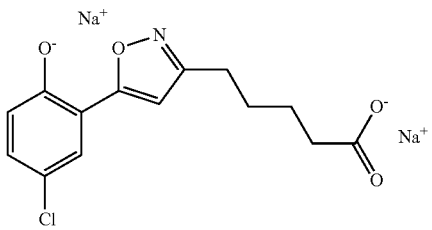 [SMILES: [Na+] ; O=C([O-])CCCCc1cc(-c2cc(Cl)ccc2[O-])on1 ; [Na+]]

Add a solution of NaOH (739 mg, 18.5 mmol) in water (3 mL) to a suspension of 5-[5-(5-chloro-2-hydroxy-phenyl)-isoxazol-3-yl]-pentanoic acid (2.73 g, 9.23 mmol) in water (5 mL) and stir at room temperature. Heat to 55° C. for 1 hour, filter hot solution, concentrate, place in 50-60° C. vacuum oven for 2 days. Scrape and crush solids, place in 50-60° C. vacuum oven overnight to afford the title compound (3.14 g, 100%). MS (IS) 296 (M+1)$^+$.

Preparation 21

5-Nitro-pentanoic acid methyl ester

Add silver nitrite (29.84 g, 193.9 mmol) to a stirred solution of methyl 5-bromovalerate (25.22 g, 129.3 mmol) in diethyl ether (165 mL, anhydrous) and heat to reflux under N$_2$ overnight. Filter through a pad of Celite® and rinse pad with diethyl ether, concentrate to get 21 g yellow oil. Adsorb on SiO$_2$ and purify the residue by flash chromatography on silica gel eluting with 0-20% EtOAc/hexanes to afford 7.87 g of the title compound (38%).

Example 130

4-[5-(2-Methoxy-phenyl)-isoxazol-3-yl]-butyric acid methyl ester

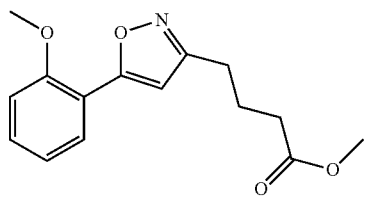 [SMILES: COC(=O)CCCc1cc(-c2ccccc2OC)on1]

Add 1,4-phenylenediisocyanate (19.22 g, 120.0 mmol) to a stirred solution of 1-ethynyl-2-methoxy-benzene (2204901, 5.29 g, 40.0 mmol) and 5-nitro-pentanoic acid methyl ester (7.91 g, 49.1 mmol) in toluene (300 mL, anhydrous) and stir under N$_2$. Add triethylamine (16.7 mL, 120.0 mmol) and heat to reflux under N$_2$ overnight. Filter mixture through a pad of Celite® and rinse with toluene. Concentrate to get 12.4 g yellow oil. Adsorb on SiO$_2$ and purify the residue by flash chromatography on silica gel eluting with 0-30% EtOAc/hexanes to afford the title compound (14.0 g, 74%). MS (IS) 276 (M+1)$^+$.

Example 131

4-[5-(2-methoxy-phenyl)-isoxazol-3-yl]-butyric acid

Add a solution of LiOH (0.98 g, 40.86 mmol) in water (30 mL) to a rapidly stirred solution of 4-[5-(2-Methoxy-phenyl)-isoxazol-3-yl]-butyric acid methyl ester (2.25 g, 8.17 mmol) in dioxane (60 mL), stir at room temperature overnight Quench with 1N HCl solution and concentrate to remove the majority of the dioxane. Add 1N NaOH to adjust pH to 4-5, extract with EtOAc (×2). Dry combined organic layers over MgSO$_4$ and concentrate to get 2.15 g yellow oil. Recrystallize from EtOAc/hexanes to afford the title compound (1.67 g, 78%). MS (IS) 262 (M+1)$^+$.

Example 132

4-[5-(2-methoxy-phenyl)-isoxazol-3-yl]-butyric acid methyl ester

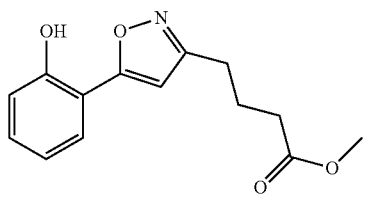 [SMILES: COC(=O)CCCc1cc(-c2ccccc2O)on1]

Add boron tribromide (51.2 mL, 51.2 mmol, 1.0 M solution in CH$_2$Cl$_2$) dropwise over 30 minutes to a stirred −78° C. solution of 5-[5-(2-methoxy-phenyl)-isoxazol-3-yl]-pentanoic acid ethyl ester (2.82 g, 10.2 mmol) in CH$_2$Cl$_2$ (30 mL). Allow to warm to room temperature overnight Cool to 0° C. and quench via dropwise addition of methanol (60 mL, anhydrous). Warm to room temperature, wash with saturated NaHCO$_3$ solution (×2), dry over MgSO$_4$ and concentrate to get 2.7 g yellow oil. Purify the residue by flash chromatography on silica gel eluting with 5-50% EtOAc/hexanes to afford the title compound (2.28 g, 85%). MS (IS) 262 (M+1)$^+$.

Example 133

5-[5-(2-hydroxy-phenyl)-isoxazol-3-yl]-pentanoic acid

Add a solution of LiOH (1.04 g, 43.6 mmol) in water (15 mL) to a rapidly stirred solution of 4-[5-(2-methoxy-phenyl)-isoxazol-3-yl]-butyric acid methyl ester (2.28 g, 8.7 mmol) in dioxane (120 mL), stir at room temperature overnight After 1 hour, acidify to pH 1 with 5N HCl solution and concentrate to remove the majority of the dioxane. Add water to residue and place in refrigerator overnight Filter out solids, wash with water, dry in a 50° C. vacuum oven for 6 hours to afford the title compound (3.11 g, 87%). MS (IS) 262 (M+1)$^+$.

Preparation 22

5-azido-pentanoic acid methyl ester

Add sodium azide (12.5 g, 193 mmol) to a rapidly stirred solution of methyl 5-bromovalerate (25.08 g, 129 mmol) in DMSO (200 mL, anhydrous). Stir at room temperature overnight under N₂. Add water (400 mL) and stir for 30 minutes. Extract with Et₂O (×3) and wash combined Et₂O layers with brine (×3). Dry organic layer over MgSO₄ and concentrate to give the title compound (20.3 g, 100%).

Examples 134 and 135

5-[4-(2-methoxy-phenyl)-[1,2,3]triazol-1-yl]-pentanoic acid methyl ester and 5-[5-(2-methoxy-phenyl)-[1,2,3]triazol-1-yl]-pentanoic acid methyl ester

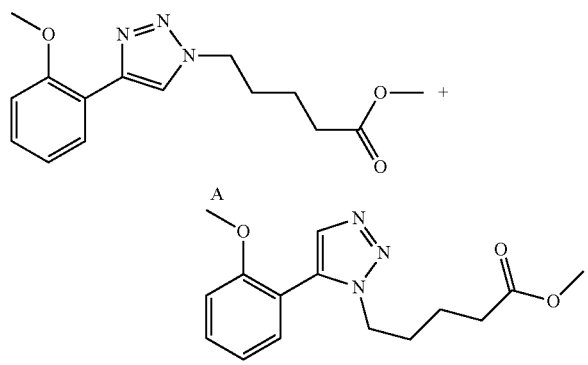

Add 1-ethynyl-2-methoxy-benzene (2204901, 5.29 g, 40.0 mmol), 5-azido-pentanoic acid methyl ester (9.43 g, 60.0 mmol), and toluene (120 mL, anhydrous) to a dry flask and heat at reflux under N2 overnight Concentrate and purify the residue by flash chromatography on silica gel eluting with 0-50% EtOAc/hexanes then 0-25% EtOAc/toluene to afford the title compounds A (2.85 g) and B (2.99 g) in a combined 50% yield. NOESY experiment confirmed the structure of A. MS (IS) 290 (M+1)⁺.

Example 136

5-[4-(2-hydroxy-phenyl)-[1,2,3]triazol-1-yl]-pentanoic acid

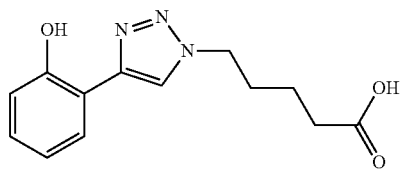 [SMILES: O=C(O)CCCCn1cc(-c2ccccc2O)nn1]

Combine 5-[4-(2-methoxy-phenyl)-[1,2,3]triazol-1-yl]-pentanoic acid methyl ester (2.40 g, 8.29 mmol), hydrobromic acid (50 mL, 48% in water), and acetic acid (25 mL, glacial) and heat to reflux under N₂ for 4 hours. Add hydrobromic acid (25 mL, 48% in water) and acetic acid (25 mL, glacial) and continue heating at reflux under N₂ overnight Cool to room temperature, filter out solids and dry in a 50° C. vacuum oven overnight to yield the title compound (1.45 g, 67%). MS (IS) 260 (M−1)⁻.

Example 137

5-[5-(2-hydroxy-phenyl)-[1,2,3]triazol-1-yl]-pentanoic acid

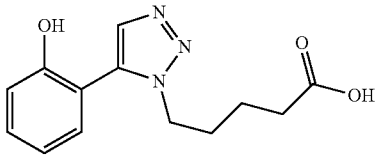 [SMILES: O=C(O)CCCCn1nncc1-c1ccccc1O]

Combine 5-[5-(2-methoxy-phenyl)-[1,2,3]triazol-1-yl]-pentanoic acid methyl ester (2.99 g, 10.3 mmol), hydrobromic acid (50 mL, 48% in water), and acetic acid (50 mL, glacial) and heat to reflux under N₂ for 3 hours. Add hydrobromic acid (20 mL, 48% in water) and continue heating at reflux under N₂ overnight. Cool to room temperature, basify to pH 4 with 5N NaOH solution. Extract from aqueous layer with EtOAc (×3), wash combined organic layers with brine, dry combined organic layers over MgSO₄ and concentrate to get 2.6 yellow oil. Concentrate, adsorb on SiO₂ and purify the residue by flash chromatography on silica gel eluting with 3-5% MeOH/CH₂Cl₂. Add Et₂O and concentrate (×5) in order to remove solvents and afford the title compound (2.16 g, 80%). MS (IS) 262 (M+1)⁺.

Example 138

5-[5-(2-hydroxy-phenyl)-[1,2,3]triazol-1-yl]-pentanoic acid disodium salt

Add a solution of NaOH (0.66 g, 16.53 mmol) in water (3 mL) to a suspension of 5-[5-(2-methoxy-phenyl)-[1,2,3]triazol-1-yl]-pentanoic acid (2.16 g, 8.27 mmol) and heat to 50° C. for 1 hour. Concentrate and dry in 50° C. vacuum oven overnight. Add Et₂O, sonicate and filter out solids. Dry solids in 50° C. vacuum oven overnight (as solids are highly hygroscopic) to afford the title compound (2.0 g, 79%). MS (IS) 262 (M+1)⁺.

Preparation 23

N-(2-ethynyl-phenyl)-acetamide

Add copper (I) iodide (0.38 g, 2.0 mmol) to a stirred solution of 2-iodo-aniline (21.9 g, 100.0 mmol) and trimethylsilyl acetylene (21.2 mL, 150.0 mmol) in THF (300 mL, anhydrous) in a dry RB flask. Add diisopropylamine (29.4 mL, 210.0 mmol) and dichlorobis(triphenylphosphine) palladium (II) (2.11 g, 3.0 mmol) and stir the mixture at room temperature under N₂. After 5 hours quench reaction with water and extract with EtOAc (×3). Dry combined organic layers over MgSO₄ and concentrate to get 27.5 g black oil. Adsorb on SiO₂ and purify the residue by flash chromatography on silica gel eluting with 0-10% EtOAc/hexanes to afford 2-trimethylsilanylethynyl-phenylamine (17.7 g, 93%). MS (IS) 190 (M+1)⁺.

Add acetic anhydride (2.6 mL, 27.5 mmol) dropwise to a stirred 0° C. solution of 2-trimethylsilanylethynyl-phenylamine (2238853, 4.73 g, 25.0 mmol) in pyridine (100 mL) under N₂. Allow to warm to room temperature overnight Concentrate and partition residue between EtOAc and 1N HCl, separate layers. Extract from aqueous layer with EtOAc, wash combined organic layers with brine, dry over MgSO₄ and concentrate. Adsorb on SiO₂ and purify the residue by flash chromatography on silica gel eluting with 0-15% EtOAc/hexanes to afford N-(2-trimethylsilanylethynyl-phenyl)-acetamide (4.67 g, 81%). MS (IS) 231.9 (M+1)⁺.

Add a solution of potassium hydroxide (1.62 g, 28.8 mmol) in water (100 mL) dropwise to a rapidly stirred solution of N-(2-trimethylsilanylethynyl-phenyl)-acetamide (4.44 g, 19.2 mmol) in methanol (50 mL) and stir at room temperature for 4 hours. Concentrate, add brine to residue and extract with EtOAc (×3). Dry combined organic layers over MgSO$_4$, concentrate, add CHCl$_3$ and concentrate to get 2.82 g light yellow solid. Purify the residue by flash chromatography on silica gel eluting with 0-30% EtOAc/hexanes to afford the title compound (2.56 g, 84%). MS (IS) 160 (M+1)$^+$.

Example 139

5-[5-(2-acetylamino-phenyl)-isoxazol-3-yl]-pentanoic acid ethyl ester

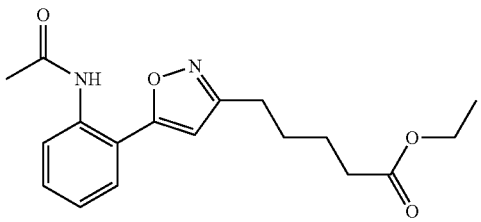 [SMILES: CCOC(=O)CCCCc1cc(-c2ccccc2NC(C)=O)on1]

Add 1,4-phenylenediisocyanate (5.15 g, 32.2 mmol) to a stirred solution of N-(2-ethynyl-phenyl)-acetamide (2.56 g, 16.1 mmol) and 6-nitro-hexanoic acid ethyl ester (4.56 g, 24.1 mmol) in toluene (200 mL, anhydrous) and stir under N$_2$. Add triethylamine (4.5 mL, 32.2 mmol) and heat to reflux under N$_2$ overnight. Filter mixture through a pad of Celite® and rinse with toluene. Concentrate to get 6.2 g yellow oil. Adsorb on SiO$_2$ and purify the residue by flash chromatography on silica gel eluting with 0-60% EtOAc/hexanes to afford the title compound (4.02 g, 76%). Correct regioisomer is confirmed by NOESY. MS (IS) 331 (M+1)$^+$.

Example 140

5-[5-(2-acetylamino-phenyl)-isoxazol-3-yl]-pentanoic acid

Add 2N HCl solution (100 mL, in water) to 5-[5-(2-acetylamino-phenyl)-isoxazol-3-yl]-pentanoic acid ethyl ester (4.02 g, 12.2 mmol) and heat to reflux under N$_2$ overnight Cool to room temperature and concentrate to afford the title compound (3.46 g, 96% yield). MS (IS) 259 (M–1)$^-$.

Preparation 24

5-{5-[4-methoxy-2-(2-trimethylsilanyl-ethoxymethoxy)-phenyl]-isoxazol-3-yl}-pentanoic acid ethyl ester

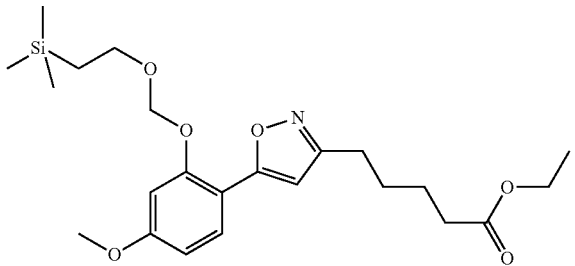 [SMILES: CCOC(=O)CCCCc1cc(-c2ccc(OC)cc2OCOCC[Si](C)(C)C)on1]

Add a fine suspension of iodine (25.4 g, 100 mmol) in CHCl$_3$ (700 mL) dropwise to a stirred mixture of 3-methoxyphenol (10.8 mL, 100 mmol), silver trifluoroacetate (22.1 g, 100 mmol), and CHCl3 (100 mL) over 2 h under N$_2$ at room temperature. Stir at room temperature under N$_2$ for 60 h then filter mixture over Celite® and rinse pad with CHCl$_3$. Wash solution with aqueous 0.1 N Na$_2$S$_2$O$_4$ solution, saturated NaHCO$_3$ solution and backextract from aqueous with CHCl$_3$. Dry combined organic layers over Na$_2$SO$_4$ and concentrate to get 26.6 g brown oil. Purify the residue by flash chromatography on silica gel eluting with CHCl$_3$ to afford 2-iodo-5-methoxy-phenol (18.4 g, 74%). MS (IS) 249 (M–1)$^-$.

Add copper (I) iodide (0.28 g, 1.5 mmol) to a stirred solution of 2-iodo-5-methoxy-phenol (18.4 g, 73.6 mmol) and trimethylsilyl acetylene (15.6 mL, 110.4 mmol) in THF (225 mL, anhydrous) in a dry RB flask. Add dichlorobis(triphenylphosphine) palladium (II) (1.55 g, 2.2 mmol) and diisopropylamine (21.7 mL, 154.5 mmol) and stir the mixture at room temperature under N$_2$ overnight Quench reaction with water and extract with EtOAc (×3). Dry combined organic layers over MgSO$_4$ and concentrate to get 29 g black oil. Adsorb on SiO$_2$ and purify the residue by flash chromatography on silica gel eluting with 0-15% EtOAc/hexanes to afford 5-methoxy-2-trimethylsilanylethynyl-phenol (11.5 g, 71%). MS (IS) 221 (M+1)$^+$.

Add diisopropylamine (11.0 mL, 78.3 mmol) to a rapidly stirred solution of 5-methoxy-2-trimethylsilanylethynyl-phenol (11.5 g, 52.2 mmol) in CH$_2$Cl$_2$ at room temperature under N$_2$. Add 2-(trimethylsilyl)ethoxymethyl chloride (13.9 mL, 78.3 mmol) dropwise over 5 minutes and stir at room temperature under N$_2$ overnight Acidify with aqueous 1N HCl solution, add water, separate layers. Extract from aqueous layer with CH$_2$Cl$_2$ (×2), dry combined organic layers over MgSO$_4$ and concentrate. Adsorb on SiO$_2$ and purify the residue by flash chromatography on silica gel eluting with 0-5% EtOAc/hexanes to afford 4-methoxy-2-(2-trimethylsilanyl-ethoxymethoxy)-1-trimethylsilanylethynyl-benzene (13.5 g, 74%). MS (IS) 351 (M+1)$^+$.

Add a solution of potassium hydroxide (2.3 g, 40.4 mmol) in water (20 mL) dropwise to a rapidly stirred solution of 4-methoxy-2-(2-trimethylsilanyl-ethoxymethoxy)-1-trimethylsilanylethynyl-benzene (13.5 g, 38.5 mmol) in methanol (200 mL) and stir at room temperature for 1 hour. Concentrate, add brine to residue and extract with EtOAc (×2). Dry combined organic layers over MgSO$_4$ and concentrate to get 11.7 g brown oil. Adsorb on SiO$_2$ and purify the residue by flash chromatography on silica gel eluting with 0-10% EtOAc/hexanes to afford [2-(2-ethynyl-5-methoxy-phenoxymethoxy)-ethyl]-trimethyl-silane (10.0 g, 93%). MS (IS) 279 (M+1)$^+$.

Add 1,4-phenylenediisocyanate (6.41 g, 40.0 mmol) to a stirred solution of [2-(2-ethynyl-5-methoxy-phenoxymethoxy)-ethyl]-silane (5.57 g, 20.0 mmol) and 6-nitro-hexanoic acid ethyl ester (7.56 g, 40.0 mmol) in toluene (150 mL, anhydrous) and stir under N$_2$. Add triethylamine (5.6 mL, 40.0 mmol) and heat to reflux under N$_2$. After 2 hours add additional toluene (150 mL, anhydrous) and continue refluxing overnight. Filter mixture through a pad of Celite® and rinse with toluene. Concentrate to get 8.7 g yellow oil. Purify the residue by flash chromatography on silica gel eluting with 0-20% EtOAc/hexanes then 0-30% Et$_2$O/hexanes to afford the title compound (5.20 g, 58%). Correct regioisomer is confirmed by NOESY. MS (IS) 450 (M+1)$^+$.

Example 141

5-[5-(2-hydroxy-4-methoxy-phenyl)-isoxazol-3-yl]-pentanoic acid ethyl ester

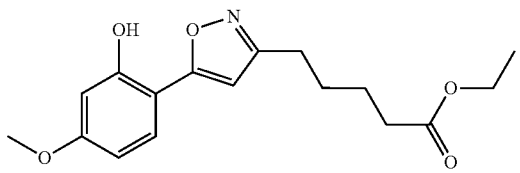 [SMILES: CCOC(=O)CCCCc1cc(-c2ccc(OC)cc2O)on1]

Add a solution of HCl (10 mL, conc.) in methanol (50 mL) to a rapidly stirred solution of 5-[5-(2-Hydroxy-4-methoxy-phenyl)-isoxazol-3-yl]-pentanoic acid ethyl ester (4.68 g, 10.4 mmol) in THF (75 mL) and methanol (75 mL). Stir at room temperature under N$_2$ overnight Quench reaction with saturated NaHCO$_3$ solution and extract with EtOAc (×3). Dry combined organic layers over MgSO$_4$ and concentrate. Adsorb on SiO$_2$ and purify the residue by flash chromatography on silica gel eluting with 5-100% EtOAc/hexanes to afford the title compound (2.25 g, 71%). MS (IS) 306 (M+1)$^+$.

Example 142

5-[5-(2-hydroxy-4-methoxy-phenyl)-isoxazol-3-yl]-pentanoic acid

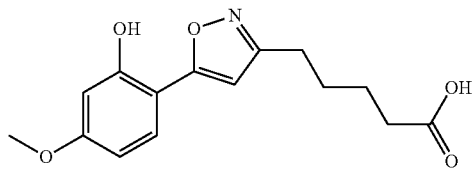 [SMILES: COc1ccc(-c2cc(CCCCC(=O)O)no2)c(O)c1]

Add a solution of LiOH (0.96 g, 40.0 mmol) in water (15 mL) to a rapidly stirred solution of 5-[5-(2-hydroxy-4-methoxy-phenyl)-isoxazol-3-yl]-pentanoic acid ethyl ester (2.45 g, 8.0 mmol) in dioxane (25 mL), stir at room temperature for 2 hours. Acidify to pH 1 with 5N HCl solution affording a white precipitate. Allow to cool to room temperature and add water. Filter out solids, wash with water, dry in a 50° C. vacuum oven for 3 hours to afford the title compound (1.86 g, 80%). MS (IS) 292 (M+1)$^+$.

Example 143

5-[4-(2-Hydroxy-phenyl)-oxazol-2-yl]-pentanoic acid disodium salt

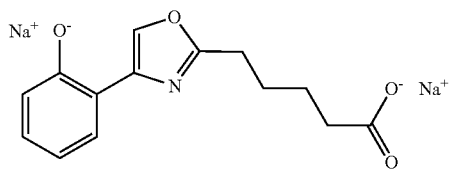 [SMILES: [Na+] ; O=C([O-])CCCCc1nc(-c2ccccc2[O-])co1 ; [Na+]]

Add a solution of NaOH (1.15 g, 28.75 mmol) in water (5 mL) to a suspension of 5-[4-(2-hydroxy-phenyl)-oxazol-2-yl]-pentanoic acid (compound of Example 6, 3.76 g, 14.38 mmol) in water (30 mL) and stir at room temperature. Heat to 50° C. for 1 h, filter hot solution, concentrate, place in 50-60° C. vacuum oven overnight Scrape and crush solids, place in 50-60° C. vacuum oven for 60 hours to afford the title compound (4.39 g, 100%). MS (IS) 260 (M−1)$^−$.

Example 144

5-{4-[2-(2,2,2-Trifluoro-acetylamino)-phenyl]-oxazol-2-yl}-pentanoic acid methyl ester

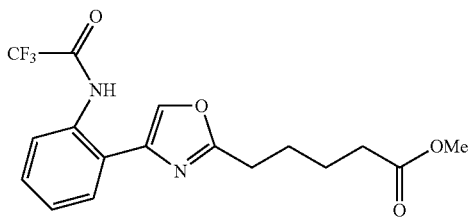 [SMILES: COC(=O)CCCCc1nc(-c2ccccc2NC(=O)C(F)(F)F)co1]

Dissolve 5-[4-(2-amino-phenyl)-oxazol-2-yl]-pentanoic acid methyl ester (1.4 g, 5.1 mmol) in Et$_2$O (25 mL) and add TEA (0.71 mL, 5.1 mmol). Cool the mixture in an ice bath, add trifluoroacetic anhydride (0.72 mL, 5.1 mmol) and allow the mixture to stir at 0° C. until reaction is complete. Quench the mixture with aq NaHCO$_3$ and extract with EtOAc. Dry the combined extracts over Na$_2$SO$_4$ and concentrate. Chromatograph the residue over silica gel (CH$_2$Cl$_2$) to allow for isolation of 5-{4-[2-(2,2,2-Trifluoro-acetylamino)-phenyl]-oxazol-2-yl}-pentanoic acid methyl ester (1.69 g, 89%). MS (ES): (M+1)$^+$ 371.1, 372.3 m/z.

Example 145

5-(4-{2-[Methyl-2,2,2-trifluoro-acetyl)-amino]-phenyl}-oxazol-2-yl)-pentanoic acid methyl ester Dissolve 5-{4-[2-(2,2,2-Trifluoro-acetylamino)-phenyl]-oxazol-2-yl}-pentanoic acid methyl ester (1.6 g, 4.3 mmol) in THF (25 mL) and stir at RT under nitrogen. Add sodium hydride in small portions (60%, 0.17 g, 4.3 mmol) and allow the mixture to stir until deprotonation is complete. Then add iodomethane (0.54 mL, 8.7 mmol) and heat at 50-60° C. until the reaction is complete. Concentrate the mixture and partition the residue between water and EtOAc. Dry the combined extracts over Na$_2$SO$_4$ and concentrate. Chromatograph the residue over silica gel (3% EtOAc/CH$_2$Cl$_2$) to allow for isolation of 5-(4-{2-[methyl-2,2,2-trifluoro-acetyl)-amino]-phenyl}-oxazol-2-yl)-pentanoic acid methyl ester (1.63 g, 98%). MS (ES): (M+1)$^+$ 385.1, 386.3 m/z.

Example 146

5-[4-(2-Methylamino-phenyl)-oxazol-2-yl]-pentanoic acid

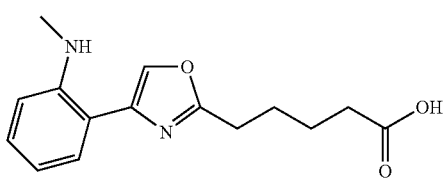 [SMILES: CNc1ccccc1-c1coc(CCCCC(=O)O)n1]

Combine 5-(4-{2-[Methyl-2,2,2-trifluoro-acetyl)-amino]-phenyl}-oxazol-2-yl)-pentanoic acid methyl ester (2.38 g, 6.2 mmol) with THF (2 mL), EtOH (4 mL) and 2N NaOH (12 mL) and stir until hydrolysis is complete. Concentrate the mixture, dilute the residue with water and adjust the pH to 4.0 with aq HCl. Extract the mixture with EtOAc and dry the extracts over $Na_2SO_4$ before concentrating. Chromatograph the residue over silica gel (3% EtOAc/$CH_2Cl_2$) to allow for recovery of 5-[4-(2-methylamino-phenyl)-oxazol-2-yl]-pentanoic acid (1.63 g, 96%). MS (ES): $(M+1)^+$ 275.1 m/z.

Preparation 25

4-[4-(2-nitro-phenyl)-oxazol-2-yl]-butyric acid methyl ester

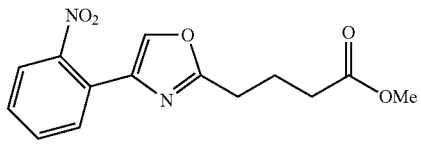 [SMILES: COC(=O)CCCc1nc(-c2ccccc2[N+](=O)[O-])co1]

Dissolve methyl (4-chloroformyl) butyrate (20 mL, 144 mmol) in dioxane (250 mL) and place the vessel in a RT water bath. Carefully bubble in ammonia gas (excess) and allow the mixture to stir for 1-2 h. Filter the mixture to remove solids. Suspend solids in $CHCl_3$ and filter again. Concentrate the combined filtrates and dry in vacuo to give 19.7 g (94%) of 4-carbamoyl-butyric acid methyl ester. MS (ES): $(M+Na)^+$ 168.1 m/z.

Combine 2-bromo-2'-nitroacetophenone (10.4 g, 42.6 mmol) with 4-carbamoyl-butyric acid methyl ester (12.2 g, 84.1 mmol) and heat the neat mixture in a sealed vessel at 120-150° C. for about 4-6 h. Cool the mixture, transfer to a round bottom flask with methanol and concentrate. Partition the residue between water and EtOAc. Dry the combined EtOAc extracts over $Na_2SO_4$ and concentrate. Initial chromatography over silica gel (EtOAc/$CH_2Cl_2$) followed by a second chromatography over silica gel (Hex/EtOAc) allowed for recovery of 4-[4-(2-nitro-phenyl)-oxazol-2-yl]-butyric acid methyl ester (3.05 g, 25%). MS (ES): $(M+1)^+$ 291.1, 292.2 m/z.

Example 147

4-[4-(2-amino-phenyl)-oxazol-2-yl]-butyric acid methyl ester

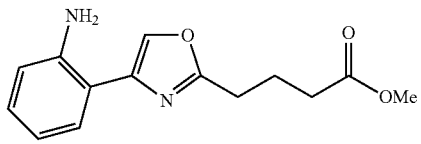 [SMILES: COC(=O)CCCc1nc(-c2ccccc2N)co1]

Combine 4-[4-(2-nitro-phenyl)-oxazol-2-yl]-butyric acid methyl ester (3.0 g, 10.3 mmol) with Pd/C (5%, 450 mg) and Pd/black (50 mg) in THF (150 mL) and react with hydrogen (init. 40 psi) in a Parr® apparatus. When reduction is complete, filter the mixture through Celite® and concentrate the filtrate. Drying allows for recovery of crude 4-[4-(2-amino-phenyl)-oxazol-2-yl]-butyric acid methyl ester (2.36 g, 88%). MS (ES): $(M+1)^+$ 261.2 m/z.

Example 149

4-[4-(2-amino-phenyl)-oxazol-2-yl]-butyric acid

Combine 4-[4-(2-amino-phenyl)-oxazol-2-yl]-butyric acid methyl ester (2.36 g, 9.1 mmol) with THF (3 mL), EtOH (3 mL) and 2N NaOH (20 mL) and stir until hydrolysis is complete. Concentrate the mixture, dilute the residue with water and adjust the pH to 3.5-4.0 with aq HCl. Extract the mixture with EtOAc and dry the extracts over $Na_2SO_4$ before concentrating. Chromatograph the residue over silica gel (MeOH/$CH_2Cl_2$) to allow for recovery of 4-[4-(2-amino-phenyl)-oxazol-2-yl]-butyric acid (1.63 g, 73%). MS (ES): $(M+1)^+$ 247.1 m/z.

Preparation 26

6-[4-(2-nitro-phenyl)-oxazol-2-yl]-hexanoic acid ethyl ester

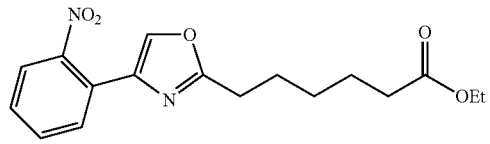

Using a method similar to the procedure described for the preparation of 4-carbamoyl-butyric acid methyl ester; 6-(chloroformyl) hexanoic acid ethyl ester (10.7 g, 55.4 mmol) in dioxane (150 mL) and ammonia gas give 6-carbamoyl-hexanoic acid ethyl ester (9.23 g, 96%). MS (ES): $(M+1)^+$ 174.1 m/z.

Using a method similar to the procedure described for the preparation of 4-[4-(2-nitro-phenyl)-oxazol-2-yl]-butyric acid methyl ester; reaction of 2-bromo-2'-nitroacetophenone (8.9 g, 36.5 mmol) with 6-carbamoyl-hexanoic acid ethyl ester (9.1 g, 48.7 mmol) gives 6-[4-(2-nitro-phenyl)-oxazol-2-yl]-hexanoic acid ethyl ester (3.19 g, 26%). MS (ES): $(M+1)^+$ 333.2, 334.4 m/z.

Example 150

6-[4-(2-amino-phenyl)-oxazol-2-yl]-hexanoic acid ethyl ester

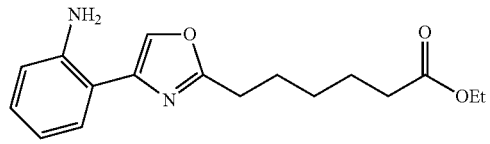 [SMILES: CCOC(=O)CCCCCc1nc(-c2ccccc2[N+](=O)[O-])co1]

Using a method similar to the procedure described for the preparation of 4-[4-(2-amino-phenyl)-oxazol-2-yl]-butyric acid; reduction of 6-[4-(2-nitro-phenyl)-oxazol-2-yl]-hexanoic acid ethyl ester (3.1 g, 9.3 mmol) gives crude 6-[4-(2-amino-phenyl)-oxazol-2-yl]-hexanoic acid ethyl ester (2.8 g, 99%). MS (ES): $(M+1)^+$ 303.3 m/z.

Example 151

6-[4-(2-amino-phenyl)-oxazol-2-yl]-hexanoic acid

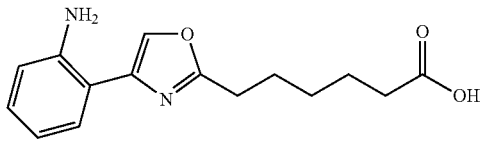 [SMILES: Nc1ccccc1-c1coc(CCCCCC(=O)O)n1]

Using a method similar to the procedure described for the preparation of 4-[4-(2-amino-phenyl)-oxazol-2-yl]-butyric acid; hydrolysis of 6-[4-(2-amino-phenyl)-oxazol-2-yl]-hexanoic acid ethyl ester (2.7 g, 8.9 mmol) gives 6-[4-(2-amino-phenyl)-oxazol-2-yl]-hexanoic acid (2.03 g, 83%). MS (ES): $(M+1)^+$ 274.9 m/z.

Preparation 27

3-[4-(2-nitro-phenyl)-oxazol-2-yl]-propionic acid methyl ester

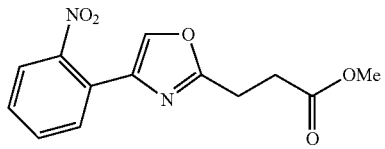 [SMILES: COC(=O)CCc1nc(-c2ccccc2[N+](=O)[O-])co1]

Using a method similar to the procedure described for the preparation of 4-carbamoyl-butyric acid methyl ester; methyl-4-chloro-4-oxobutyrate (25 mL, 204.5 mmol) in dioxane (250 mL) and ammonia gas gives succinamic acid methyl ester (24.5 g, 91%). MS (ES): $(M+Na)^+$ 154.1 m/z.

Using a method similar to the procedure described for the preparation of 4-[4-(2-nitro-phenyl)-oxazol-2-yl]-butyric acid methyl ester; reaction of 2-bromo-2'-nitroacetophenone (15.43 g, 63.2 mmol) with succinamic acid methyl ester (14.4 g, 110 mmol) gives 3-[4-(2-nitro-phenyl)-oxazol-2-yl]-propionic acid methyl ester (6.24 g, 36%). MS (ES): $(M+1)^+$ 277.1 m/z.

Example 152

3-[4-(2-amino-phenyl)-oxazol-2-yl]-propionic acid methyl ester

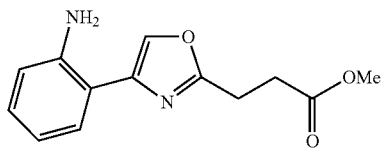

Using a method similar to the procedure described for the preparation of 4-[4-(2-amino-phenyl)-oxazol-2-yl]-butyric acid; reduction of 3-[4-(2-nitro-phenyl)-oxazol-2-yl]-propionic acid methyl ester (6.2 g, 9.3 mmol) in EtOAc gives 3-[4-(2-amino-phenyl)-oxazol-2-yl]-propionic acid methyl ester (2.9 g, 52%) after chromatography over silica gel (THF/hexanes). MS (ES): $(M+1)^+$ 247.3 m/z.

Example 153

3-[4-(2-amino-phenyl)-oxazol-2-yl]-propionic acid

Using a method similar to the procedure described for the preparation of 4-[4-(2-amino-phenyl)-oxazol-2-yl]-butyric acid; hydrolysis of 3-[4-(2-amino-phenyl)-oxazol-2-yl]-propionic acid methyl ester (4.8 g, 19.5 mmol) gives 3-[4-(2-amino-phenyl)-oxazol-2-yl]-propionic acid (3.84 g, 85%) after chromatography over silica gel (MeOH/$CH_2Cl_2$). MS (ES): $(M+1)^+$ 233.1 m/z.

Preparation 28

2-Bromo-1-(5-chloro-2-methoxy-phenyl)-ethanone

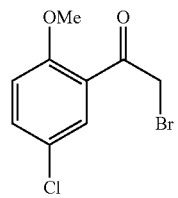 [SMILES: COc1ccc(Cl)cc1C(=O)CBr]

Combine 5'-chloro-2'-hydroxyacetophenone (17.0 g, 100 mmol) with potassium carbonate (15.1 g, 109 mmol) and iodomethane (12.5 mL, 200 mmol) in DMF and stir in a sealed vessel overnight at RT. Remove DMF and partition the residue between water and EtOAc. Dry the combined extracts over $Na_2SO_4$ and concentrate. Chromatograph the resulting residue over silica gel (EtOAc/hexanes) to allow for isolation of 1-(5-Chloro-2-methoxy-phenyl)-ethanone (17.1 g, 93%). MS (ES): $(M+1)^+$ 185.1, 187.1 m/z.

Dissolve 1-(5-Chloro-2-methoxy-phenyl)-ethanone (8.5 g, 46.2 mmol) in $CHCl_3$ (40 mL) and add this mixture to a warmed slurry of $CuBr_2$ (20.6 g, 92.4 mmol) in EtOAc (150 mL). Heat the resulting mixture near reflux for approx. 3 h. Cool and filter the mixture and concentrate the resulting filtrate. Chromatograph the resulting residue over silica gel ($CH_2Cl_2$) to allow for isolation of 2-bromo-1-(5-chloro-2-methoxy-phenyl)-ethanone (12.0 g, 99%). MS (ES): $(M+1)^+$ 185.1, 187.1 m/z.

Example 154

5-[4-(5-Chloro-2-methoxy-phenyl)-oxazol-2-yl]-pentanoic acid methyl ester

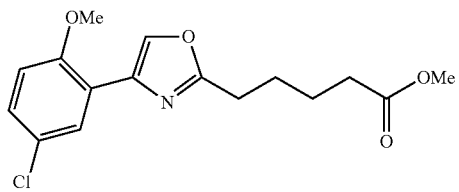 [SMILES: COC(=O)CCCCc1nc(-c2cc(Cl)ccc2OC)co1]

Combine 2-bromo-1-(5-chloro-2-methoxy-phenyl)-ethanone (12.0 g, 46 mmol) with 5-carbamoyl-pentanoic acid methyl ester (12.7 g, 79.9 mmol) and heat the neat mixture in a sealed vessel at 120-140° C. for about 6 h. Cool the mixture and add methanol and allow the mixture to stir overnight at room temperature. Concentrate the mixture and partition the residue between aq NaHCO₃ and EtOAc. Dry the combined extracts over Na₂SO₄ and concentrate. Chromatography over silica gel (CHCl₃) allows for recovery of 5-[4-(5-chloro-2-methoxy-phenyl)-oxazol-2-yl]-pentanoic acid methyl ester (5.5 g, 37%). MS (ES): (M+1)⁺ 324.1, 326.1 m/z.

Example 155

5-[4-(5-Chloro-2-hydroxy-phenyl)-oxazol-2-yl]-pentanoic acid

Dissolve 5-[4-(5-Chloro-2-methoxy-phenyl)-oxazol-2-yl]-pentanoic acid methyl ester (0.32 g, 1.0 mmol) in CH₂Cl₂ (2 mL) under nitrogen at RT. Add boron tribromide (1M in CH₂Cl₂, 3 mL) and stir at RT until the reaction is complete. Quench the mixture into water and extract with EtOAc. Dry the combined extracts over Na₂SO₄ and concentrate. Chromatograph the resulting residue over silica gel (MeOH/CH₂Cl₂) to allow for isolation of 5-[4-(5-chloro-2-hydroxy-phenyl)-oxazol-2-yl]-pentanoic acid (0.27 g, 91%). MS (ES): (M+1)⁺ 296.1, 298.1 m/z.

Example 156

5-[4-(5-Chloro-2-hydroxy-phenyl)-oxazol-2-yl]-pentanoic acid disodium salt

Combine 5-[4-(5-Chloro-2-hydroxy-phenyl)-oxazol-2-yl]-pentanoic acid (2.71 g, 9.2 mmol) with THF (10 mL), MeOH (10 mL) and 1N NaOH (18.4 mL) and stir at RT for 2 h. Concentrate the mixture and dry the residue overnight in vacuo at 40-50° C. to allow for recovery of 5-[4-(5-Chloro-2-hydroxy-phenyl)-oxazol-2-yl]-pentanoic acid disodium salt (3.0 g, 96%). MS (ES): (M+1)⁺ 296.1, 298.1 m/z.

Preparation 29

2-Bromo-1-(2-methoxy-phenyl)-propan-1-one

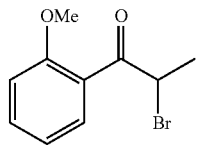

Combine 2'-hydroxypropiophenone (4.55 mL, 33.3 mmol) with cesium carbonate (11 g, 33.7 mmol) and iodomethane (4.1 mL, 65.8 mmol) in acetone (100 mL) and stir in a sealed vessel at RT until the reaction is complete. Concentrate the mixture and partition residue between water and EtOAc. Dry the combined extracts over Na₂SO₄ and concentrate. Chromatograph the resulting residue over silica gel (EtOAc/hexanes) to allow for isolation of 1-(2-methoxy-phenyl)-propan-1-one (5.01 g, 93%). MS (ES): (M+1)⁺ 165.1 m/z.

Dissolve 1-(2-methoxy-phenyl)-propan-1-one (5.0 g, 30.5 mmol) in CHCl₃ (25 mL) and add this mixture to a warmed slurry of CuBr₂ (13.6 g, 60.1 mmol) in EtOAc (75 mL). Heat the resulting mixture near reflux for approx. 3 h. Cool and filter the mixture and concentrate the resulting filtrate. Chromatograph the resulting residue over silica gel (CH₂Cl₂) to allow for isolation of 2-bromo-1-(2-methoxy-phenyl)-propan-1-one (7.32 g, 99%). MS (ES): (M+1)⁺ 243.0, 245.0 m/z.

Example 157

5-[4-(2-methoxy-phenyl)-5-methyl-oxazol-2-yl]-pentanoic acid methyl ester

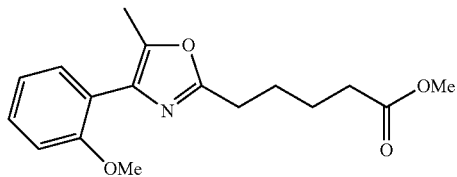 [SMILES: COC(=O)CCCCc1nc(-c2ccccc2OC)c(C)o1]

Combine 2-Bromo-1-(2-methoxy-phenyl)-propan-1-one (7.25 g, 29.8 mmol) with 5-carbamoyl-pentanoic acid methyl ester (9.5 g, 60.5 mmol) and heat the neat mixture in a sealed vessel at 140-150° C. for about 4 h. Cool the mixture, transfer to a flask using methanol and concentrate. Partition the residue between water and EtOAc. Dry the combined extracts over Na₂SO₄ and concentrate. Chromatography over silica gel (MeOH/CH₂Cl₂) allows for recovery of 5-[4-(2-methoxy-phenyl)-5-methyl-oxazol-2-yl]-pentanoic acid methyl ester (3.63 g, 40%). MS (ES): (M+1)⁺ 304.2 m/z.

Example 158

5-[4-(2-hydroxy-phenyl)-5-methyl-oxazol-2-yl]-pentanoic acid methyl ester

Dissolve 5-[4-(2-methoxy-phenyl)-5-methyl-oxazol-2-yl]-pentanoic acid methyl ester (3.5 g, 11.5 mmol) in CH₂Cl₂ (50 mL) under nitrogen at RT. Add boron tribromide (1M in CH₂Cl₂, 29 mL) and stir at RT until the reaction is complete. Quench the mixture into ice/water and extract with CH₂Cl₂. Dry the combined extracts over Na₂SO₄ and concentrate. Chromatograph the resulting residue over silica gel (MeOH/CH₂Cl₂) to allow for isolation of 5-[4-(2-hydroxy-phenyl)-5-methyl-oxazol-2-yl]-pentanoic acid methyl ester (2.61 g, 78%). MS (ES): (M+1)⁺ 290.2 m/z.

Example 159

5-[4-(2-hydroxy-phenyl)-5-methyl-oxazol-2-yl]-pentanoic acid

Combine 5-[4-(2-hydroxy-phenyl)-5-methyl-oxazol-2-yl]-pentanoic acid methyl ester (2.9 g, 10.0 mmol) with THF (3 mL), EtOH (3 mL) and 2N NaOH (20 mL) and stir until hydrolysis is complete. Concentrate the mixture, dilute the residue with water and adjust the pH to 2.0-3.0 with aq HCl. Extract the mixture with EtOAc and dry the extracts over Na₂SO₄ before concentrating. Chromatograph the residue over silica gel (MeOH/CH₂Cl₂) to allow for recovery of 5-[4-(2-hydroxy-phenyl)-5-methyl-oxazol-2-yl]-pentanoic acid (2.14 g, 78%). MS (ES): (M+1)⁺ 276.2 m/z.

Preparation 30

Mixture of 7-Bromo-6-oxo-heptanoic acid methyl ester and 5-Bromo-6-oxo-heptanoic acid methyl ester

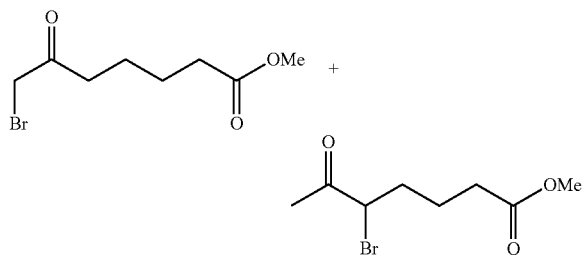

Dissolve 5-acetyl valeric acid (16.0 g, 111.1 mmol) in MeOH (200 mL) and warm the mixture near 50° C. Add bromine (5.7 mL, 111.1 mmol) and heat the mixture at reflux for 3 hours. Concentrate the mixture and dissolve the resulting oil in $Et_2O$. Wash the organic solution with water and aqueous $NaHCO_3$ and dry over $Na_2SO_4$. Concentration gives the crude mixture of 7-bromo-6-oxo-heptanoic acid methyl ester and 5-bromo-6-oxo-heptanoic acid methyl ester (25.3 g, 96%).

Preparation 31

2-Methoxy-thiobenzamide

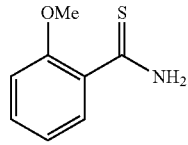 [SMILES: COc1ccccc1C(N)=S]

Combine 2-methoxy benzamide (10.0 g, 66.2 mmol) with phosphorus pentasulfide (10.1 g, 22.7 mmol) and THF (200 mmol) in a sealed vessel and stir for 30 minutes at room temperature. Sonicate the mixture for 1 hour and then allow the mixture to stand at room temperature. Decant the THF solution from the solids and concentrate. Chromatograph the resulting residue over silica gel (MeOH/$CH_2Cl_2$) to give 2-methoxy-thiobenzamide (7.05 g, 64%).

Example 160

5-[2-(2-methoxy-phenyl)-thiazol-4-yl]-pentanoic acid methyl ester

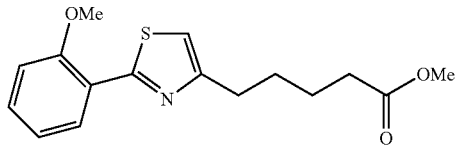 [SMILES: COC(=O)CCCCc1csc(-c2ccccc2OC)n1]

Combine 2-methoxy-thiobenzamide (3.5 g, 21 mmol) with the bromide mixture described in Preparation 30 (5.6 g, 23.7 mmol) in THF (100 mL) and heat the mixture near reflux for about 3 hours. Concentrate the mixture in vacuo. Dissolve the residue in EtOAc, wash with water and aqueous $NaHCO_3$, and dry over $Na_2SO_4$. Concentrate the solution and chromatograph the residue over silica gel (EtOAc/hexanes) to recover 5-[2-(2-methoxy-phenyl)-thiazol-4-yl]-pentanoic acid methyl ester (4.4 g, 69%). MS (ES): $(M+1)^+$ 306.2, 307.2 m/z.

Example 161

5-[2-(2-hydroxy-phenyl)-thiazol-4-yl]-pentanoic acid methyl ester

Dissolve 5-[2-(2-methoxy-phenyl)-thiazol-4-yl]-pentanoic acid methyl ester (3.3 g, 10.8 mmol) in $CH_2Cl_2$ (30 mL) under nitrogen at room temperature. Add boron tribromide (1M in $CH_2Cl_2$, 27 mL) and stir at room temperature until the reaction is complete. Quench the mixture with methanol, add ice/water and extract with $CH_2Cl_2$. Dry the combined extracts over $Na_2SO_4$ and concentrate. Chromatograph the resulting residue over silica gel (EtOAc/$CH_2Cl_2$) to allow for isolation of 5-[2-(2-hydroxy-phenyl)-thiazol-4-yl]-pentanoic acid methyl ester (2.2 g, 70%). MS (ES): $(M+1)^+$ 292.1 m/z.

Example 162

5-[2-(2-hydroxy-phenyl)-thiazol-4-yl]-pentanoic acid

Combine 5-[2-(2-hydroxy-phenyl)-thiazol-4-yl]-pentanoic acid methyl ester (2.2 g, 7.6 mmol) with THF (2.5 mL), EtOH (2.5 mL) and 2N NaOH (14 mL) and stir until hydrolysis is complete. Concentrate the mixture, dilute the residue with water and adjust the pH to 2.0-3.0 using aqueous HCl. Extract the mixture with EtOAc and dry the extracts over $Na_2SO_4$ before concentrating. Chromatograph the residue over silica gel (MeOH/$CH_2Cl_2$) to allow for recovery of 5-[2-(2-hydroxy-phenyl)-thiazol-4-yl]-pentanoic acid (1.5 g, 72%). MS (ES): $(M+1)^+$ 278.1 m/z.

Preparation 32

Mixture of 2-Methoxy-benzoic acid 6-methoxycarbonyl-2-oxo-hexyl ester and 2-Methoxy-benzoic acid 1-acetyl-4-methoxycarbonyl-butyl ester

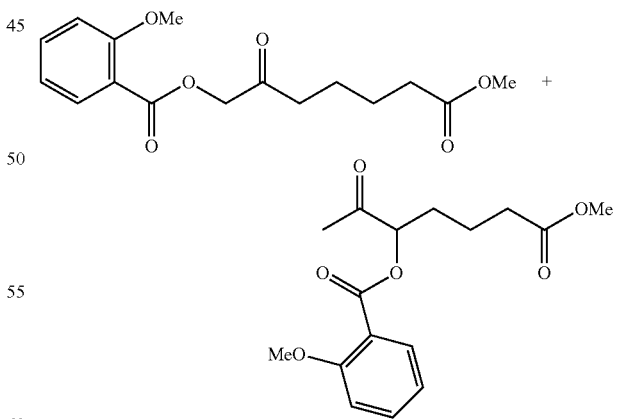

Combine o-anisic acid (7.0 g, 46 mmol) with $Na_2CO_3$ (2.44 g, 23 mmol) in water (50 mL) and heat at 50° C. until everything is in solution. Then, add the bromide mixture described in Preparation 30 (10.91 g, 46 mmol) in EtOH (100 mL) and heat the mixture near reflux for about 5 hours. After allowing the mixture to cool and stir overnight, concentrate the mixture, add water, and extract with EtOAc. Dry the combined extracts over Na$_2$SO$_4$. Concentrate the solution and chromatograph the residue over silica gel (EtOAc/hexanes) to recover a mixture of 2-methoxy-benzoic acid 6-methoxycarbonyl-2-oxo-hexyl ester and 2-methoxy-benzoic acid acetyl-4-methoxycarbonyl-butyl ester (13.0 g, 92%). MS (ES): (M+1)$^+$ 309.1 m/z.

Examples 163 and 164

5-[2-(2-Methoxy-phenyl)-oxazol-4-yl]-pentanoic acid methyl ester

4-[2-(2-methoxy-phenyl)-4-methyl-oxazol-5-yl]-butyric acid methyl ester

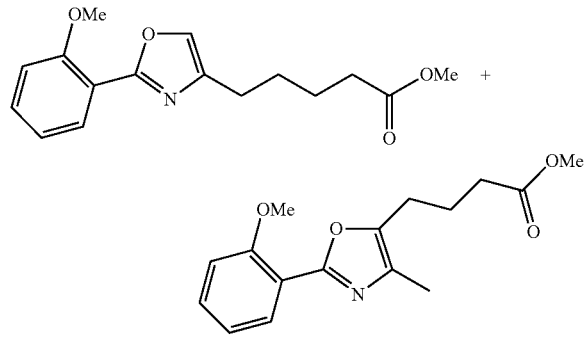

Combine the mixture described in Preparation 32 (15 g, 48.7 mmol) with ammonium acetate (11.25 g, 146 mmol) in HOAc (40 mL) and heat the mixture at 120-140° C. for about 5 h. Cool the mixture and concentrate once from MeOH and once from hexanes. Dilute the residue with water and extract with EtOAc. Wash the combined extracts with 3× aqueous NaHCO$_3$, and dry over Na$_2$SO$_4$. Concentrate the solution and chromatograph the residue over silica gel (EtOAc/hexanes) to allow for separation of 5-[2-(2-methoxy-phenyl)-oxazol-4-yl]-pentanoic acid methyl ester (1.0 g, 7%, MS (ES): (M+1)$^+$ 290.1 m/z) and 4-[2-(2-methoxy-phenyl)-4-methyl-oxazol-5-yl]-butyric acid methyl ester (3.9 g, 28%), MS (ES): (M+1)$^+$ 290.1 m/z.

Example 165

4-[2-(2-hydroxy-phenyl)-4-methyl-oxazol-5-yl]-butyric acid methyl ester

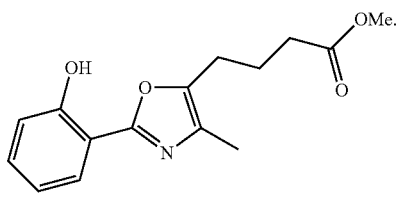 [SMILES: COC(=O)CCCc1oc(-c2ccccc2O)nc1C]

Dissolve 4-[2-(2-methoxy-phenyl)-4-methyl-oxazol-5-yl]-butyric acid methyl ester (2.1 g, 7.3 mmol) in CH$_2$Cl$_2$ (20 mL) under nitrogen at room temperature. Add boron tribromide (1M in CH$_2$Cl$_2$, 21.8 mL) and stir at room temperature until the reaction is complete. Quench the mixture with methanol, add water and extract with CH$_2$Cl$_2$. Dry the combined extracts over Na$_2$SO$_4$ and concentrate. Chromatograph the resulting residue over silica gel (MeOH/CH$_2$Cl$_2$) to allow for isolation of 4-[2-(2-hydroxy-phenyl)-4-methyl-oxazol-5-yl]-butyric acid methyl ester (1.55 g, 77%). MS (ES): (M+1)$^+$ 276.1, 277.2 m/z.

Example 166

4-[2-(2-hydroxy-phenyl)-4-methyl-oxazol-5-yl]-butyric acid

Using a method similar to that described in Example 162, hydrolysis of 4-[2-(2-hydroxy-phenyl)-4-methyl-oxazol-5-yl]-butyric acid methyl ester (2.75 g, 10 mmol) gives 2.31 g of 4-[2-(2-hydroxy-phenyl)-4-methyl-oxazol-5-yl]-butyric acid (88%) after purification. MS (ES): (M+1)$^+$ 262.0, 263.2 m/z Example 167

5-[2-(2-hydroxy-phenyl)-oxazol-4-yl]-pentanoic acid methyl ester

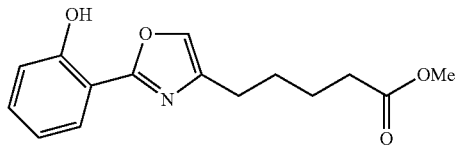 [SMILES: COC(=O)CCCCc1coc(-c2ccccc2O)n1]

Using a method similar to that described in Example 165, 5-[2-(2-methoxy-phenyl)-oxazol-4-yl]-pentanoic acid methyl ester (1.65 g, 5.7 mmol) with boron tribromide (1.0 M in CH$_2$Cl$_2$, 17.2 mL) in CH$_2$Cl$_2$ gives 5-[2-(2-hydroxy-phenyl)-oxazol-4-yl]-pentanoic acid methyl ester (0.76 g, 48%). MS (ES): (M+1)$^+$ 276.1, 277.2 m/z.

Example 168

5-[2-(2-hydroxy-phenyl)-oxazol-4-yl]-pentanoic acid

Using a method similar to that described in Example 162, hydrolysis of 5-[2-(2-hydroxy-phenyl)-oxazol-4-yl]-pentanoic acid methyl ester (1.45 g, 5.3 mmol) gives 5-[2-(2-hydroxy-phenyl)-oxazol-4-yl]-pentanoic acid (1.19 g, 86%) after purification. MS (ES): (M+1)$^+$ 262.1 m/z.

Preparation 33

Mixture of 7-(2-methoxy-benzoylamino)-6-oxo-heptanoic acid methyl ester 5-(2-methoxy-benzoylamino)-6-oxo-heptanoic acid methyl ester

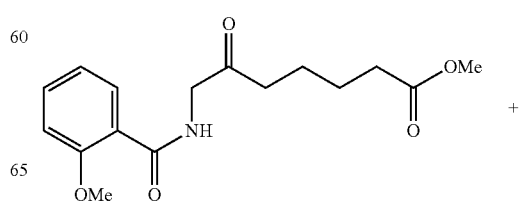

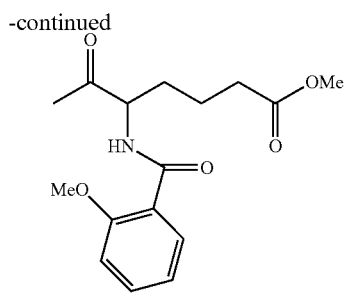

Dissolve di-t-butyliminodicarboxylate (3.67 g, 16.9 mmol) in DMF (25 mL) under $N_2$ at RT and add NaH (60%, 0.75 g, 18.6 mmol). Stir the mixture until deprotonation is complete and add the bromide mixture (4.0 g, 16.9 mmol) described in Preparation 30 and heat the mixture overnight near 50° C. Dilute the mixture with water and extract with EtOAc. Wash the combined extracts with water and brine and dry over $Na_2SO_4$. Concentration and chromatography of the residue over silica gel (MeOH/$CH_2Cl_2$) gives a mixture of 7-di-tert-butoxycarbonylamino-6-oxo-heptanoic acid methyl ester and 5-di-tert-butoxycarbonylamino-6-oxo-heptanoic acid methyl ester (5.6 g, 89%). MS (ES): $(M+NH_4)^+$ 391.2 m/z.

Treat a mixture of 7-di-tert-butoxycarbonylamino-6-oxo-heptanoic acid methyl ester and 5-di-tert-butoxycarbonylamino-6-oxo-heptanoic acid methyl ester (7.5 g, 20 mmol) with $Et_2O/HCl$ and stir the resulting mixture overnight at room temperature. Concentration and drying in vacuo gives a mixture of 7-amino-6-oxo-heptanoic acid methyl ester and 5-amino-6-oxo-heptanoic acid methyl ester hydrochlorides (4.1 g, 97%). MS (ES): $(M+1)^+$ 174.1 m/z.

Combine a mixture of 7-amino-6-oxo-heptanoic acid methyl ester and 5-amino-6-oxo-heptanoic acid methyl ester hydrochlorides (2.36 g, 11.3 mmol) with o-anisic acid (1.71 g, 11.3 mmol), 1-(dimethylaminopropyl)-3-ethylcarbodiimide hydrochloride (2.16 g, 11.3 mmol), 1-hydroxybenzotriazole hydrate (11.3 mmol), N,N-diisopropylethylamine (5.88 mL, 33.8 mmol) in DMF and stir for 24-48 hours. Dilute the mixture with water and extract with EtOAc. Wash the combined extracts with brine and dry over $Na_2SO_4$ before concentrating. Chromatograph the residue over silica gel (MeOH/$CH_2Cl_2$) to allow for isolation of a mixture of 7-(2-methoxy-benzoylamino)-6-oxo-heptanoic acid methyl ester and 5-(2-methoxy-benzoylamino)-6-oxo-heptanoic acid methyl ester (3.45 g, 99%). MS (ES): $(M+1)^+$ 308.1 m/z.

Example 169

5-[2-(2-methoxy-phenyl)-oxazol-5-yl]-pentanoic acid methyl ester

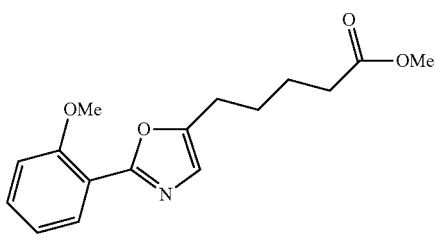 [SMILES: COC(=O)CCCCc1cnc(-c2ccccc2OC)o1]

Combine the mixture of Preparation 33 (2.9 g, 9.5 mmol) with phosphorus oxychloride (2.6 mL, 28.5 mmol) in DMF (15 mL) and heat the mixture at about 90° C. for 1 hour. Cool the mixture, dilute with water and extract with EtOAc. Wash the combined extracts with brine and dry over $Na_2SO_4$. Concentrate the solution and chromatograph the residue over silica gel (EtOAc/hexanes) to allow for separation of 5-[2-(2-methoxy-phenyl)-oxazol-5-yl]-pentanoic acid methyl ester (0.96 g, 35%). MS (ES): $(M+1)^+$ 290.1 m/z.

Example 170

5-[2-(2-methoxy-phenyl)-oxazol-5-yl]-pentanoic acid

Combine 5-[2-(2-methoxy-phenyl)-oxazol-5-yl]-pentanoic acid methyl ester (2.1 g, 7.3 mmol) with THF (4 mL), EtOH (4 mL) and 2N NaOH (15 mL) and stir until hydrolysis is complete. Concentrate the mixture, dilute the residue with water and adjust the pH to 3.0-4.0 using aq HCl. Extract the mixture with $CH_2Cl_2$ and concentrate the extracts in vacuo. Drying gives 5-[2-(2-methoxy-phenyl)-oxazol-5-yl]-pentanoic acid (1.8 g, 91%). MS (ES): $(M+1)^+$ 274.1, 275.1 m/z.

Example 171

5-[2-(2-hydroxy-phenyl)-oxazol-5-yl]-pentanoic acid

Dissolve 5-[2-(2-methoxy-phenyl)-oxazol-5-yl]-pentanoic acid (1.75 g, 6.4 mmol) in $CH_2Cl_2$ (20 mL) under nitrogen at room temperature. Add boron tribromide (1M in $CH_2Cl_2$, 15 mL) and stir at room temperature until the reaction is complete. Cool the mixture, quench with water/methanol (95/5) and extract with $CH_2Cl_2$. Dry the combined extracts over $Na_2SO_4$ and concentrate. Resubject the residue to hydrolysis conditions as described in Preparation 14. Chromatograph the resulting residue over silica gel (MeOH/$CH_2Cl_2$) to allow for isolation of 5-[2-(2-hydroxy-phenyl)-oxazol-5-yl]-pentanoic acid (1.45 g, 87%). MS (ES): $(M+1)^+$ 262.1, 263.2 m/z.

Preparation 34

2-Bromo-1-(2-trifluoromethyl-phenyl)-ethanone

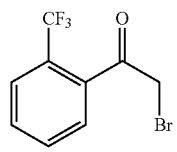 [SMILES: O=C(CBr)c1ccccc1C(F)(F)F]

Dissolve 2'-(trifluoromethyl)-acetophenone (5.0 g, 26.6 mmol) in $CHCl_3$ (25 mL) and add this mixture to a warmed slurry of $CuBr_2$ (11.86 g, 53.2 mmol) in EtOAc (75 mL). Heat the resulting mixture near reflux for approx. 5 hours. Cool and filter the mixture and concentrate the resulting filtrate. Chromatograph the resulting residue over silica gel ($CH_2Cl_2$) to allow for isolation of 2-Bromo-1-(2-trifluoromethyl-phenyl)-ethanone (6.6 g, 93%).

Example 172

5-[4-(2-trifluoromethyl-phenyl)-oxazol-2-yl]-pentanoic acid methyl ester

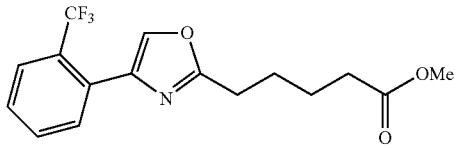 [SMILES: COC(=O)CCCCc1nc(-c2ccccc2C(F)(F)F)co1]

Combine 2-bromo-1-(2-trifluoromethyl-phenyl)-ethanone (6.6 g, 24.7 mmol) with 5-carbamoyl-pentanoic acid methyl ester (7.8 g, 49 mmol) and heat the neat mixture in a sealed vessel at 140-150° C. for about 4.5 hours. Cool the mixture, dilute with water, and extract with EtOAc. Dry the combined extracts over $Na_2SO_4$ and concentrate. Chromatography over silica gel ($CH_2Cl_2$) allows for recovery of 5-[4-(2-trifluoromethyl-phenyl)-oxazol-2-yl]-pentanoic acid methyl ester (3.47 g, 43%). MS (ES): $(M+1)^+$ 328.2 m/z.

Example 173

5-[4-(2-trifluoromethyl-phenyl)-oxazol-2-yl]-pentanoic acid

Combine 5-[4-(2-trifluoromethyl-phenyl)-oxazol-2-yl]-pentanoic acid methyl ester (3.35 g, 9.9 mmol) with THF (3 mL), EtOH (3 mL) and 2N NaOH (15 mL) and stir until hydrolysis is complete. Concentrate the mixture, dilute the residue with water and adjust the pH to 3.0-4.0 using aq HCl. Extract the mixture with EtOAc and dry the extracts over $Na_2SO_4$ before concentrating. Chromatograph the residue over silica gel (MeOH/$CH_2Cl_2$) to allow for recovery of 5-[4-(2-trifluoromethyl-phenyl)-oxazol-2-yl]-pentanoic acid (2.36 g, 76%). MS (ES): $(M+1)^+$ 314.2 m/z.

Formulation

Because the compound of formula II may contain a basic and/or acidic moiety (i.e., amino and/or carboxylic acid), said compound may be formulated as a pharmaceutical salt, e.g., as the sodium or hydrochloride salt or as a salt described in "Handbook of Pharmaceutical Salts: Properties, Selection and Use", Weinheim, N.Y.: VHCA; Wiley-VCH, 2002. The compound of formula II is preferably formulated in a dosage unit form, i.e., in an individual delivery vehicle, for example, a tablet or capsule, prior to administration to the recipient patient. Therefore, yet another embodiment of the present invention is a pharmaceutical composition comprising a compound of formula II, or a pharmaceutical salt thereof, an active agent, and a pharmaceutical carrier.

The present pharmaceutical compositions are prepared by known procedures using well-known and readily available ingredients. In making the formulations of the present invention, the delivery agent (formula II compound) will be mixed with an active agent and will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient.

Biological Assays

Delivery Agent Formulation Development

For oral dosing of a GLP-1 compound, a pH range of 7.4 to 8.4 for each formulation is typically employed, whereas for a MC4 agonist peptide, a pH range of 6.8-7.2 (most typically 7.0) for the formulation of is typically utilized. A target delivery agent concentration of 150 mg/mL in both cases is also typical. Initial feasibility studies are conducted to determine final carrier formulations.

Briefly, 200 mg of delivery agent is weighed into a Type I glass vial, to which 1 mL of MilliQ water is added. Each mixture is visually inspected for solubility, followed by addition of NaOH to increase solubility or HCl to decrease the pH to the oral dose range. Formulations are then diluted to 150 mg/mL with MilliQ water. Using this approach, the formulations generally fell into three categories: aqueous soluble, nearly completely soluble (e.g., few undissolved particles remaining, very fine aqueous suspensions or hazy suspensions), and aqueous insoluble (e.g., heavy suspensions). Delivery agents that exhibited aqueous insolubility are formulated in 4% w/v (aqueous) hydroxypropylcellulose (Klucel® LF, Hercules, Wilmington, Del.) as needed. In these cases, between 50 and 100 mg of agent is suspended in Klucel® LF in a Type I glass vial, to yield a concentration of 200 mg/mL. For heavy aqueous and Klucel® LF suspensions, the preparations are cooled on ice for 3 minutes, followed by probe sonication on ice for 30 minutes using a Misonix Sonicator® Ultrasonic Processor XL ($^3/_{16}{}^{th}$ inch microtip) to reduce particle size. Following pH adjustment with NaOH or HCl, the formulations are then diluted to 150 mg/mL with MilliQ water or Klucel® LF.

Formulation of Stock Active Agent Solution

The GLP-1 compounds (e.g., $Val^8$-$Glu^{22}$-GLP-1(7-37)OH and $Val^8$-$Glu^{22}$-$I^{33}$-GLP-1(7-37)OH) and MC4 agonist peptides (e.g., Ac-Arg-cyclo[Cys-Glu-His-D-Phe-Arg-Trp-Cys]-$NH_2$; Ac-cyclo[hCys-His-D-Phe-Arg-Trp-Cys]-$NH_2$; Ac-cyclo[hCys-His-D-Phe-Arg-Trp-penicillamine]—$NH_2$; and N-cyclohexanecarbonyl-cyclo[hCys-His-D-Phe-Arg-Trp-penicillamine]-$NH_2$) used herein are described in PCT Publication Number WO 03/072195 and PCT Patent Application No. PCT/US04/16625, filed June 17, respectively.

A stock solution of GLP-1 compound active agent is prepared as follows. Briefly, a known quantity of lyophilized active agent is weighed into a Type I glass vial. MilliQ water is then added to yield an initial concentration of about 7-10 mg/mL. Complete solubility of the peptide is achieved by slowly raising the pH of the medium to 10.5 with 1 N NaOH and 5 N NaOH, followed by incubation at room temperature for 30 minutes. A volume of 1 M Tris buffer, pH 8.0 is added to give a final buffer concentration of 20 mM Tris, and the pH adjusted to pH 7.8 with 1N HCl and 5 N HCl. The solution is then filtered through a low protein binding 0.22 μM syringe filter (Millex GV, Millipore). The concentration of the peptide filtrate is determined by UV spectroscopy (λ max=280 nm). The solution is then diluted to a stock concentration of about 5.0 mg/mL using 20 mM Tris buffer, pH 7.8. The active agent solution is stored in 1.0 mL aliquots at −70° C. until used.

A stock solution of MC4R agonist peptide is prepared as follows. Briefly, a known quantity of lyophilized MC4R agonist peptide is weighed into a Type I glass vial. MilliQ water is then added to yield an initial concentration of about 19-21 mg/mL. The pH is raised to 6.0 with 1 N NaOH and 5 N NaOH, followed by incubation at room temperature for 30 minutes. The concentration of the peptide solution is determined by UV spectroscopy (max=280 nm; light scatter correction applied between 250 nm and 410 nm). The solution is then stored as a stock, concentration of about 20.0 mg/mL. The peptide solution is stored, refrigerated 4-8° C. until used.

Rat Oral Delivery Method

Male Sprague-Dawley (femoral artery cannulated, Charles River, Wilmington, Mass.) rats weighing 250-300 g are used in these studies. Animals are housed in single house stainless steel cages and cared for according to Eli Lilly and Company Animal Care and Use Policies & Procedures. Animals are fasted for at least 12 hours (with free access to water) before dose administration. Each experiment (delivery agent+active agent) is conducted in a group of four rats. Final formulations for each delivery agent are freshly prepared approximately 5-10 minutes prior to in vivo dosing.

Specifically, delivery agent formulation (~165 mg/mL stock) and GLP-1 compound active agent solution (~5.0 mg/mL stock) are added together to yield an admixture of delivery agent+active agent. The final concentrations in each such formulation are 150 mg/mL and 0.5 mg/mL, respectively. Formulations are dosed by oral gavage (PO) for a final dose of 300 mg/kg delivery agent and 1.0 mg/kg active agent. One mL of blood samples is collected in EDTA tubes from the systemic (femoral artery) cannula from each animal (one sample/time point) at 5, 10, and 20 minutes. Tubes are chilled on ice immediately following collection and centrifuged at approximately 5° C./3,000 rpm/15 minutes. Plasma is removed, transferred into 12×75 mm polypropylene sample tubes with snap caps, and stored immediately at −70° C. until analyzed by a radioimmunoassay.

In the case of an MC4 agonist peptide active agent, delivery agent formulation (~165 mg/mL stock) and peptide solution (~20.0 mg/mL stock) are added together to yield an admixture of delivery agent+active agent. The final concentrations in each such formulation are 150 mg/mL and 5.0 mg/mL, respectively. Formulations are dosed by oral gavage (PO) for a final dose of 300 mg/kg delivery agent and 10.0 mg/kg active agent. 0.40 mL of blood sample is collected in heparin tubes from the systemic (femoral artery) cannula from each animal (one sample/time point) at, 5, 15, 30, 60, 90 and 120 minutes. Tubes are chilled on ice immediately following collection and centrifuged at approximately 5° C./3,000 rpm/15 minutes. Plasma is removed, transferred into 96 well plates and stored immediately at −70 C until analyzed by a LC/MS/MS.

Radioimmunoassay and Pharmacokinetic Analysis

Concentrations of immunoreactive active agent in rat plasma are assayed by a radioimmunoassay assay that non-specifically detects native peptide and metabolic products. These concentrations are subsequently used to determine the reported pharmacokinetic parameters. Plasma samples are mixed with radiolabeled active agent and rabbit polyclonal antiserum and then incubated overnight at ~4° C. Bound and free forms of immunoreactive active agent are separated by precipitating the bound fraction by polyethylene glycol-assisted, secondary antibody precipitation. After collecting the bound fraction by centrifugation, the radioactivity is measured by a gamma counter. Data is analyzed by a weighted 4/5 parameter logistic algorithm. For GLP-1 compounds, the standard curve ranges from 9.8 pg/mL to 10000 pg/mL and the upper and lower quantification limits are 150 pg/mL and 4000 pg/mL, respectively. For MC4 agonist peptides, the standard curve ranges from 5.0 ng/mL to 5000 ng/mL and the upper and lower quantification limits are 10 ng/mL and 5000 ng/mL, respectively. Pharmacokinetic analysis is performed using WinNonlin™ Version 3.0 (Pharsight Corporation, Mountain View, Calif.). Plasma concentration time data are reported as mean±standard deviation (SD). Delivery agent efficiency is defined as area under the plasma concentration-time curve measured from 0 to 20 min (AUC) of active agent in the presence of each delivery agent. Representative compounds of formula II (delivery agent) are tested with an active agent in the Rat Oral Delivery assay and the AUC of active agent in the presence of delivery agent is greater than the AUC of the active agent in the absence of the delivery agent.

We claim:
1. A compound of formula (I), or a pharmaceutically acceptable salt thereof:

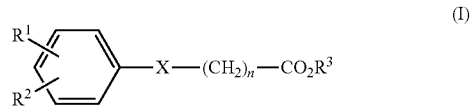

wherein
R$^1$ is NH$_2$;
R$^2$ is H;
R$^3$ is H;
n is 2, 3, 4 or 5; and
X is

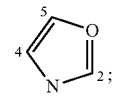

where the phenyl substituent is attached at carbon atom number 4 and the alkanoic acid chain is attached at carbon atom number 2.

2. The compound according to claim 1, selected from

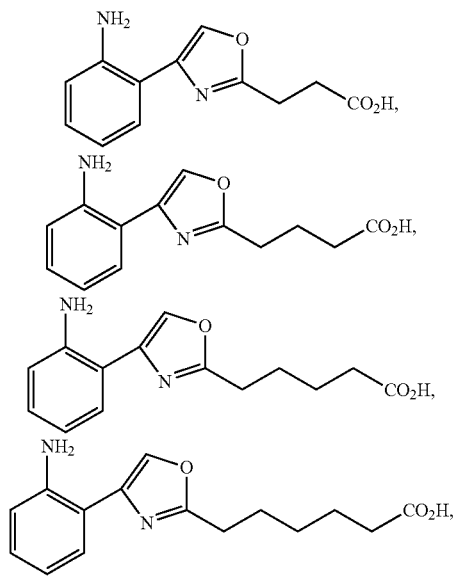

and pharmaceutically acceptable salts thereof.

3. A compound according to claim 2, which is:

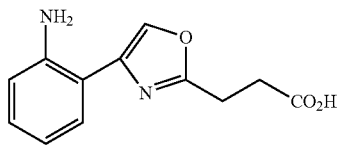 [SMILES: Nc1ccccc1-c1coc(CCC(=O)O)n1]

or a pharmaceutical salt thereof.

4. A compound according to claim 2, which is:

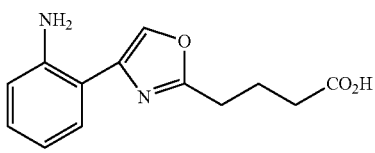 [SMILES: Nc1ccccc1-c1coc(CCCC(=O)O)n1]

or a pharmaceutical salt thereof.

5. A compound according to claim 2, which is:

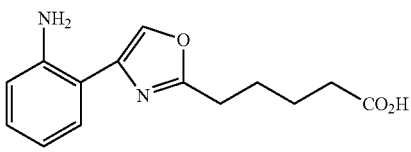 [SMILES: Nc1ccccc1-c1coc(CCCCC(=O)O)n1]

or a pharmaceutical salt thereof.

6. A compound according to claim 2, which is:

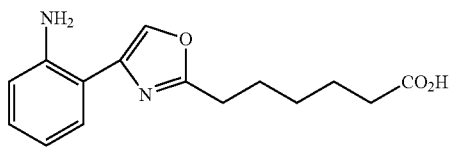 [SMILES: Nc1ccccc1-c1coc(CCCCCC(=O)O)n1]

or a pharmaceutical salt thereof.

7. A pharmaceutical composition comprising:
   a) a compound according to claim 1, or a pharmaceutical salt thereof; and
   b) a GLP-1 compound.

8. The pharmaceutical composition according to claim 7, wherein the GLP-1 compound is a GLP-1 derivative.

9. The pharmaceutical composition according to claim 7, wherein the GLP-1 compound is a GLP-1 analog.

10. The composition according claim 7, wherein the GLP-1 compound is $Val^8$-$Glu^{22}$-GLP-1(7-37)OH.

11. A pharmaceutical composition comprising:
    a) a compound of claim 1 or a pharmaceutical salt thereof; and
    b) an MC4 agonist peptide.

12. The composition of claim 11, wherein the MC4 agonist peptide is selected from the group consisting of:
   Ac-Arg-cyclo[Cys-Glu-His-D-Phe-Arg-Trp-Cys]-$NH_2$;
   Ac-cyclo[hCys-His-D-Phe-Arg-Trp-Cys]-$NH_2$;
   Ac-cyclo [hCys-His-D-Phe-Arg-Trp-penicillamine]-$NH_2$; and
   N-cyclohexanecarbonyl-cyclo[hCys-His-D-Phe-Arg-Trp-penicillamine]-$NH_2$.

* * * * *